(12) United States Patent
Macor et al.

(10) Patent No.: US 6,326,379 B1
(45) Date of Patent: Dec. 4, 2001

(54) FUSED PYRIDINE INHIBITORS OF CGMP PHOSPHODIESTERASE

(75) Inventors: John E. Macor, Flemington; Guixue Yu, West Winsdor, both of NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/393,833

(22) Filed: Sep. 10, 1999

Related U.S. Application Data

(60) Provisional application No. 60/100,665, filed on Sep. 16, 1998.

(51) Int. Cl.[7] .................... A61K 31/437; A61K 31/496; C07D 471/04; A61P 15/10
(52) U.S. Cl. .................... 514/303; 514/212.08; 514/218; 514/228.5; 514/234.2; 514/253.04; 514/278; 540/527; 540/575; 544/61; 544/127; 544/362; 546/20; 546/120
(58) Field of Search ............... 546/120, 20; 514/303, 514/278, 212.08, 218, 234.2, 253.04, 228.5; 540/527, 575; 544/127.61, 362

(56) References Cited

U.S. PATENT DOCUMENTS

| | | | |
|---|---|---|---|
| 3,755,340 | 8/1973 | Hoehn et al. | 260/295.5 |
| 3,787,430 | 1/1974 | Hoehn et al. | 260/296 |
| 3,840,546 | 10/1974 | Hoehn et al. | 260/295.5 |
| 3,855,675 | 12/1974 | Denzel et al. | 260/296 |
| 3,966,746 | 6/1976 | Hoehn et al. | 260/293.6 |
| 3,979,399 | 9/1976 | Hoehn et al. | 260/295.5 |
| 3,987,051 | 10/1976 | Denzel et al. | 260/296 |
| 4,003,903 | 1/1977 | Denzel et al. | 260/295.5 |
| 4,048,182 | 9/1977 | Denzel et al. | 260/295.5 |
| 4,051,236 | 9/1977 | Harris et al. | 424/101 |
| 4,070,362 | 1/1978 | Denzel et al. | 260/295.5 |
| 4,745,121 | 5/1988 | Bare | 514/303 |
| 5,250,534 | 10/1993 | Bell et al. | 514/258 |
| 5,272,147 | 12/1993 | Bell et al. | 514/234.2 |
| 5,346,901 | 9/1994 | Bell et al. | 514/258 |
| 5,426,107 | 6/1995 | Bell et al. | 514/234.2 |
| 5,482,941 | 1/1996 | Terrett | 514/253 |
| 5,488,055 | 1/1996 | Kumar et al. | 514/293 |
| 5,612,359 | 3/1997 | Murugesan | 514/365 |

FOREIGN PATENT DOCUMENTS

| | | |
|---|---|---|
| 655440 | 10/1994 | (EP) . |
| 657426 | 10/1994 | (EP) . |
| 1460059 | 12/1976 | (GB) . |
| WO95/19978 | 7/1995 | (WO) . |
| WO97/03675 | 2/1997 | (WO) . |
| WO97/03985 | 2/1997 | (WO) . |
| WO97/19947 | 6/1997 | (WO) . |
| WO97/23480 | 7/1997 | (WO) . |
| WO97/49683 | 12/1997 | (WO) . |
| WO98/07430 | 2/1998 | (WO) . |
| WO98/08848 | 3/1998 | (WO) . |
| 99/30710 | * 6/1999 | (WO) . |

OTHER PUBLICATIONS

Chemical Abstracts, vol. 116, 1435a7, 1992, Oquist et al.
Chemical Abstracts, vol. 113, 207309, 1990, Tomes et al.
Chemical Abstracts, vol. 112, 441, 1990, Ahn et al.
Chemical Abstracts, vol. 108, 48712, 1988, Davis et al.
Chemical Abstracts, vol. 107, 214090, 1987, Kurtz et al.
Bos et al., "Novel Agonists of $5HT_{2c}$ Receptors . . . ", J. Med. Chem., 1997, vol. 40, 2762–2769.
Chemische Fabrik von Heyden, "Substituted 5–aminopyrazoles", Chem. Abst., 1965, vol. 63, 14871.
Rajfer et al., "Nitric Oxide As a Mediator . . . ", New England Journal of Medicine, 1992, vol. 326, p. 90–94.
Bowman et al., "Cyclic GMP Mediates . . . ", British J. Pharmac., 1984, vol. 81, p. 665–674.
Trigo–Rocha et al., "Nitric Oxide and cGMP . . . ", American J. Physiol., 1993, vol. 264, p. H419–H422.
Martel et al., "Sildenafil", Drugs of the Future, 1997, vol. 22, p. 138–143.
Eisai Co., Abstract of PCT Application WO95/18097, Jul. 1995.
Fujisawa Co., Abstract of PCT Application WO97/24334, Jul. 1997.

* cited by examiner

*Primary Examiner*—Evelyn Mei Huang
(74) *Attorney, Agent, or Firm*—Stephen B. Davis; Anastasia P. Winslow

(57) ABSTRACT

Compounds of the formulas

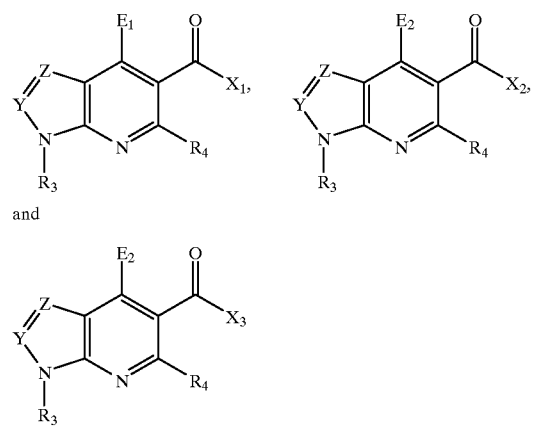

and are useful as inhibitors of cGMP PDE, especially type V.

23 Claims, No Drawings

FUSED PYRIDINE INHIBITORS OF CGMP PHOSPHODIESTERASE

This application claims priority from Ser. No. 60/100,665 filed Sep. 16, 1998, incorporated herein by reference.

FIELD OF THE INVENTION

The present invention relates to fused pyridine compounds, to methods of using such compounds in the treatment of cGMP-associated conditions such as erectile dysfunction, and to pharmaceutical compositions containing such compounds.

BACKGROUND OF THE INVENTION

Erectile dysfunction is the inability to obtain and maintain a penile erection sufficient for sexual intercourse or other sexual expression. A number of factors can place an individual at risk for this disorder, for example, trauma, pelvic surgery, hypercholesterolemia, ischemic heart disease, peripheral vascular disease, chronic renal failure, diabetes, or the use of medicaments such as certain antihypertensive medications or digoxin, or illicit drugs, cigarettes or alcohol. Methods for the treatment of erectile dysfunction include the use of vacuum devices and penile implants, as well as the administration of medicaments such as yohimbine, papaverine and apomorphine. Improved methods for the treatment of this disorder are sought, however, as the aforementioned methods do not provide sufficient efficacy, and/or are accompanied by drawbacks or side effects such as erosion, pain, priapism or gastrointestinal discomfort.

As penile erection is dependent upon the presence of adequate levels of cyclic guanosine 3', 5'-monophosphate (cGMP), especially in corpora cavernosa tissue, administration of an inhibitor of a cGMP phosphodiesterase (cGMP PDE) (and particularly, a selective inhibitor of cGMP PDE Type V (cGMP PDE V)) provides a means for achieving and maintaining an erection, and therefore for treating erectile dysfunction. See Trigo-Rocha et al., "Nitric Oxide and cGMP: mediators of pelvic nerve-stimulated erection in dogs," *Am. J. Physiol.*, Vol. 264 (February 1993); Bowman et al., "Cyclic GMP mediates neurogenic relaxation in the bovine retractor-penis muscle," *Br. J. Pharmac.*, 81, 665–674 (1984); and Rajfer et al., "Nitric Oxide as a Mediator of Relaxation of the Corpus Cavernosum in Response to Nonadrenergic, Noncholinergic Neurotransmission," *New England J. Med.*, 326, 2, 90–94 (January 1992). Sildenafil, for example, has been described as a phosphodiesterase Type V inhibitor useful for the treatment of erectile dysfunction. See *Drugs of the Future*, 22, 138–143 (1997).

The present invention provides novel compounds which are potent and selective inhibitors of cGMP PDE V which may be employed in the treatment of erectile dysfunction. In view of their activity, the present compounds can also be employed in the treatment of other disorders responding to the inhibition of cGMP PDE such as various cardiovascular disorders.

SUMMARY OF THE INVENTION

This invention is directed to the novel fused pyridine compounds of formulas I and II shown below including pharmaceutically acceptable salts thereof, pharmaceutical compositions containing one or more fused pyridines of formulas I and II, and the use of such compounds as inhibitors of cGMP PDE, especially type V.

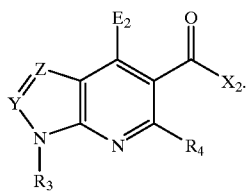

(I)

and

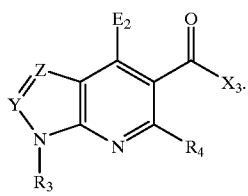

(II)

This invention is also directed to the use of the fused pyridine compounds of formula III shown below including pharmaceutically acceptable salts thereof as inhibitors of cGMP PDE, especially type V.

(III)

In the above formulas:

$E_1$ is —O—$R_1$, —S—$R_1$, —NH—$A_1$-cycloalkyl, —NH—$A_1$-substituted cycloalkyl, —NH—$A_1$-heterocyclo, or —NH—$A_1$-heteroaryl.

$E_2$ is —NH—$A_1$-alkoxy, —NH—$A_1$—$CO_2$alkyl,

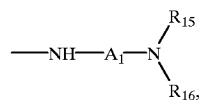

—NH—$A_1$-aryl, or —NH—$A_1$-substituted aryl.

$R_1$ is —$A_1$-cycloalkyl, —$A_1$-subsituted cycloalkyl, —$A_1$-alkoxy,

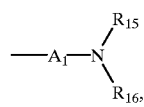

—$A_1$-aryl, —$A_1$-substituted aryl, —$A_1$-heterocyclo, or —$A_1$-heteroaryl.

$X_1$ is —O—$A_1$—$R_2$, —O—$R_9$, —N ($R_9$) ($R_{10}$),

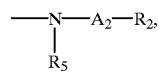

a monocylic ring

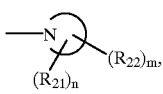

a fused bicyclic ring

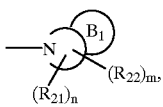

or a spiro ring

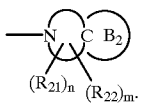

$X_2$ is —O—$A_1$—$R_{25}$,

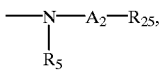

a monocyclic ring

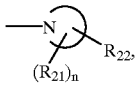

a fused bicyclic ring

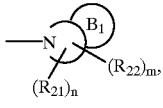

or a spiro ring

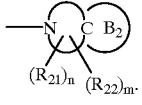

$X_3$ is —O—$R_9$, —O—$A_1$—O—$R_9$, —N($R_9$)($R_{10}$),

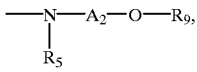

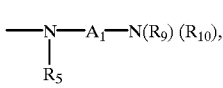

or a monocyclic ring

$A_1$ is an alkylene or substituted alkylene bridge of 1 to 10 carbons.

Y is nitrogen or C($R_6$).

Z is nitrogen or C($R_7$) with the proviso that at least one of Y or Z is nitrogen.

$R_3$ is hydrogen, alkyl, cycloalkyl, substituted cycloalkyl, substituted alkyl, —$A_1$-aryl, —$A_1$-substituted aryl, —$A_1$-cycloalkyl, or —$A_1$-substituted cycloalkyl.

$R_6$ and $R_7$ are independently selected from the group consisting of hydrogen, alkyl, substituted alkyl, cycloalkyl, substituted cycloalkyl, —$A_1$-cycloalkyl, —$A_1$-substituted cycloalkyl, —$A_1$-aryl, $A_1$-substituted aryl, —$A_1$-heterocyclo, and $A_1$-heteroaryl.

$R_4$ is hydrogen, —N($R_{12}$)($R_{13}$), —O$R_{12}$ or 1- or 3-imidazolyl.

$A_2$ is a direct bond, an alkylene or substituted alkylene bridge of 1 to 10 carbons, an alkenyl or substituted alkenyl bridge of 2 to 10 carbons having one or more double bonds, or an alkynyl or substituted alkynyl bridge of 2 to 10 carbons having one or more triple bonds.

$R_2$ is cycloalkyl, substituted cycloalkyl, aryl, substituted aryl, heterocyclo, heteroaryl, cycloalkyl-$A_3$-cycloalkyl, cycloalkyl-$A_3$-substituted cycloalkyl, cycloalkyl-$A_3$-aryl, cycloalkyl-$A_3$-substituted aryl, cycloalkyl-$A_3$-heterocyclo, cycloalkyl-$A_3$-heteroaryl, substituted cycloalkyl-$A_3$-cycloalkyl, substituted cycloalkyl-$A_3$-substituted cycloalkyl, substituted cycloalkyl-$A_3$-aryl, substituted cycloalkyl-$A_3$-substituted aryl, substituted cycloalkyl-$A_3$-heterocyclo, substituted cycloalkyl-$A_3$-heteroaryl, aryl-$A_3$-cycloalkyl, aryl-$A_3$-substituted cycloalkyl, aryl-$A_3$-aryl, aryl-$A_3$-substituted aryl, aryl-$A_3$-heterocyclo, aryl-$A_3$-heteroaryl, substituted aryl-$A_3$-cycloalkyl, substituted aryl-$A_3$-substituted cycloalkyl, substituted aryl-$A_3$-aryl, substituted aryl-$A_3$-substituted aryl, substituted aryl-$A_3$-heterocyclo, substituted aryl-$A_3$-heteroaryl, heterocyclo-$A_3$-cycloalkyl, heterocyclo-$A_3$-substituted cycloalkyl, heterocyclo-$A_3$-aryl, heterocyclo-$A_3$-substituted aryl, heterocyclo-$A_3$-heterocyclo, heterocyclo-$A_3$-heteroaryl, heteroaryl-$A_3$-cycloalkyl, heteroaryl-$A_3$-substituted cycloalkyl, heteroaryl-$A_3$-aryl, heteroaryl-$A_3$-heterocyclo, heteroaryl-$A_3$-heteroaryl, cyano, —O$R_9$, —S$R_9$, —(C=O)$R_9$, —N($R_9$)($R_{10}$), —$CO_2R_9$, —(C=O)N($R_{12}$)($R_{13}$), —$SO_2$N($R_{12}$)($R_{13}$), —N$R_{11}$(C=O)$R_{19}$, —N$R_{11}$(C=O)N($R_{12}$)($R_{13}$), —O—(C=O)N($R_{12}$)($R_{13}$) provided that $A_2$ is not a direct bond, —N$R_{11}$$CO_2$$R_{19}$, —(C=O)N($R_{11}$)$CH_2$$CO_2$$R_{19}$, nitrogen when $A_2$ is alkynyl ending in a triple bond, or NH when $A_2$ is alkenyl ending in a double bond.

$R_{25}$ is cycloalkyl, substituted cycloalkyl, aryl, substituted aryl, heterocyclo, heteroaryl, cycloalkyl-$A_3$-cycloalkyl, cycloalkyl-$A_3$-substituted cycloalkyl, cycloalkyl-$A_3$-aryl, cycloalkyl-$A_3$-substituted aryl, cycloalkyl-$A_3$-heterocyclo, cycloalkyl-$A_3$-heteroaryl, subsituted cycloalkyl-$A_3$-cycloalkyl, substituted cycloalkyl-$A_3$-substituted cycloalkyl, substituted cycloalkyl-$A_3$-aryl, substituted cycloalkyl-$A_3$-substituted aryl, substituted cycloalkyl-$A_3$-heterocyclo, substituted cycloalkyl-$A_3$- heteroaryl, aryl-$A_3$-cycloalkyl, aryl-$A_3$-substituted cycloalkyl, aryl-$A_3$-aryl, aryl-$A_3$-substituted aryl, aryl-$A_3$-heterocyclo, aryl-$A_3$-heteroaryl, substituted aryl-$A_3$-cycloalkyl, substituted aryl-$A_3$-substituted cycloalkyl, substituted aryl-$A_3$-aryl, substituted aryl-$A_3$-substituted aryl, substituted aryl-$A_3$-heterocyclo, substituted aryl-$A_3$-heteroaryl, heterocyclo-$A_3$-cycloalkyl, heterocyclo-$A_3$-substituted cycloalkyl, heterocyclo-$A_3$-aryl, heterocyclo-$A_3$-substituted aryl, heterocyclo-$A_3$-heterocyclo, heterocyclo-$A_3$-heteroaryl, heteroaryl-$A_3$-cycloalkyl, heteroaryl-$A_3$-substituted cycloalkyl, heteroaryl-$A_3$-aryl, heteroaryl-$A_3$-substituted aryl, heteroaryl-$A_3$-heterocyclo, heteroaryl-$A_3$-heteroaryl, cyano, $-S-R_9$, $-(C=O)R_{11}$, $-CO_2R_{19}$, $-(C=O)N(R_{12})(R_{13})$, $-SO_2N(R_{12})R_{13})$, $-NR_9(C=O)R_{10}$, $-NR_{11}(C=O)N(R_{12})(R_{13})$, $-O-(C=O)N(R_{12})(R_{13})$ provided that $A_2$ is not a direct bond, $-NR_{11}CO_2R_{19}$, $-(C=O)N(R_{11})CH_2CO_2R_{19}$, nitrogen when $A_2$ is alkynyl ending in a triple bond, or NH when $A_2$ is alkenyl ending in a double bond.

$A_3$ is a direct bond, an alkylene or substituted alkylene bridge of 1 to 10 carbons, an alkenyl or substituted alkenyl bridge of 2 to 10 having one or more double bonds, an alkynyl or substituted alkynyl bridge of 2 to 10 carbons having one or more triple bonds, $-(CH_2)_d-O-(CH_2)_e-$, $-(CH_2)_d-S-(CH_2)_e-$, or $-(CH_2)_d-(C=O)-(CH_2)_e-$.

d is zero or an integer from 1 to 6.

e is zero or an integer from 1 to 6.

$R_5$ is hydrogen, alkyl, substituted alkyl, cycloalkyl, substituted cycloalkyl, aryl, $-A_1$-aryl, substituted aryl, $-A_1$-substituted aryl, heterocyclo, $-A_1$-heterocyclo, heteroaryl or $-A_1$-heteroaryl.

$R_9$, $R_{10}$, $R_{11}$, $R_{12}$, $R_{13}$, $R_{15}$, $R_{16}$, and $R_{19}$ are independently selected from the group consisting of hydrogen, alkyl, substituted alkyl, cycloalkyl, substituted cycloalkyl, aryl, substituted aryl, heterocyclo, heteroaryl, $-A_1$-cycloalkyl, $-A_1$-substituted cycloalkyl, $-A_1$-aryl, $-A_1$-subsituted aryl, $-A_1$-heterocyclo and $-A_1$-heteroaryl, or $R_{12}$ and $R_{13}$ taken together with the N atom to which they are attached represent a heterocyclo ring.

represents a monocyclic heterocyclo or heteroaryl ring of 4 to 8 atoms containing up to 3 additional heteroatoms (up to 2 additional heteroatoms when the ring is 4 atoms) which are selected from one or two oxygen atoms and/or one or two sulfur atoms and/or one, two or three nitrogen atoms.

$R_{21}$ is attached to an available carbon or nitrogen atom and is hydrogen, alkyl, halogen, hydroxy, trifluoromethyl,-amino, alkoxy or carboxy.

$R_{22}$ is attached to an available carbon or nitrogen atom and is keto, $-(C=O)R_{23}$, $-CO_2-R_{23}$, $-NH-(C=O)-R_{23}$, $-N(alkyl)_2$, $-A_1$-hydroxy, $-A_1-N(R_9)(R_{10})$, $-A_1$-alkoxy, $-A_1$-carboxy, $-A_2$-cycloalkyl, $-A_2$-substituted cycloalkyl, $-A_2$-aryl, $-A_2$-substituted aryl, $-A_2$-heterocyclo, or $-A_2$-heteroaryl.

n is one or two.

m is zero or one.

$R_{23}$ is alkyl, $-N(R_9)(R_{10})$, $-A_1$-hydroxy, $-A_1-N(R_9)(R_{10})$ $-A_1$-carboxy, $-A_2$-cycloalkyl, $-A_2$-substituted cycloalkyl, $-A_2$-aryl, $-A_2$-substituted aryl, $-A_2$-heterocyclo or $-A_2$-heteroaryl.

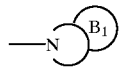

represents a fused bicyclic ring wherein the monocyclic ring

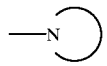

is defined previously and

represents a cycloalkyl, substituted cycloalkyl, aryl, substituted aryl, heterocyclo or heteroaryl having two carbon atoms in common with the monocyclic ring

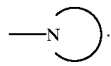

represents a spiro ring wherein the monocyclic ring

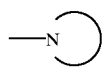

is defined previously and

represents a cycloalkyl, substituted cycloalkyl, aryl, substituted aryl, heterocyclo or heteroaryl ring having a common carbon with the monocyclic ring

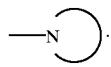

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The term "alkoxy" refers to an alkyl group bonded through an oxygen (—O—). The term "alkylthio" refers to an alkyl group bonded through a sulfur (—S—).

The term "substituted alkyl" refers to an alkyl chain as defined above having one, two, or three substituents selected from halo, cyano, hydroxy, alkoxy, alkylthio, amino, —NH(alkyl), —NH(cycloalkyl), —N(alkyl)2, carboxy and —CO$_2$-alkyl.

The term "alkylene" refers to a bridge of 1 to 10 carbons such as —CH$_2$—, —(CH$_2$)$_4$—, etc.

The term "substituted alkylene" refers to an alkylene bridge as previously defined having one, two, or three substituents selected from alkyl, substituted alkyl, halo, cyano, hydroxy, alkoxy, alkylthio, amino —NH(alkyl), —NH(cycloalkyl), —N(alkyl)$_2$, carboxy, —CO$_2$-alkyl, cycloalkyl, substituted cycloalkyl, aryl, substituted aryl, heterocyclo, and heteroaryl.

The term "alkenyl" refers to a bridge of 2 to 10 carbons containing at least one double bond such as —CH=CH—, —CH$_2$—CH=CH—, etc.

The term "subsituted alkenyl" refers to a bridge of 2 to 10 carbons containing at least one double bond as defined previously having, one, two or three substituents selected from alkyl, substituted alkyl, halo, cyano, hydroxy, alkoxy, alkylthio, amino, —NH(alkyl), —NH(cycloalkyl), —N(alkyl)$_2$, carboxy, —CO$_2$-alkyl, cycloalkyl, substituted cycloalkyl, aryl, substituted aryl, heterocyclo, and heteroaryl.

the term "alkynyl" refers to a bridge of 2 to 10 carbons containing at least one triple bond such as —C≡C—, —CH$_2$—C≡C—, etc.

The term "substituted alkynyl" refers to a bridge of 2 to 10 carbons containing at least one triple bond as defined previously having one, two, or three substituents selected from alkyl, subsituted alkyl, halo, cyano, hydroxy, alkoxy, alkylthio, amino, —NH(alkyl), —NH(cycloalkyl), —N(alkyl)$_2$, carboxy, —CO$_2$-alkyl, cycloalkyl, substituted cycloalkyl, aryl, substituted aryl, heterocyclo and heteroaryl.

The term "cycloalkyl" refers to cyclic hydrocarbon groups of 3 to 9 carbon atoms, preferably 3 to 7 carbon atoms, which can be fully saturated or partially unsaturated. Also included within this definition are bicyclic cycloalkyl rings having a fused phenyl ring such

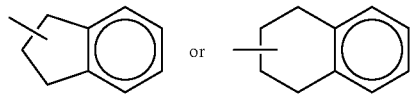

and bicyclic rings having a carbon-carbon bridge of 3 or 4 carbons such as

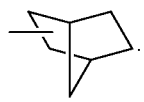

The term "substituted cycloalkyl" refers to such cycloalkyl groups as defined above having one, two or three substituents selected from alkyl, substituted alkyl, halo, cyano, hydroxy, alkoxy, alkylthio, amino, —NH(alkyl), —NH(cycloalkyl), —N(alkyl)$_2$, carboxy, —CO$_2$-alkyl, keto, =N—OH, =N—O-lower alkyl, and a five or six membered ketal, i.e. 1,3-dioxolane or 1,3-dioxane.

The term "aryl" refers to phenyl, 1-naphthyl or 2-naphthyl, with phenyl being preferred.

The term "substituted aryl" refers to such aryl groups as defined previously having one, two or three substituents selected from alkyl, substituted alkyl, halo, cyano, hydroxy, alkoxy, alkylthio, amino, —NH(alkyl), —NH(cycloalkyl), —N(alkyl) $_2$, carboxy, —CO$_2$-alkyl, keto, —(C=O)NH$_2$, —(C=O)NH(alkyl), —(C=O)NH(cycloalkyl), —(C=O)N(alkyl)$_2$, —(C=O)alkyl, —SO$_2$NH$_2$, —O—(C=O)alkyl, —NH$_2$—CH$_2$-carboxy, —NH—CH$_2$—CO$_2$-alkyl, and a five or six membered ring containing two oxygen atoms such as

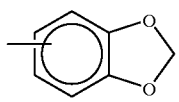

or

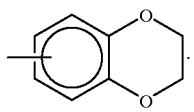

Substituted phenyl having one, two or three substituents as described above is the preferred substituted aryl.

The term "halo" refers to chloro, bromo, fluoro and iodo.

The term "heterocyclo" refers to substituted and unsubstituted fully saturated or partially unsaturated 3 to 7 membered monocyclic groups, 7 to 11 membered bicyclic groups and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that each ring contains at least one carbon atom. The fused ring completing the bicyclic and tricyclic groups may be a cycloalkyl, substituted cycloalkyl, aryl or subsituted aryl as defined above. The bicyclic ring may also be formed by having a bridge of 2 or 3 carbons between available carbon atoms or between an available carbon and nitrogen atoms such as

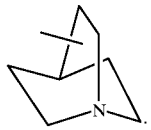

The nitrogen and sulfur atoms may optionally be oxidized and the nitrogen atom may optionally be quaternized. The heterocyclo group may be attached at any available nitrogen or carbon atom. The heterocyclo ring may contain one, two or three substituents attached to an available carbon or nitrogen atom selected from alkyl, substituted alkyl, halo, cyano, hydroxy, alkoxy, alkylthio, amino, —NH(alkyl), —NH(cycloalkyl), —N(alkyl)$_2$, carboxy, —CO$_2$-alkyl, keto, —(C=O)NH$_2$, —(C=O)NH(alkyl), —(C=O)NH (cycloalkyl), —(C=O)N(alkyl)$_2$, —(C=O)alkyl, —O—(C=O)alkyl, —NH—CH$_2$-carboxy, —NH—CH$_2$—CO$_2$-alkyl, =N—OH, =N—O-alkyl, and a five or six membered ring, i.e., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicylic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less. The fused rings completing the bicyclic and tricyclic groups may be a cycloalkyl, substituted cycloalkyl, aryl or substituted aryl as defined above. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain one, two or three substituents attached to an available carbon or nitrogen atom selected from alkyl, substituted alkyl, halo, cyano, hydroxy, alkoxy, alkylthio, amino, —NH(alkyl), —NH (cycloalkyl), —N(alkyl)$_2$, carboxy, —CO$_2$-alkyl, keto, —(C=O)NH$_2$, —(C=O)NH(alkyl), —(C=O)NH (cycloalkyl), —(C=O)N(alkyl)2, —(C=O)alkyl, —O—(C=O)alkyl, —NH—CH$_2$-carboxy, —NH—CH$_2$—CH$_2$—CO$_2$-alkyl, and a five or six membered ring, i.e., 1,3-dioxolane or 1,3-dioxane.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, and the like.

Exemplary bicyclic heteroaryl groups include indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrolinyl, acridinyl, phenanthridinyl, xanthenyl and the like.

Throughout the specification, groups and substituents thereof may be chosen to provide stable moieties and compounds.

The compounds of formulas I, II and III form salts which are also within the scope of this invention. Reference to a compound of formulas I, II or III herein is understood to include reference to salts thereof, unless otherwise indicated. The term "salt(s)", as employed herein, denotes acidic and/or basic salts formed with inorganic and/or organic acids and bases. In addition, when a compound of formula I contains a both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formulas I, II and III may be formed, for example, by reacting a compound I, II or III with an amount of acid or base, such as an equivalent amount, in a medium such as one in which the salt precipitates or in an aqueous medium followed by lyophilization.

The compounds of formulas I, II and III which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulforiates, bisuifates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formulas I, II and III which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of formulas I, II or III or a salt and/or solvate thereof. Solvates of the compounds of formulas I, II and III are preferably hydrates.

Compounds of the formulas I, II and III and salts thereof, may exist in their tautomeric form (for example, as an amide or imino ether). All such tautomeric forms are contemplated herein as part of the present invention.

All stereoisomers of the present compounds, such as those which may exist due to asymmetric carbons on various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

METHODS OF PREPARATION

The compounds of the present invention may be prepared by methods such as those illustrated in the following Scheme I to IV. Solvents, temperatures, pressures, and other reaction conditions may readily be selected by one of ordinary skill in the art. Starting materials are commercially available or readily prepared by one of ordinary skill in the art.

High Speed Analoging (HSA) may be employed in the preparation of compounds, for example, where the intermediates possess a carboxylic acid group or activated aromatic position, such as the 4 position of a 4-halopyridine. In the same manner, substitutions on the fused five membered ring, such as pyrazoles, imidazoles, and triazoles, may also be achieved through HSA.

Compounds of formulas Ia, IIa and IIIa [wherein E is $E_1$ or $E_2$, X is $X_1$, $X_2$ or $X_3$, Y is nitrogen, and Z is $C(R_7)$] can be prepared via the aminolysis or esterification of a compound of formula IV using an appropriate carboxylic acid activating reagent and an appropriate amine or alcohol of the formulas $X_1$—H, $X_2$—H or $X_3$—H in an inert solvent. Exemplary carboxylic acid activating agents include carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, including tetrahydrofuran and dioxane, N,N-dimethylformamide, acetonitrile, or methylene chloride.

Compounds of formula IV can be prepared by the hydrolysis of compounds of formula V using a hydroxide source. Exemplary hydroxide sources include sodium hydroxide or lithium hydroxide. Exemplary solvents include water, alcohols, and mixtures of ethers/water.

Compounds of formula V can be prepared by reacting compounds of formula VI with an amine, thiol or alcohol of the formulas $E_1$—H or $E_2$—H. The reaction may be performed in an inert solvent as appropriate, such as ethanol or N,N-dimethylformamide, in the presence of an appropriate base, such as triethylamine for amines and sodium hydride for thiol or alcohols, and is typically performed at elevated temperatures.

SCHEME I

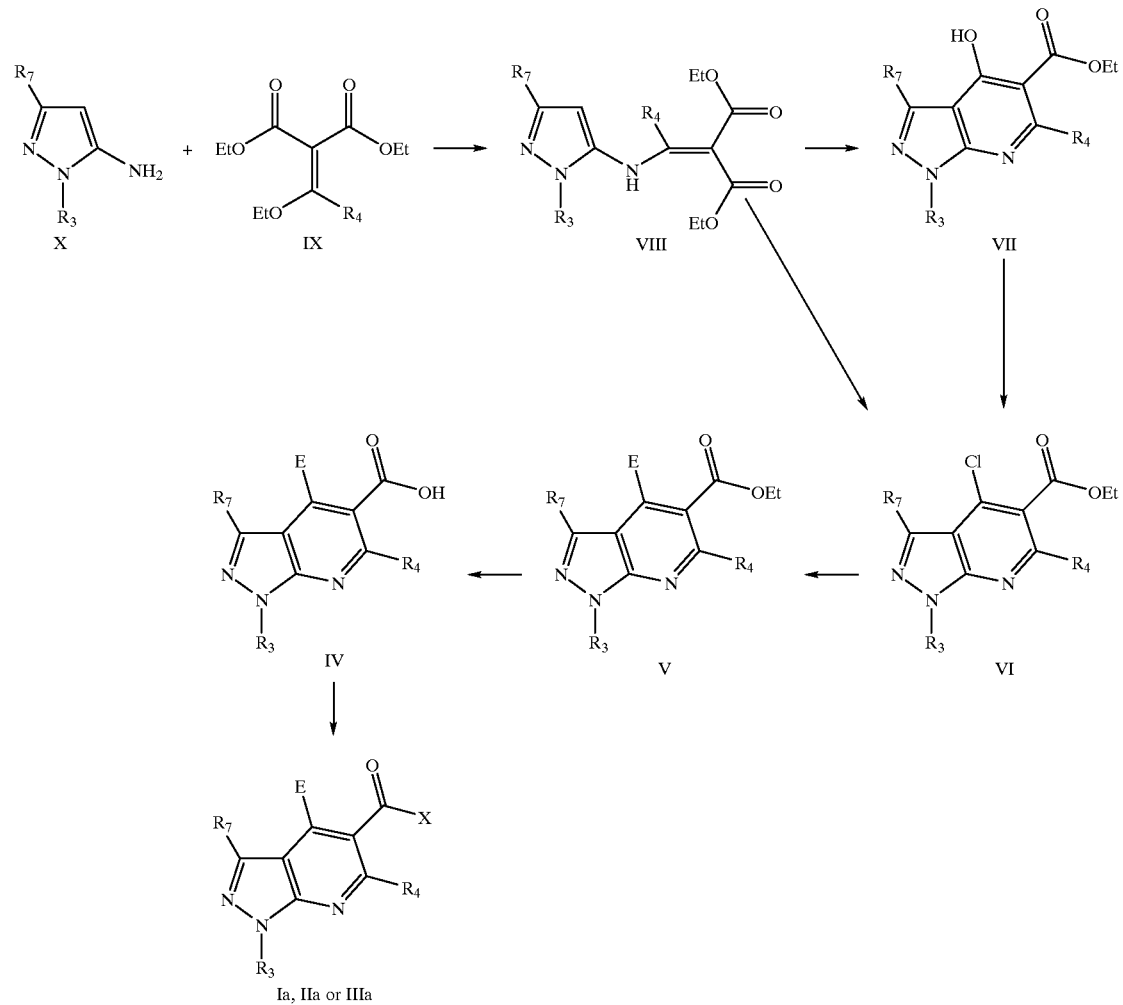

Ia, IIa or IIIa

Compounds of formula VI can be prepared from compounds of either formula VIII or formula VII by reacting with an appropriate dehydrating agent typically under elevated temperatures. Exemplary dehydrating agents include $POCl_3$, $PCl_5$, $SOCl_2$ and oxalyl chloride.

Compounds of formula VII can be prepared from compounds of formula VIII via an intramolecular cyclization typically performed at elevated temperatures in an inert solvent as appropriate or in neat form.

Compounds of formula VIII can be prepared by combining compounds of formula X and IX either neat or in an inert solvent as appropriate, typically such reaction is performed at elevated temperatures.

Compounds of formula X and formula IX are either commercially available or available via methods known to one skilled in the art. For example, compounds of formula X may be prepared as described in French Patent 1,403,372 [*Chemical Abstracts*, 1965, Volume 63, 14871a].

or palladium-catalyzed hydrogenation using platinum or palladium on carbon, hydrogen and an inert solvent such as ethanol or methanol or, alternatively, by use of a stoichiometric reducing agent, such as stannous(II) chloride, in an inert solvent such as ethyl acetate.

Compounds of formula XIV can be prepared by reacting compounds of formula XV with amines of the formula $R_3NH_2$. The reaction may be performed in an inert solvent as appropriate, such as ethanol, in the presence of appropriate base, such as triethylamine, and typically under elevated temperatures.

Compounds of formula XV can be prepared by reacting compounds of formula XVI with an amine, thiol or alcohol of the formula E—H. The reaction may be performed in an inert solvent as appropriate, such as N,N-dimethylformamide, in the presence of an appropriate base, such as triethylamine for amines and sodium hydride for thiols or alcohols.

Methods of synthesis of compounds of formulas XVII, XVI, XV, XIV, XIII, XII, and XI are known to one skilled

SCHEME II

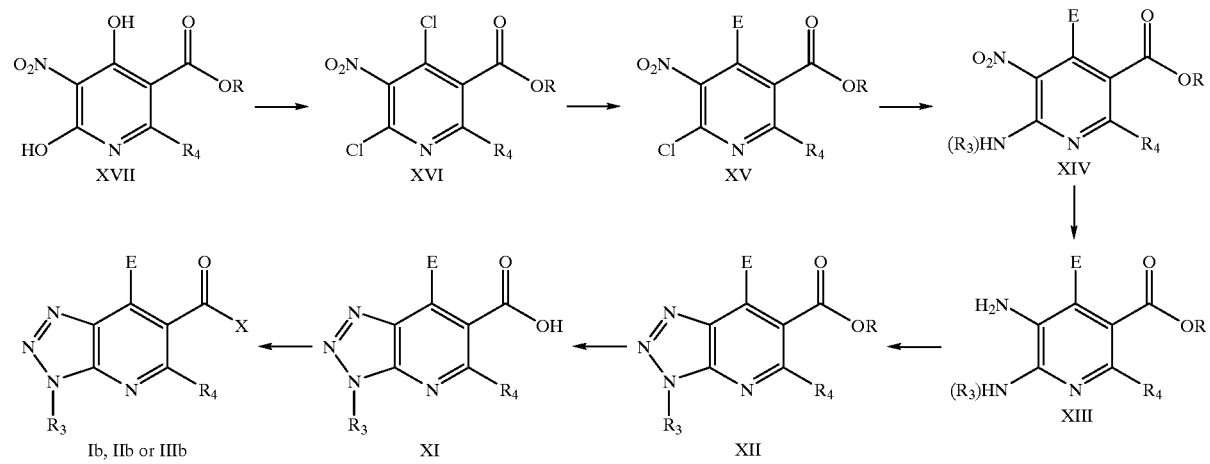

Compound of formula Ib, IIb or IIIb [wherein E is $E_1$ or $E_2$, X is $X_1$, $X_2$ or $X_3$, and Y and Z are both nitrogen] can be prepared via the aminolysis or esterification of a compound of formula XI using an appropriate carboxylic acid activating reagent and an appropriate amine or alcohol of the formula X—H in an inert solvent. Exemplary carboxylic acid activating agents include carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, including tetrahydrofuran and dioxane, N,N-dimethylformamide, acetonitrile, or methylene chloride.

Compounds of formula XI can be prepared from by the hydrolysis of compounds of formula XII using a hydroxide source. Exemplary hydroxide sources include sodium hydroxide or lithium hydroxide. Exemplary solvents include water, alcohols, and mixtures of ethers/water.

Compounds of formula XII can be prepared by treating a compound of formula XIII with a diazatizing reagent in an acidic aqueous medium. Sodium nitrite is an exemplary diazatizing reagent and dilute (1N) HCl is an exemplary reaction solvent.

Compounds of formula XIII can be prepared via the reduction of a compound of formula XIV in an inert solvent. This reduction may, for example, be mediated via a platinum in the art. For example such methodology can be found in U.S. Pat. No. 4,070,362, U.S. Pat. No. 4,003,908, and U.S. Pat. No. 4,048,182. Compounds of formula XVII are either commercially available or prepared by methods known to one skilled in the art.

Scheme III

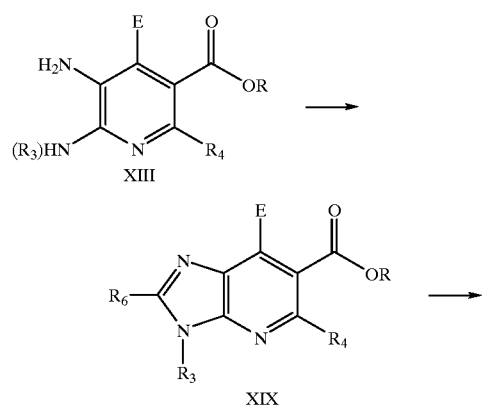

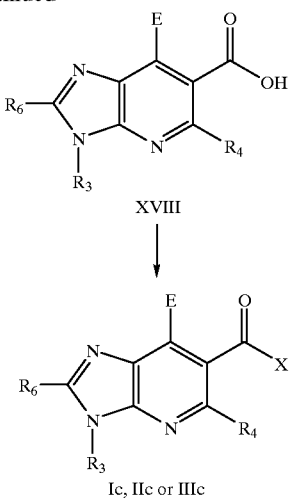

XVIII

↓

Ic, IIc or IIIc

Compounds of formula Ic, IIc and IIIc [wherein E is $E_1$ or $E_2$ and X is $X_1$, $X_2$ or $X_3$, Y is $C(R_6)$ and Z is nitrogen] can be prepared via the aminolysis or esterification of a compound of formula XVIII using an appropriate carboxylic acid activating reagent and an appropriate amine or alcohol of the formula X-H in an inert solvent. Exemplary carboxylic acid activating agents include carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, including tetrahydrofuran and dioxane, N,N-dimethylformamide, acetonitrile, or methylene chloride.

Compounds of formula XVIII can be prepared from by the hydrolysis of compounds of formula XIX using a hydroxide source. Exemplary hydroxide sources include sodium hydroxide or lithium hydroxide. Exemplary solvents include water, alcohols, and mixtures of ethers/water.

Compounds of formula XIX can be prepared from the condensation of compounds of formula XIII with an activated ester derivative from an acid of the formula $R_6$—$CO_2H$ under basic conditions in an inert solvent typically under elevated temperatures. Exemplary activated esters include acid chlorides derived from $R_6$—$CO_2H$, N,N-dialkylamide acetals (including, for example, N,N-dimethylformamide dimethyl acetal) and activated esters derived from the reaction of $R_6$—$CO_2H$ with exemplary carboxylic acid activating agents such as carbonyldiimidazole, dicyclohexylcarbodiimide, pentofluorophenol trifluoroacetate, or 1-(3-dimethylaminopropyl)-3-ethylcarbodiimide. Exemplary bases include sodium hydride, potassium hydride, cesium carbonate, potassium carbonate, potassium hexamethyldisilazide, and potassium t-butoxide. Exemplary inert solvents include ethers, N,N-dimethylformamide, and acetonitrile.

Compounds of formula XIII are prepared as discussed in Scheme II.

Scheme IV

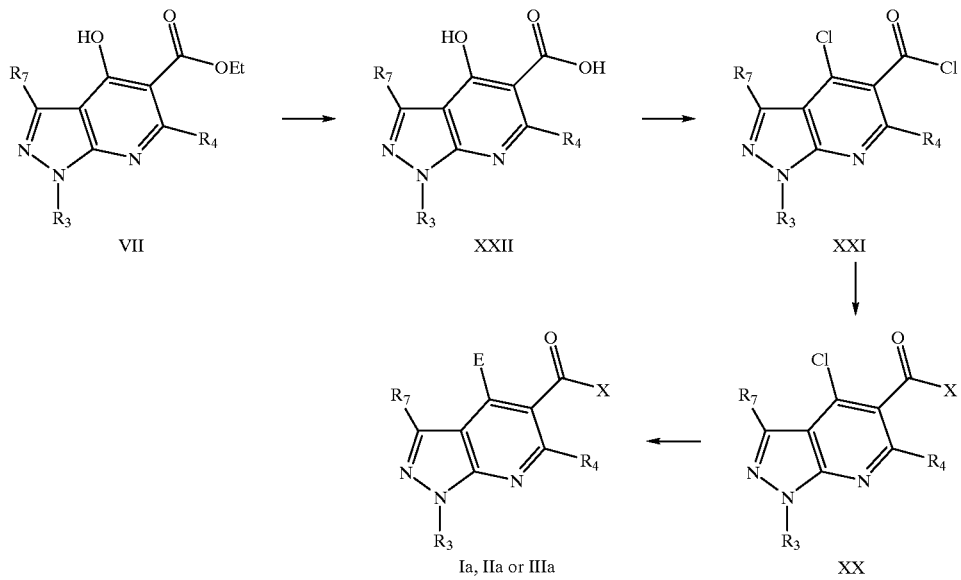

Compounds of formula Ia, IIa and IIIa [wherein E is $E_1$ or $E_2$, X is $X_1$, $X_2$ or $X_3$, Y is nitrogen, and Z is $C(R_7)$] can also be prepared by reacting compounds of formula XX with an amine, thiol or alcohol of the formula E—H. The reaction may be performed in an inert solvent as appropriate, such as N,N-dimethylformamide, in the presence of an appropriate base, such as triethylamine for amines and sodium hydride for alcohols, and typically under elevated temperatures.

Compounds XX can be prepared by reacting compounds of formula XXI with an appropriate amine or alcohol of thee formula X—H in an inert solvent in the presence of an appropriate base such as triethylamine. Exemplary inert solvents include ethers, including tetrahydrofuran and dioxane, N,N-dimethylformamide, acetonitrile, or methylene chloride.

Compounds XXI can be prepared from compounds of formula XXII by reacting with an appropriate dehydrating agent typically under elevated temperatures. Exemplary dehydrating agents include $POCl_3$, $PCl_5$, $SOCl_2$ and oxalyl chloride.

Compounds XXII can be prepared from by the hydrolysis of compounds of formula VII using a hydroxide source. Exemplary hydroxide sources include sodium hydroxide or lithium hydroxide. Exemplary solvents include water, alcohols, and mixtures of ethers/water.

Compound VII can be prepared as described in Scheme I.

Preferred Compounds and Method

The following compounds of formula I and II are preferred:

Y is nitrogen.

Z is nitrogen or $C(R_7)$ $E_1$ is —O—$R_1$, —NH—$A_1$-cycloalkyl, —NH—Au-heterocyclo, or —NH—$A_1$-heteroaryl.

$E_2$ is —NH—$A_1$-alkoxy,

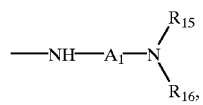

—NH—$A_1$-substituted phenyl, or —NH—$A_1$—$CO_2$-alkyl.

$R_1$ is —$A_1$-substituted phenyl.

$X_1$ is —O—$A_1$-heteroaryl, —O—$A_1$-heterocyclo,

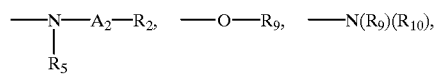

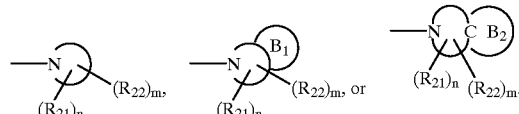

$X_2$ is —O—$A_2$-heteroaryl,

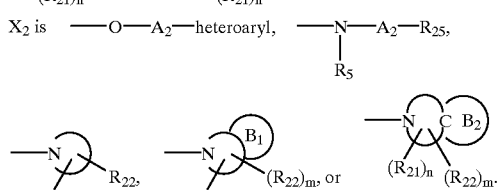

$R_7$ is hydrogen.

$R_4$ is hydrogen.

$R_3$ is straight or branched chain alkyl of 1 to 4 carbons.

$R_5$ is hydrogen, alkyl, —$CO_2$-alkyl, —$A_1$-phenyl, or —$A_1$-heteroaryl wherein alkyl is straight or branched chain of 1 to 4 carbons.

$R_2$ is —(C=O)$R_9$, —S—$R_9$, —O—$R_9$, —N($R_9$)($R_{10}$), —$NR_{11}CO_2R_{19}$, —(C=O)N($R_{11}$)$CH_2CO_2R_{19}$, —$NR_{11}$(C=O)$R_{19}$, —$CO_2R_9$, nitrogen when $A_2$ is alkynyl ending in a triple bond, —(C=O)N($R_{12}$)($R_{13}$), phenyl, substituted phenyl, cycloalkyl, heterocyclo, heteroaryl, cycloalkyl-$A_3$-phenyl, phenyl-$A_3$-heteroaryl, heterocyclo-$A_3$-phenyl, or heterocyclo-$A_3$-heterocyclo.

$R_{25}$ is —S—$R_9$, —$NR_{11}CO_2R_{19}$, nitrogen when $A_2$ is alkynyl ending in a triple bond, —(C=O)N($R_{11}$)$CH_2CO_2R_{19}$, —$NR_{11}$(C=O)$R_{19}$, —$CO_2R_9$, —(C=O)N($R_{12}$)($R_{13}$), phenyl, substituted phenyl, cycloalkyl, heterocyclo, heteroaryl, cycloalkyl-$A_3$-phenyl, heterocyclo-$A_3$-phenyl, phenyl-$A_3$-heteroaryl or heterocyclo-$A_3$-heterocyclo.

$A_1$ is an alkylene or substituted alkylene bridge of 1 to 6 carbons wherein said substituent is a straight or branched chain alkyl of 1 to 4 carbons.

$A_2$ is a direct bond, an alkylene or substituted alkylene bridge of 1 to 6 carbons wherein said substituent is one or two members selected from alkyl, phenyl, substituted phenyl, —$CO_2$-alkyl, carboxy, hydroxy, —NH—(C=O)-alkyl, and —$CH_2$—(C=O)—$NH_2$, an alkenyl bridge of 2 to 4 carbons having one double bond, or an alkynyl bridge of 2 to 3 carbons having one triple bond wherein alkyl is straight or branched chain of 1 to 4 carbons.

The term "heterocyclo" in the preferred definitions refers to a substituted or unsubstituted fully saturated or partially saturated 5 to 7 membered monocyclic rings containing one or two heteroatoms selected from oxygen, sulfur and nitrogen and bicyclic rings wherein the monocyclic ring as defined above is fused to a phenyl or substituted phenyl or wherein a bridge of 2 or 3 carbons is present between available carbon and nitrogen atom. The nitrogen and sulfur atoms may optionally be oxidized and the nitrogen atom may optionally be quaternized. The heterocyclo group may be attached at any available nitrogen or carbon atom. The heterocyclo ring may contain one or two substituents attached to an available carbon or nitrogen atom selected from alkyl, keto and —$CO_2$-alkyl, wherein alkyl is straight or branched chain of 1 to 4 carbons.

The term "heteroaryl" in the preferred definitions refers to a substituted or unsubstituted aromatic 5 or 6 membered monocyclic ring containing one or two oxygen or sulfur atoms and/or from one to four nitrogen atoms provided that the total number of heteroatoms in the ring is four or less, and bicyclic rings wherein the monocyclic ring as defined above is fused to a phenyl or substituted phenyl. The nitrogen and sulfur atoms may optionally be oxidized and the nitrogen atom may optionally be quaternized. The heteroaryl group may be attached at any available nitrogen or carbon atom. The heteroaryl ring may contain one or two substituents attached to an available carbon or nitrogen atom selected from straight or branched chain alkyl of 1 to 4 carbons and halo.

The term "cycloalkyl" in the preferred definitions refers to a fully saturated cyclic hydrocarbon group of 3 to 7 carbons and such cycloalkyl rings fused to a phenyl ring or such cycloalkyl rings 5 to 7 carbons having a carbon-carbon bridge of 3 or 4 carbons.

The term "substituted phenyl" refers to a phenyl ring having one, two, or three substituents selected from alkyl, halo, hydroxy, trifluoromethyl, alkoxy of 1 to 4 carbons, —N(alkyl)$_2$, and $SO_2NH_2$ wherein alkyl is straight or branched chain of 1 to 4 carbons, and a phenyl ring substituted with a fused five membered ketal, i.e.

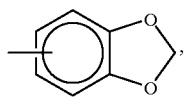

$R_9$, $R_{10}$, $R_{11}$, $R_{12}$, $R_{13}$, $R_{15}$, $R_{16}$ and $R_{19}$ are independently selected from the group consisting of hydrogen, straight or branched chain alkyl of 1 to 4 carbons, phenyl, subsituted phenyl and —$A_1$-phenyl.

$A_3$ is a direct bond, an alkylene bridge of 1 to 6 carbons, or

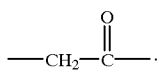

is a 5 to 7 membered heterocyclo ring which can contain an additional nitrogen atom or can contain an oxygen or sulfur atom.

$R_{21}$ is attached to an available carbon or nitrogen atom and is hydrogen, straight or branched chain alkyl of 1 to 4 carbons, hydroxy or amino.

$R_{22}$ is attached to an available carbon or nitrogen atom and is keto, —(C=O)$R_{23}$, —CO$_2$$R_{23}$, —NH—(C=O)—$R_{23}$, —N(alkyl)$_2$, —$A_1$-hydroxy, —$A_1$—N($R_9$)($R_{10}$), —$A_1$-alkoxy, —$A_2$-phenyl, —$A_2$-substituted phenyl, or —$A_2$-heteroaryl wherein alkyl is straight or branched chain of 1 to 4 carbons and alkoxy is such an alkyl bonded through an oxygen.

n is one or two.

m is zero or one.

$R_{23}$ is alkyl, —N($R_9$)($R_{10}$), or —$A_2$-heteroaryl wherein alkyl is straight or branched chain of 1 to 4 carbons.

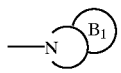

represents a fused bicyclic ring wherein the monocyclic ring

is defined previously and

represents a substituted phenyl having two carbon atoms in common with the monocyclic ring

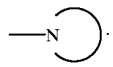

represents a spiro ring wherein the monocyclic ring

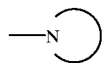

is defined previously and

represents a heterocyclo ring having a common carbon with the monocyclic ring

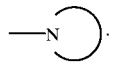

Also preferred is the method of treating a cGMP-associated condition, particularly erectile dysfunction, with the preferred compounds of formulas I and II as defined above or with a compound of formula III wherein:

Y, Z, $E_2$, $R_4$ and $R_3$ are as defined for the preferred compounds of formula II, and

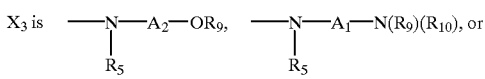

$R_5$, $A_1$ $A_2$, $R_9$, $R_{10}$, and

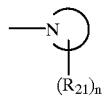

are as defined for the preferred compounds of formula II.

More Preferred Compounds and Method

The following compounds of formula I and II are more preferred:

Y is nitrogen.
Z is CH.
$R_3$ is ethyl.
$R_4$ is hydrogen.

$E_1$ is

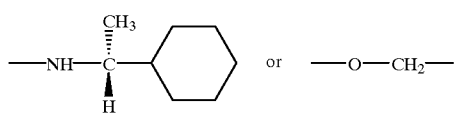 or —O—CH$_2$— disubstituted phenyl.

$E_2$ is —NH—CH$_2$-disubstituted phenyl.

The term "disubstituted phenyl" refers to a phenyl ring having two substituents independently selected from halogen and methoxy or wherein said disubstituted phenyl is 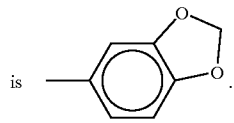.

$X_1$ is —O—$A_1$-heterocyclo, —O—$A_1$-heteroaryl, —NH—$A_2$—$R_2$, or 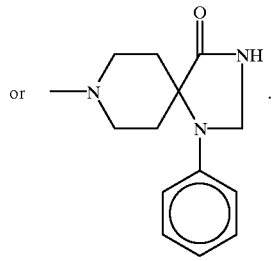.

$X_2$ is —O—$A_1$-heterocyclo, —O—$A_1$-heteroaryl, —NH—$A_2$—$R_{25}$, or 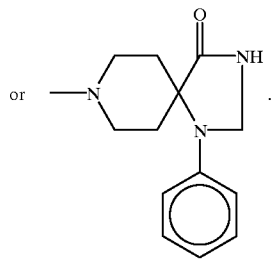.

$A_1$, $A_2$, $R_2$, $R_{25}$, "heterocyclo" and "heteroaryl" are as defined in the preferred definitions.

Also more preferred is the method of treating a CGMP associated condition, particularly erectile dysfunction, with the more preferred compounds of formula I and II as defined above or with a compound of formula III wherein:

Y, Z, $E_2$, $R_4$ and $R_3$ are as defined for the preferred compounds of formula II, and $X_3$ is —NH—$A_2$—$OR_9$ wherein $A_2$ and $R_9$ are as defined for the preferred compounds of formula II.

Most Preferred Compounds and Method

The following compounds of formulas I and II are most preferred:

Y is nitrogen.

Z is CH.

$F_3$ is ethyl.

$R_4$ is hydrogen.

$E_1$ is 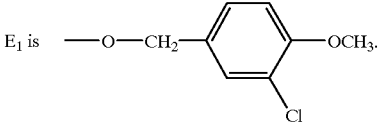

$E_2$ is 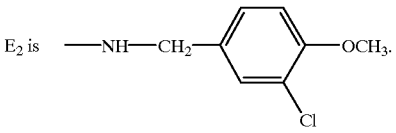

$X_1$ and $X_2$ are independently selected from the group consisting of

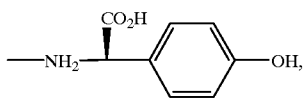

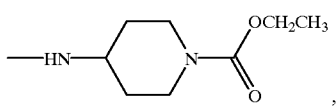

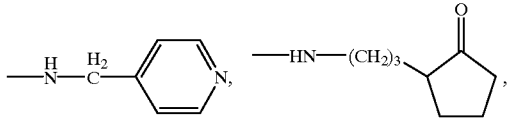

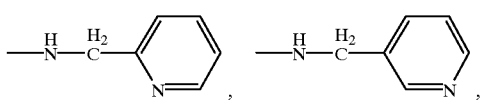

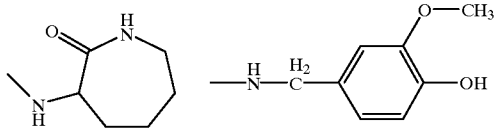

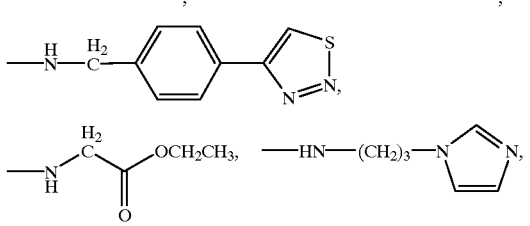

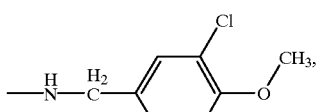

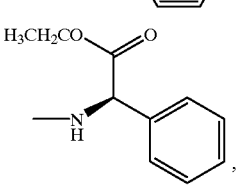

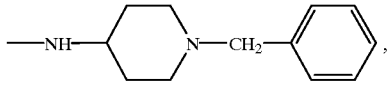

-continued

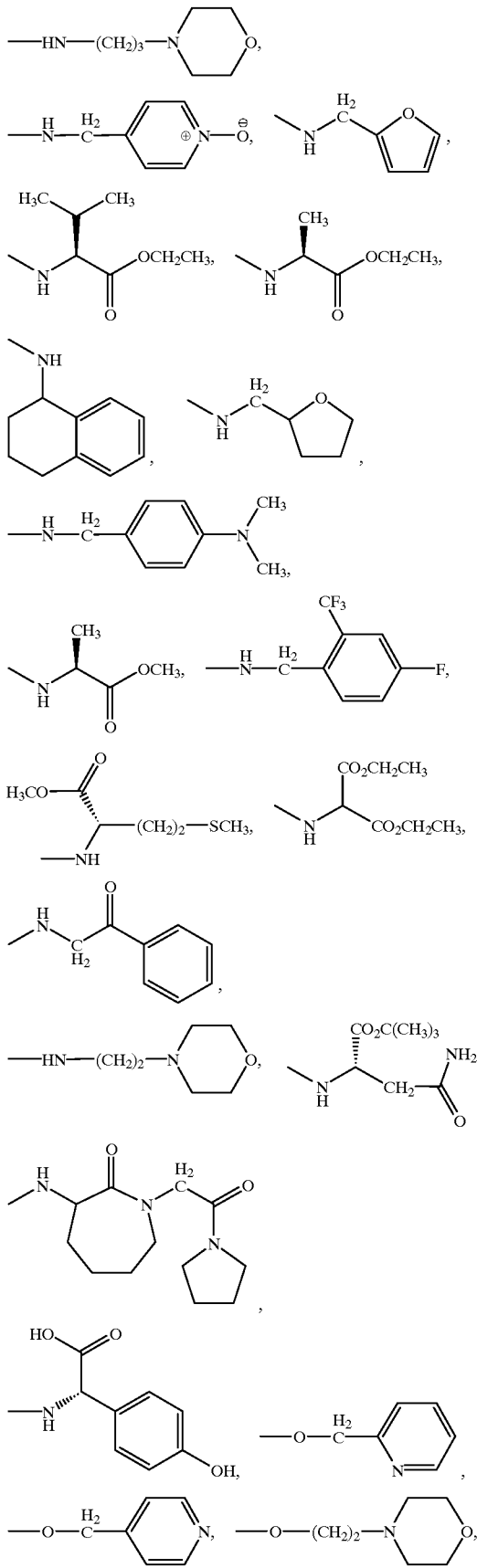

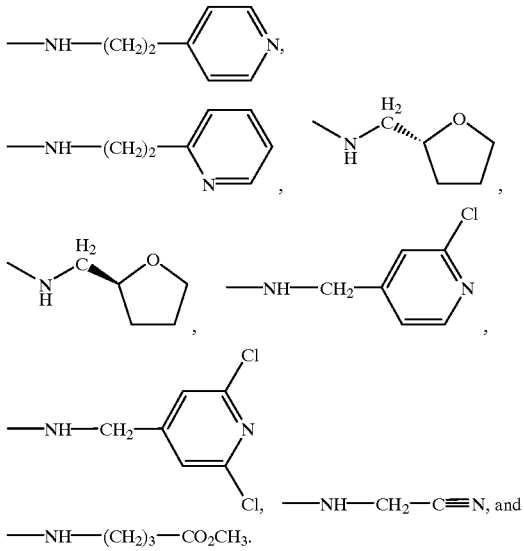

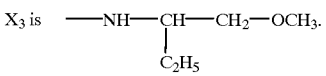

Also most preferred is the method of treating a cGMP associated condition, particularly erectile dysfunction, with the most preferred compounds of formulas I and II as defined above or with a compound of formula III wherein:

Y, Z, $E_2$, $R_4$ and $R_3$ are as defined the most preferred compounds of formula II, and $X_3$ is —NH—CH(C$_2$H$_5$)—CH$_2$—OCH$_3$.

Utility

The compounds of the present invention inhibit cGMP PDE, and in particular are potent and selective inhibitors of CGMP PDE V. The present compounds are useful in the treatment of cGMP-associated conditions. A "cGMP-associated condition", as used herein, denotes a disorder which can be treated by inhibiting cGMP PDE or elevating the level of cGMP in a subject, wherein treatment comprises prevention, partial alleviation or cure of the disorder. Inhibition of cGMP PDE or elevation of the cGMP level may occur locally, for example, within certain tissues of the subject, or more extensively throughout a subject being treated for such a disorder. Treatment may be facilitated wherein elevation of the cGMP level potentiates additional beneficial therapeutic effects, such as where elevation of the cGMP level potentiates the effects of endothelium-derived relaxing factor.

The compounds of the present invention are useful for the treatment of a variety of cardiovascular diseases including, but not limited to, hypertension, angina (stable, unstable, and variant), (congestive) heart failure, restenosis, atherosclerosis, and dyslipidemia, as well as reduced blood vessel patency, thrombus, both venous and arterial, myocardial infarction, peripheral vascular disease, stroke, bronchitis, chronic asthma, allergic asthma, allergic rhinitis, glaucoma, diseases characterized by disorders of gut motility, and forms of cancer responsive to the inhibition of cGMP PDE. In addition, these compounds are useful in the treatment of sexual dysfunction in both men (erectile dysfunction, for example, due to diabetes mellitus, spinal cord injury, radical prostatectomy, psychogenic etiology or any other cause) and women by improving blood flow to the genitalia, especially, the corpus cavernosum.

The present invention thus provides methods for the treatment of cGMP-associated conditions, comprising the step of administering to a subject in need thereof at least one compound of formulas I, II or III in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of formulas I, II or III capable of treating a cGMP-associated condition in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formulas I, II and III may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formulas I, II and III may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (Avicel®) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez®), and agents to control release such as polyacrylic copolymer (e.g., Carbopol® 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable nontoxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses and the like, subject to cGMP-associated conditions.

The compounds of the present invention may be employed alone or in combination with each other and/or other suitable therapeutic agents useful in the treatment of cGMP-associated conditions such as other cGMP PDE inhibitors, particularly other cGMP PDE V inhibitors, prostanoids, α-adrenergic agonists, endothelin antagonists, angiotensin II (especially, subtype $AT_1$) antagonists, angiotensin converting enzyme (ACE) inhibitors, renin inhibitors, and serotonin ($5-HT_{2c}$) agonists.

Exemplary such other therapeutic agents include the following: phentolamine, yohimbine, papaverine, apomorphine, sildenafil (see *Drugs of the Future*, 22, 138–143 (1997)), pyrazolopyrimidinones as described in U.S. Pat. Nos. 5,272,147; 5,250,534; 5,426,107; and 5,346,901, quinazolinones as described in U.S. Pat. No. 5,482,941; $AT_1$ antagonists selected from losartan, irbesartan, valsartan and candesartan; $ET_A$ antagonists selected from bosentan, ABT-627, and those described in U.S. Pat. No. 5,612,359 and U.S. patent application Ser. No. 60/035,832, filed Jan.

30, 1997; PDE V inhibitors selected from imidazoquinazolines (see WO 98/08848), carbazoles (see WO 97/03675, WO 97/03985 and WO 95/19978), imidazopurinones (see WO 97/19947), benzimidazoles (see WO 97/24334), pyrazoloquinolines (see U.S. Pat. No. 5,488,055), anthranilic acid derivatives (see WO 95/18097), fused heterocycles (see WO 98/07430) and thienopyrimidines (see DE 19632423); and 5-HT$_{2C}$ agonists selected from indoles (see *J. Med. Chem.*, 40, 2762–2769 (1997), EP 655440 and EP 657426).

The above other therapeutic agents, when employed in combination with the compounds of the present invention, may be used, for example, in those amounts indicated in the Physicians' Desk Reference (PDR) or as otherwise determined by one of ordinary skill in the art.

The following assay can be employed in ascertaining the degree of activity of a compound as a cGMP PDE inhibitor. Compounds described in the following Examples have been tested in this assay, and have shown activity.

PDE Scintillation Proximity Assay Protocol

Sonicated human platelet homogenates are prepared by the method of Seiler, et al. (Seiler, S., Gillespie, E., Arnold, A. J., Brassard, C. L., Meanwell, N. A. and Fleming, J. S., "Imidazoquinoline derivatives: potent inhibitors of platelet cAMP phosphodiesterase which elevate cAMP levels and activate protein kinase in platelets," *Thrombosis Research*, 62: 31–42 (1991)). PDE V is abundant in human platelets, and accounts for approximately 90% of the cGMP hydrolytic activity in the homogenates. When necessary, PDE V can be resolved from other PDE activities in the homogenates by anion exchange chromatography on a fast protein liquid chromatography system (FPLC) using a Mono-Q anion exchange column (Pharmacia) eluted with a linear gradient of 10 mM–450 mM NaCl.

The phosphodiesterase activity is assayed using a commercially available phosphodiesterase [$^3$H]cGMP scintillation proximity (SPA) assay kit (Amersham). The manufacturer's protocol is followed explicitly except that the reactions are carried out at room temperature and 3 mM nonradioactive cGMP is included in the suspension of SPA beads to prevent the synthesis of any additional radioactive products.

All documents cited in the present specification are incorporated herein by reference in their entirety.

The following Examples illustrate embodiments of the present invention, and are not intended to limit the scope of the claims.

ABBREVIATIONS

DMF=dimethylformamide
DMSO=dimethylsulfoxide
Et=ethyl
HPLC=high pressure liquid chromatography
LRMS=low resolution mass spectrometry
Me=methyl
MeOH=methanol
mp=melting point
THF=tetrahydrofuran
tlc=thin layer chromatography
rt=room temperature
h=hours
H$_2$=water
POCl$_3$=phosphorus oxychloride
EtOH=ethanol
H$_3$PO$_4$=phosphoric acid
HCl=hydrogen chloride
NaOH=sodium hydroxide
min=minutes Et$_3$N=triethylamine
Et$_2$O=ethyl ether
EtOAc=ethyl acetate
NaHCO$_3$=sodium bicarbonate
MgSO$_4$=magnesium sulfate
CH$_2$Cl$_2$=methylene chloride
Na$_2$SO$_4$=sodium sulfate
K$_2$CO$_3$=potassium carbonate

PREPARATION OF STARTING MATERIALS

Preparation 1

Preparation of (1-Ethylpyrazol-5-yl-amino)methylenemalonate diethyl ester

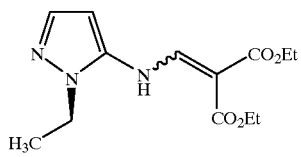

A neat solution of 5-amino-1-ethylpyrazole (20.0 g, 180 mmol) and diethyl ethoxymethylenemalonate (42.8 g, 198 mmol) was heated at 120° C. for 5 h. This material was used directly without further purification. If needed, the product can be distilled at 154–160° C. (0.1 mm Hg) to afford the title compound as a liquid which solidified to afford the title compound as a pale colored solid: mp 50–53° C.

Preparation 2

Preparation of 1-Ethyl-4-hydroxy-1H-pyrazolo[3,4-b]pyridine-5-carboxylic acid ethyl ester

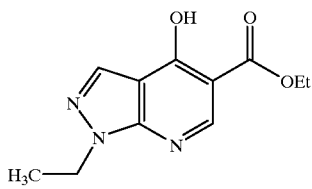

(1-Ethylpyrazol-5-yl-amino)methylenemalonate diethyl ester (180 mmol from previous reaction) was dissolved in diphenyl ether (200 mL), and the resulting solution was placed in a preheated oil bath at 255° C. The reaction solution was heated for 5 h, and then the diphenyl ether was removed via distillation. The resulting brown reaction mixture was cooled to room temperature and poured to hexane (1 L). Cooling this solution to −78° C., followed by filtration of the resulting precipitate afforded the title compound as a beige colored needle shaped solid that was >90% pure by HPLC and was used directly (25 g, 60% for 2 steps). A portion was recrystallized using ethanol-H$_2$O to afford a white solid: mp 85–86° C.; LRMS (m/z) 236 (MH$^+$).

Preparation 3

Preparation of 4-Chloro-1-ethyl-1H-pyrazolo[3,4-b]pyridine-5-carboxylic acid ethyl ester

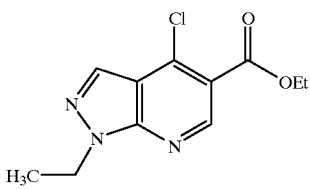

1-Ethyl-4-hydroxy-1H-pyrazolo[3,4-b]pyridine-5-carboxylic acid ethyl ester (15 g, 63.8 mmol) was dissolved in $POCl_3$ (100 mL), and the resulting solution was heated at reflux for 4 h. The remaining $POCl_3$ was removed via evaporation under reduced pressure. The residual light brown solid was recrystallized from EtOH-hexane to afford the title compound as a white solid (14 g, 55.3 mmol, 87%): HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.84 minutes showed a purity of 96%; LRMS (m/z) 254 ($MH^+$).

Preparation 4

Preparation of 4-Chloro-1-ethyl-1H-pyrazolo[3,4-b]pyridine-5-carboxylic acid ethyl ester

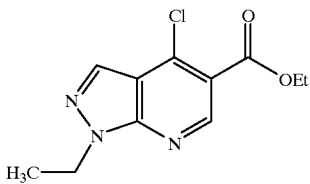

(1-Ethylpyrazol-5-yl-amino)methylenemalonate diethyl ester (10.0 g, 42.6 mmol) was dissolved in 50 mL $POCl_3$. This solution was heated at reflux for 10 h before the $POCl_3$ was removed under reduced pressure. The resulting brown residue was diluted with 5 mL EtOH and extracted with hot hexane (200 mL×3). The combined organic layers were evaporated under reduced pressure to afford the title compounds which formed light green needle shaped crystals upon standing at room temperature (5.4 g, 21.3 mmol, 50% yield). This material is identical to the one obtained in Preparation 3 ($^1H$ NMR, $^{13}C$ NMR, MS, and HPLC).

Preparation 5

(3-Chloro-4-methoxyphenyl)methylamine hydrogen chloride

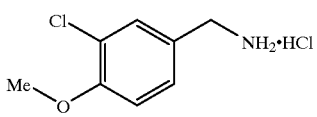

(4-Methoxyphenyl)methylamine (75.0 g, 0.55 mol) was dissolved in 400 mL diethyl ether. Hydrogen chloride (4.0 M in dioxane, 1.1 mol) was added dropwise with vigorous stirring. After the addition completed, the white solid was filtered and washed thoroughly with diethyl ether. The solid was air dried over night (95.0 g, 100%).

Chlorine gas was bubbled into 400 mL glacial acetic acid with stirring until the weight gained equaled 7% of the starting acetic acid. In a 2 L round bottom flask, 4-methoxybenzylamine hydrogen chloride (32.0 g, 0.18 mol) was suspended in 400 mL glacial acetic acid with vigorous stirring. The chlorine solution (1.5 eq $Cl_2$) was added in rapid drops in 30 min at room temperature. The resulted suspension was stirred for another 20 min before $N_2$ was bubbled in to remove $Cl_2$ and HCl into a 6 N NaOH trap. The acetic acid was evaporated under reduced pressure to 100 mL. To this white slurry, diethyl ether (300 mL) was used to loosen the solid which was then filtered. The solid was resuspended with 50 mL acetic acid followed by the addition of 50 mL diethyl ether and filtration. This process was repeated twice. The white solid was transferred to a 1 L Erlenmeyer flask and suspended in 400 mL THF. This suspension was heated to boiling for 10 min before filtration. The undissolved solid was filtered, and twice resuspended in boiling THF (100 mL) with filtration to afford the title compound (27.0 g, 71%) as a white solid. This material contained <2% starting material and <2% dichlorinated material.

Preparation 6

General Procedure to Prepare 4-Aminopyrazolopyridine-5-carboxylic acids

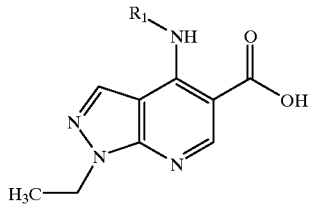

The appropriate 4-chloro-1H-pyrazolo[3,4-b]pyridine-5-carboxylic acid ethyl ester (4.0 mmol) and the appropriate amine (4.4 mmol)) were suspended in EtOH (20 mL). To this suspension was added of $Et_3N$ (2.8 mL, 20 mmol), and the resulting solution was heated at reflux for 10 h. To the resulting suspension was added 6 N NaOH (2.7 mL, 16 mmol), and the resulting mixture was heated at reflux for 3 h. EtOH was then removed via evaporation under reduced pressure, and the residual white solid was dissolved in 25 mL 0.1 N NaOH. The resulting aqueous mixture was extracted with diethyl ether (3×150 mL), and the organic extracts were discarded. The aqueous layer was acidified with 1 N HCl, and the resulting white precipitate was collected by filtration and washed sequentially with 1 N HCl, $H_2O$, EtOH and $Et_2O$ to afford the desired 4-aminopyrazolopyridine.

Using the above described procedure, the following compounds were prepared:

A. 4-[[(3-Chloro-4-methoxyphenyl)methyl]amino]-1-ethyl-1H-pyrazolo[3,4-b]pyridine-5-carboxylic acid

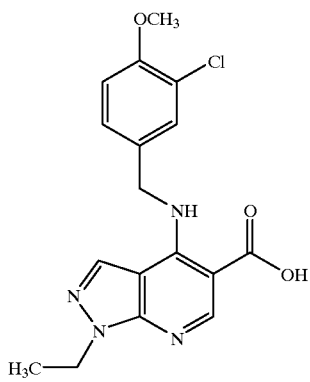

4-Chloro-1-ethyl-1H-pyrazolo[3,4-b]pyridine-5-carboxylic acid ethyl ester and (3-chloro-4-methoxyphenyl)methylamine was used to afford the title compound (87%) as a white solid: mp 250 ° C.(decomposed).

B. (R)-4-[(1-Cyclohexylethyl)amino]-1-ethyl-1H-pyrazolo[3,4-b]pyridine-5-carboxylic acid

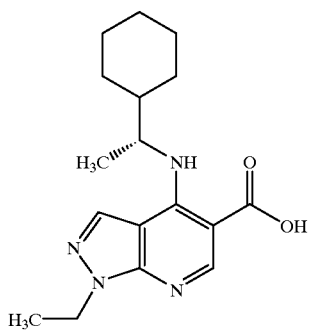

4-Chloro-1-ethyl-1H-pyrazolo[3,4-b]pyridine-5-carboxylic acid ethyl ester and (R)-2-cyclohexylethylamine was used to afford the title compound (80%) as a white solid: mp 200° C. (decomposed).

C. 4-[[(3,4-Dioxomethylenephenyl)methyl]amino]-1-ethyl-1H-pyrazolo[3,4-b]pyridine-5-carboxylic acid

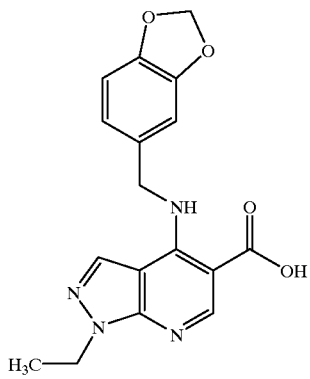

4-Chloro-1-ethyl-1H-pyrazolo[3,4-b]pyridine-5-carboxylic acid ethyl ester and (3,4-dioxomethylenephenyl)methylamine were used to afford the title compound (80%) as a white solid: mp 230° C. (decomposed).

Preparation 7

(R)-4-[(1-Cyclohexylethyl)amino]-1-ethyl-1H-pyrazolo[3,4-b]pyridine-5-carboxylic acid pentafluorophenyl ester

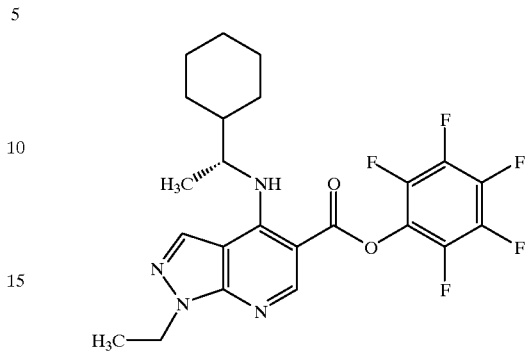

The (R)-4-[(1-Cyclohexylethyl)amino]-1-ethyl-1H-pyrazolo[3,4-b]pyridine-5-carboxylic acid (0.3 g, 0.95 mmol) was suspended in 2 mL DMF with the subsequent addition of pyridine (0.15 g, 1.9 mmol), pentofluorophenol trifluoroacetate (0.53 g, 1.9 mmol), and a catalytic amount of pentafluorophenol (10 mg). This mixture was stirred at rt for 48 h, and the resulting mixture was diluted with EtOAc (50 mL) and washed with 0.1 N HCl (50 mL), 5% NaHCO$_3$ (3×50 mL), and brine (5×50 mL). The organic extract was dried over MgSO$_4$ and concentrated to afford the title compound as a viscous oil (0.44 g, 95%): HPLC (YMC S5 ODS 4.6×50 mm column, 4 minute gradient-50% B to 100% B, 4.0 mL/min flow, solvent A: 10% MeOH-90% H$_2$O-0.2% H$_3$PO$_4$, solvent B: 90% MeOH-10% H$_2$O-0.2% H$_3$PO$_4$) retention time 5.06 minutes showed a purity of 95%; LRMS (m/z) 483 (MH$^+$).

The resulting product contained ~5% free pentafluorophenol and was used directly in subsequent reactions.

Preparation 8

Preparation of 1-Ethyl-4-hydroxy-1H-pyrazolo[3,4-b]pyridine-5-carboxylic acid

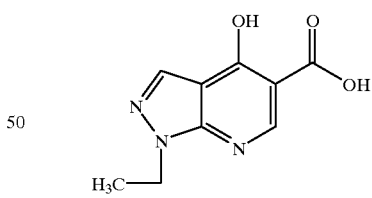

1-Ethyl-4-hydroxy-1H-pyrazolo[3,4-b]pyridine-5-carboxylic acid ethyl ester (10.0 g, 42.6 mmol) was suspended in 50 mL EtOH. To this suspension was added 6 N NaOH (21.3 mL, 3 eq). The resulting light brown solution was heated at reflux for 3 hr before being diluted with 100 mL water. The aqueous solution was extracted with diethyl ether (50 mL×3) and the organic layer was discarded. The aqueous layer was acidified with 1 N HCl and a white precipitate formed. The title compound was collected by filtration and rinsed with water and diethyl ether affording a white solid (7.9 g, 90%): mp 218° C. (decomposed); LRMS (m/z) 208 (MH$^+$).

Preparation 9

4-Chloro-1-ethyl-1H-pyrazolo[3,4-b]pyridine-5-carboxylic acid chloride

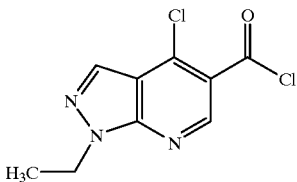

1-Ethyl4-hydroxy-1H-pyrazolo[3,4-b]pyridine-5-carboxylic acid (0.92 g, 4.4 mmol) was dissolved in 10 mL POCl$_3$, and the solution was heated at reflux for 2 hr. The excess POCl$_3$ was removed under reduced pressure and azeotroped three times with toluene. The brown residue was dissolved in 20 mL CH$_2$Cl$_2$, Et$_3$N (5 eq) and an amine such as 4-aminomethylpyridine (1.2 eq) were then added sequentially. The resulting solution was stirred at rt for 2 h before being diluted with 100 mL water. The organic layer was separated and the aqueous layer was extracted with CH$_2$Cl$_2$ (50 mL×3). The combined organic layer was washed with NaHCO$_3$ and water. The organic layer was dried over Na$_2$SO$_4$ and the solvent was removed. The residue was chromatographed using silica gel column (5% MeOH—CH$_2$Cl$_2$) to afford the title compound as a white solid (0.6 g, 44%).

EXAMPLE 1

General Procedures for the Preparation of 4-Aminopyrazolopyridines-5-carboxylates and 4-Aminopyrazolopyridines-5-carboxamides

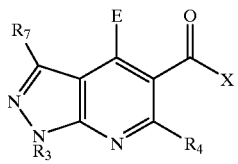

X is X$_1$, X$_2$ or X$_3$
E is E$_1$ (other than
—OR$_1$ or —S—R$_1$)
or E$_2$.

Method A

To a mixture of the appropriate 4-amino pyrazolopyridine-5-carboxylic acid (5.6 mmol), 1-[3-(dimethylamino)propyl]-3-ethylcarbodiimide hydrochloride (EDAC. HCl, 1.6 g, 8.4 mmol), and 1-hydroxybenzotriazole (1.1 g, 8.4 mmol) in anhydrous THF (50 mL) was added triethylamine (4.0 mL, 28.0 mmol), and the resulting solution was stirred at rt for 10 min. To the resulting reaction solution was then added the appropriate amine or alcohol of the formula X—H (6.7 mmol, 1.2 eq), and this solution was stirred at rt for 24 h. The resulting reaction solution was concentrated via evaporation under reduced pressure, and the residual solid was resuspended in EtOAc (250 mL). This EtOAc suspension was washed with H$_2$O (200 mL), NaOH (0.1 N, 2×200 mL), potassium phosphate buffer (50 mM, pH 7, 2×200 mL) and H$_2$O (200 mL). The organic layer was then dried over anhydrous Na$_2$SO$_4$ and concentrated via evaporation under reduced pressure until a solid began to precipitate. This mixture was allowed to stand at rt, and the precipitated solid was collected and washed thoroughly with Et$_2$O and once with 50% Et$_2$O-EtOAc to afford the appropriate title compound as a solid. A second crop may be obtained from the mother liquors. If a solid is not obtained by this method, then purification of the extraction residue via column chromatography using silica gel and elution with 5% CH$_2$Cl$_2$—CH$_3$OH afforded the appropriate title compound.

Method B

The appropriate 4-amino pyrazolopyridine-5-carboxylic acid (2.8 mmol) was suspended in anhydrous CH$_2$Cl$_2$ (20 mL), and oxalyl chloride (0.72 mL, 8.4 mmol) was added to this mixture followed by 2 drops of DMF. The resulting suspension was stirred at rt for 1 h after the suspension cleared. The resulting reaction solution was evaporated under reduced pressure, and the residue was redissolved in anhydrous CH$_2$Cl$_2$ (20 mL). To this solution was added sequentially Et$_3$N (1.9 mL, 14.0 mmol) and then the appropriate amine or alcohol of the formula X—H (4.2 mmol). The solution was stirred at rt for 2 hr. The solvent was removed and the resulted residue was suspended in 100 mL EtOAc. The organic was subsequently washed with water, 1 N NaOH, and 1 N HCl. The organic layer was then dried over anhydrous Na$_2$SO$_4$ and concentrated via evaporation under reduced pressure. The resulted crude products have been purified by either crystallization (>100 mg scale) or preparative HPLC (<100 mg scale).

Method C

The appropriate 4-amino-1-ethyl-1H-pyrazolo[3,4-b]pyridine-5-carboxylic acid pentafluorophenyl ester (0.16 mmol) was dissolved in anhydrous THF (2 mL) and triethylamine (49 mg, 0.48 mmol). The appropriate amine or alcohol of the formula X—H (0.32 mmol, 2.0 eq) was then added, and the reaction solution was stirred at rt for 12 h. The resulting reaction solution was diluted with EtOAc (5 mL), and the organic layer was washed with 0.1 N NaOH (5 mL), potassium phosphate buffer (pH 7) and brine. The organic layer was then dried over anhydrous Na$_2$SO$_4$ and concentrated via evaporation under reduced pressure to afford the title compound. Purification of the crude product if necessary can be accomplished by either crystallization or preparative HPLC.

Compounds listed in the following Tables prepared by these procedures are denoted as methods 1A, 1B, or 1C.

EXAMPLE 2

General Procedure for the Preparation of 4-Aminopyrazolopyridines-5-carboxylates and 4-Aminopyrazolopyridines-5-carboxamides

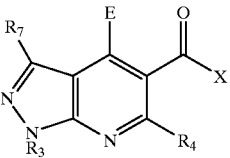

X is X$_1$, X$_2$ or X$_3$
E is E$_1$ (other than
—OR$_1$ or —S—R$_1$)
or E$_2$

To a solution of the appropriate 4-chloro-1H-pyrazolo[3,4-b]pyridine-5-carboxylic acid chloride (4.4 mmol) in CH$_2$Cl$_2$ was added the appropriate amine or alcohol of the formula X—H (6.6 mmol) and Et$_3$N (22.0 mmol) at 0° C. The reaction was stirred from 0° C. to rt until completion. The solvent was removed via evaporation under reduced pressure, and the residue was purified by silica gel chromatography.

To a solution of the resulting 4-chloropyrazolopyridines-5-carboxamide or ester (0.21 mmol) in ethanol (5 mL) was added an appropriate amine of the formula E—H (0.24 mmol) and Et₃N (1.4 mmol). The solution was heated at reflux for 2 hr before being diluted with CH₂Cl₂. The organic layer was sequentially washed with 1N HCl, and water, dried, and evaporated under reduced pressure. The residue was purified by silica gel chromatography to afford the title compound.

Compounds listed in the following Tables prepared by this procedure are denoted as method 2.

EXAMPLE 3

General Procedure for the Preparation of 4-Oxypyrazolopyridines-5-carboxylates and 4-Oxypyrazolopyridines-5-carboxamides

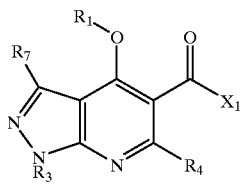

To a solution of the appropriate 4-chloro-1H-pyrazolo[3,4-b]pyridine-5-carboxylic acid chloride (4.4 mmol) in CH₂Cl₂ was added the appropriate amine or alcohol of the formula X₁—H (6.6 mmol) and Et₃N (22.0 mmol) at 0° C. The reaction was stirred from 0° C. to rt until completion. The solvent was removed via evaporation under reduced pressure, and the residue was purified by silica gel chromatography.

To a solution of the resulting 4-chloropyrazolopyridine-5-carboxamide or ester (0.21 mmol) in DMF (2 mL) was added an appropriate alcohol of the formula R₁—OH (0.24 mmol) and K₂CO₃ (0.42 mmol). The mixture was stirred at 50° C. for 2 hr before being diluted with CH₂Cl₂. The organic layer was sequentially washed with 1N HCl, and water, dried, and evaporated under reduced pressure. The residue was purified by silica gel chromatography to afford the title compound.

Compounds listed in the following Tables prepared by this procedure are denoted as method 3.

EXAMPLE 4

General Procedure for the Preparation of 4-Thiopyrazolopyridines-5-carboxylates and 4-Thiopyrazolopyridines-5-carboxamides

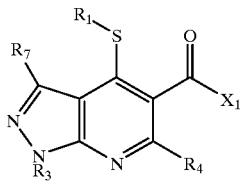

To a solution of the appropriate 4-chloro-1H-pyrazolo[3,4-b]pyridine-5-carboxylic acid chloride (4.4 mmol) in CH₂Cl₂ was added the appropriate amine or alcohol of the formula X₁—H (6.6 mmol) and Et₃N (22.0 mmol) at 0° C. The reaction was stirred from 0° C. to rt until completion. The solvent was removed via evaporation under reduced pressure, and the residue was purified by silica gel chromatography.

To a solution of the resulting 4-chloropyrazolopyridine-5-carboxamide or ester (0.21 mmol) in DMF (2 mL) was added an appropriate thiol of the formula R₁—SH (0.24 mmol) and K₂CO₃ (0.42 mmol). The mixture was stirred at 50° C. for 2 hr before being diluted with CH₂Cl₂. The organic layer was sequentially washed with 1N HCl, and water, dried, and evaporated under reduced pressure. The residue was purified by silica gel chromatography to afford the title compound.

EXAMPLE 5

Preparation of 4-[[(3-Chloro4-methoxyphenyl)methyl]amino]-1-ethyl-N-(4-pyridinylmethyl)-1H-pyrazolo[3,4-b]pyridine-5-carboxamide

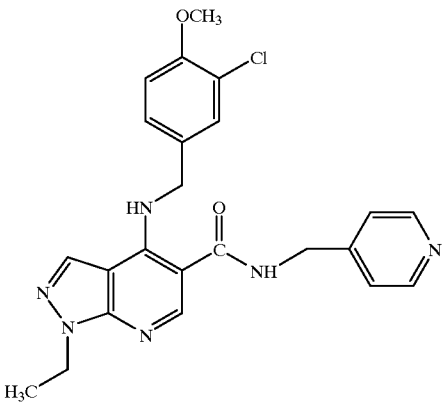

Using the procedure of method 1A, triethylamine (4.0 ml, 28.0 mmol) was added to a mixture of 4-[[(3-chloro-4-methoxyphenyl)methyl]amino]-1-ethyl-1H-pyrazolo[3,4-b]pyridine-5-carboxylic acid (2.0 g, 5.6 mmol), 1-[3-(dimethylamino)propyl]-3-ethylcarbodiimide hydrochloride (EDAC.HCl, 1.6 g, 8.4 mmol), and 1-hydroxybenzotriazole (1.1 g, 8.4 mmol) in anhydrous THF (50 ml). The resulting solution was stirred at rt for 10 min. To the resulting reaction solution was then added 4-aminomethylpyridine (0.72 g, 6.7 mmol) and this solution was stirred at rt for 24 h. The resulting reaction solution was concentrated via evaporation under reduced pressure, and the residual solid was resuspended in EtOAc (250 mL). This EtOAc suspension was washed with H₂O (200 ml), NaOH (0.1 N, 2×200 ml), potassium phosphate buffer (50 mM, pH 7, 2×200 ml) and H₂O (200 mL). The organic layer was then dried over anhydrous Na₂SO₄ and concentrated via evaporation under reduced pressure until a solid began to precipitate. This mixture was allowed to stand at rt, and the precipitated solid was collected and washed thoroughly with Et₂O and once with 50% Et₂O-EtOAc to afford a white solid (2.2 g, 90%): mp: 209–210.5 C; LRMS (m/z) 450; ¹³C NMR (CDCl₃): δ 171.8, 156.4, 153.7, 153.1, 151.7, 150.8, 150.5, 135.7, 132.0, 130.5, 128.3, 124.5, 124.3, 114.2, 105.6, 104.4, 57.4, 49.8, 43.7, 43.6, 15.9. Anal. Calc'd for C₂₃H₂₃ClN₆O₂: C, 61.26; H, 5.14; N, 18.64; Cl, 7.86. Found: C, 61.03; H, 5.22; N, 18.66; Cl, 8.02.

TABLE

The following compounds of formula I were prepared wherein R₃ is ethyl, R₄ is hydrogen, Y is nitrogen, Z is CH, and E₁ is

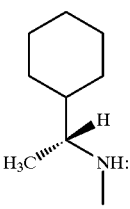

| Ex | Name | X₁ | PURITY (%) | HPLC (retention time, minutes) | OTHER DATA |
|---|---|---|---|---|---|
| 6 | (R)-4-[(1-Cyclohexylethyl)amino]-1-ethyl-N-[1-(phenylmethyl)-4-piperidinylmethyl]-1H-pyrazolo[3,4-b]pyridine-5-carboxamide | (METHOD 1C) | 100 | 3.47 | m/z (M + H) 489 |
| 7 | (R)-4-[(1-Cyclohexylmethyl)amino]-1-ethyl-N-(3-pyridinylmethyl)-1H-pyrazolo[3,4-b]pyridine-5-carboxamide | (METHOD 1C) | 96 | 3.28 | m/z (M + H) 407 |
| 8 | (R)-4-[(1-Cyclohexylethyl)amino]-N-(2,3-dihydro-1H-indan-2-yl)-1-ethyl-1H-pyrazolo[3,4-b]pyridine-5-carboxamide | (METHOD 1C) | 91 | 4.53 | m/z (M + H) 432 |
| 9 | (R)-4-[(1-Cyclohexylethyl)amino]-1-ethyl-N-[(4-hydroxy-3-methoxyphenyl)methyl]-1H-pyrazolo[3,4-b]pyridine-5-carboxamide | (METHOD 1C) | 91 | 3.91 | m/z (M + H) 452 |
| 10 | (1R)-4-[(1-Cyclohexylethyl)amino]-N-[(2,3-dihydro-1,4-benzodioxin-2-yl)methyl]-1-ethyl-1H-pyrazolo[3,4-b]pyridine-5-carboxamide | (METHOD 1C) | 93 | 4.56 | m/z (M + H) 464 |
| 11 | (R)-N-(1H-Benzimidazol-2-ylmethyl)-4-[(1-cyclohexylethyl)amino]-1-ethyl-1H-pyrazolo[3,4-b]pyridine-5-carboxamide | (METHOD 1C) | 90 | 3.58 | m/z (M + H) 446 |
| 12 | (R)-4-[(1-Cyclohexylethyl)amino]-1-ethyl-N-[3-(2-oxo-1-pyrrolidinyl)propyl]-1H-pyrazolo[3,4-b]pyridine-5-carboxamide | (METHOD 1C) | 90 | 3.72 | m/z (M + H) 441 |

-continued

| Ex | Name | X$_1$ | PURITY (%) | HPLC (retention time, minutes) | OTHER DATA |
|---|---|---|---|---|---|
| 13 | (R)-4-[(1-Cyclohexylethyl)amino]-1-ethyl-N-[(5-methyl-2-furanyl)methyl]-1H-pyrazolo[3,4-b]pyridine-5-carboxamide | (METHOD 1C) | 94 | 4.28 | m/z (M + H) 410 |
| 14 | (R)-N-[(2-Chlorophenyl)methyl]-4-[(1-cyclohexylethyl)amino]-1-ethyl-1H-pyrazolo,4-b]pyridine-5-carboxamide | (METHOD 1C) | 93 | 4.52 | m/z (M + H) 440 |
| 15 | (1R)-4-[(1-Cyclohexylethyl)amino]-1-ethyl-N-[3-(2-methyl-1-piperidinyl)propyl]-1H-pyrazolo[3,4-b]pyridine-5-carboxamide | (METHOD 1C) | 88 | 3.25 | m/z (M + H) 455 |
| 16 | (R)-4-[(1-Cyclohexylethyl)amino]-1-ethyl-N-[2-(2-pyridinyl)ethyl]-1H-pyrazolo[3,4-b]pyridine-5-carboxamide | (METHOD 1C) | 88 | 3.19 | m/z (M + H) 421 |
| 17 | (1R)-4-[(1-Cyclohexylethyl)amino]-1-ethyl-N-(hexahydro-2-oxo-1H-azepin-3-yl)-1H-pyrazolo[3,4-b]pyridine-5-carboxamide | (METHOD 1C) | 84 | 3.84 | m/z (M + H) 427 |
| 18 | [R.(R*,R*)]-a-[[[4-[(1-Cyclohexylethyl)amino]-1-ethyl-1H-pyrazolo[3,4-b]pyridin-5-yl]carbonyl]amino]benzeneacetic acid ethyl ester | (METHOD 1C) | 93 | 4.43 | m/z (M + H) 478 |
| 19 | (R)-4-[(1-Cyclohexylethyl)amino]-1-ethyl-N-[2-(3-pyridinyl)ethyl]-1H-pyrazolo[3,4-b]pyridine-5-carboxamide | (METHOD 1C) | 93 | 3.20 | m/z (M + H) 420 |
| 20 | (R)-4-[(1-Cyclohexylethyl)amino]-1-ethyl-N-[[4-(1,2,3-thiadiazol-4-yl)phenyl]methyl]-1H-pyrazolo[3,4-b]pyridine-5-carboxamide | (METHOD 1C) | 85 | 4.26 | m/z (M + H) 490 |

-continued

| Ex | Name | X₁ | PURITY (%) | HPLC (retention time, minutes) | OTHER DATA |
|---|---|---|---|---|---|
| 21 | (R)-4-[(1-Cyclohexylethyl)amino]-1-ethyl-N-(2-thienylmethyl)-1H-pyrazolo[3,4-b]pyridine-5-carboxamide | 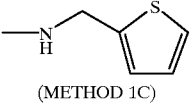 (METHOD 1C) | 93 | 4.27 | m/z (M + H) 412 |
| 22 | (1R)-N-(1-Azabicyclo[2.2.2]octan-3-yl)-4-[(1-cyclohexylethyl)amino]-1-ethyl-1H-pyrazolo[3,4-b]pyridine-5-carboxamide | 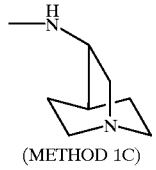 (METHOD 1C) | 85 | 3.21 | m/z (M + H) 425 |
| 23 | (R)4-[(1-Cyclohexylethyl)amino]-1-ethyl-N-(3-1H-imidazol-1-ylpropyl)-1H-pyrazolo[3,4-b]pyridine-5-carboxamide | 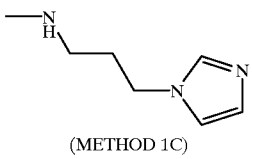 (METHOD 1C) | 94 | 3.11 | m/z (M + H) 424 |
| 24 | (R)-4-[[[4-[(1-Cyclohexylethyl)amino]-1-ethyl-1H-pyrazolo[3,4-b]pyridin-5-yl]carbonyl]amino]-piperidinecarboxylic acid ethyl ester | 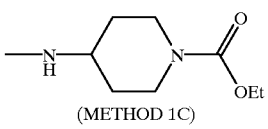 (METHOD 1C) | 90 | 4.23 | m/z (M + H) 471 |
| 25 | [1S-[1a(S*),2b]]-4-[(1-Cyclohexylethyl)amino]-1-ethyl-N-(2-phenylcyclopropyl)-1H-pyrazolo[3,4-b]pyridine-5-carboxamide | 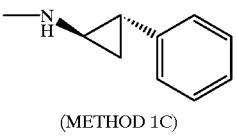 (METHOD 1C) | 95 | 4.54 | m/z (M + H) 432 |
| 26 | (R)-4-[(1-Cyclohexylethyl)amino]-N-[(2,6-difluorophenyl)methyl]-1-ethyl-1H-pyrazolo[3,4-b]pyridine-5-carboxamide | 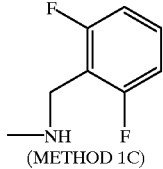 (METHOD 1C) | 93 | 4.3 | m/z (M + H) 441 |
| 27 | (R)-4-[(1-Cyclohexylethyl)amino]-1-ethyl-N-phenylmethyl)-1H-pyrazolo[3,4-b]pyridine-5-carboxamide | 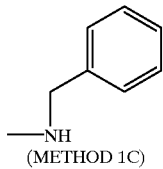 (METHOD 1C) | 95 | 4.33 | m/z (M + H) 406 |
| 28 | (R)-4-[(1-Cyclohexylethyl)amino]-N-[6-(dimethylamino)hexyl]-1-ethyl-1H-pyrazolo[3,4-b]pyridine-5-carboxamide | 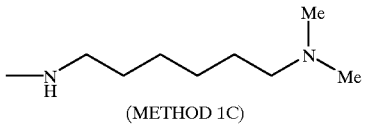 (METHOD 1C) | 84 | 3.29 | m/z (M + H) 443 |
| 29 | (R)-4-[(1-Cyclohexylethyl)amino]-1-ethyl-N-[2-(2-methoxyphenyl)ethyl]-1H-pyrazolo[3,4-b]pyridine-5-carboxamide | 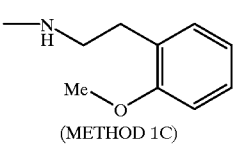 (METHOD 1C) | 91 | 4.45 | m/z (M + H) 449 |

-continued

| Ex | Name | X₁ | PURITY (%) | HPLC (retention time, minutes) | OTHER DATA |
|---|---|---|---|---|---|
| 30 | [R-(R*,R*)]-N-(1-Cyclohexylethyl)-4-[(1-cyclohexylethyl)amino]-1-ethyl-1H-pyrazolo[3,4-b]pyridine-5-carboxamide | 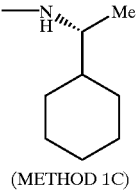 (METHOD 1C) | 92 | 4.66 | m/z (M + H) 426 |
| 31 | (R)-4-[(1-Cyclohexylethyl)amino]-1-ethyl-N-[2-(4-methoxyphenyl)ethyl]-1H-pyrazolo[3,4-b]pyridine-5-carboxamide | 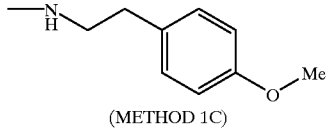 (METHOD 1C) | 95 | 4.38 | m/z (M + H) 449 |
| 32 | (R)-4-[(1-Cyclohexylethyl)amino]-1-ethyl-N-(4-hydroxybutyl)-1H-pyrazolo[3,4-b]pyridine-5-carboxamide |  (METHOD 1C) | 94 | 3.67 | m/z (M + H) 388 |
| 33 | (R)-4-[(1-Cyclohexylethyl)amino]-1-ethyl-N-[2-(5-methoxy-1H-indol-3-yl)ethyl]-1H-pyrazolo[3,4-b]pyridine-5-carboxamide | 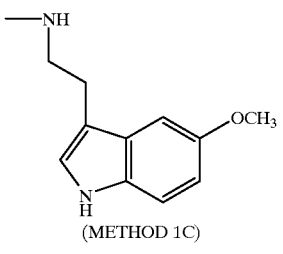 (METHOD 1C) | 88 | 4.18 | m/z (M + H) 488 |
| 34 | [1S-[1a,2a(S*),4a]]-N-(Bicyclo[2.2.1]heptan-2-yl)-4-[(1-cyclohexylethyl)amino]-1-ethyl-1H-pyrazolo[3,4-b]pyridine-5-carboxamide |  (METHOD 1C) | 88 | 4.47 | m/z (M + H) 410 |
| 35 | (R)-4-[(1-Cyclohexylethyl)amino]-1-ethyl-N-(2-pyridinylmethyl)-1H-pyrazolo[3,4-b]pyridine-5-carboxamide | 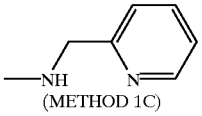 (METHOD 1C) | 98 | 3.42 | m/z (M + H) 407 |
| 36 | (R)-4-[(1-Cyclohexylethyl)amino]-1-ethyl-N-[(1-ethyl-2-pyrrolidinyl)methyl]-1H-pyrazolo[3,4-b]pyridine-5-carboxamide | 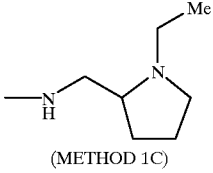 (METHOD 1C) | 84 | 3.28 | m/z (M + H) 427 |
| 37 | (R)-N-[2-(Acetylamino)ethyl]-4-[(1-cyclohexylethyl)amino]-1-ethyl-1H-pyrazolo[3,4-b]pyridine-5-carboxamide | 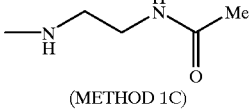 (METHOD 1C) | 93 | 3.52 | m/z (M + H) 401 |

-continued

| Ex | Name | X₁ | PURITY (%) | HPLC (retention time, minutes) | OTHER DATA |
|---|---|---|---|---|---|
| 38 | (R)-4-[(1-Cyclohexylethyl)amino]-1-ethyl-N-(4-pyridinylmethyl)-1H-pyrazolo[3,4-b]pyridine-5-carboxamide | 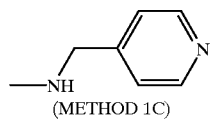<br>(METHOD 1C) | 89 | 3.25 | m/z (M + H) 407 |
| 39 | (R)-4-[(1-Cyclohexylethyl)amino]-1-ethyl-N-[2-(2-thienyl)ethyl]-1H-pyrazolo[3,4-b]pyridine-5-carboxamide | 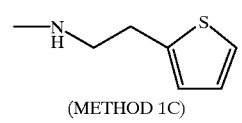<br>(METHOD 1C) | 92 | 4.36 | m/z (M + H) 425 |
| 40 | (R)-4-[(1-Cyclohexylethyl)amino]-1-ethyl-N-[2-(1-methyl-2-pyrrolidinyl)ethyl]-1H-pyrazolo[3,4-b]pyridine-5 carboxamide | 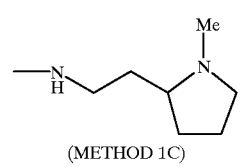<br>(METHOD 1C) | 94 | 3.19 | m/z (M + H) 427 |
| 41 | (R)-4-[(1-Cyclohexylethyl)amino]-1-ethyl-N-[3-(4-morpholinyl)propyl]-1H-pyrazolo[3,4-b]pyridine-5-carboxamide | 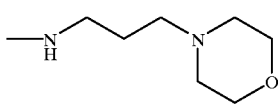<br>(METHOD 1C) | 85 | 3.09 | m/z (M + H) 442 |
| 42 | (R)-4-[(1-Cyclohexylethyl)amino]-N-[(2,4-dimethoxyphenyl)methyl]-1-ethyl-1H-pyrazolo[3,4-b]pyridine-5-carboxamide | 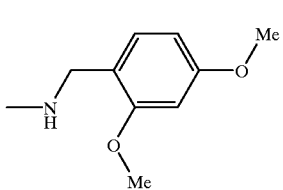<br>(METHOD 1C) | 93 | 4.3 | m/z (M + H) 466 |
| 43 | (R)-4-[(1-Cyclohexylethyl)amino]-N-[2-(3,4-dimethoxyphenyl)ethyl]-1-ethyl-1H-pyrazolo[3,4-b]pyridine-5-carboxamide | 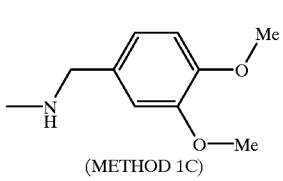<br>(METHOD 1C) | 94 | 4.19 | m/z (M + H) 480 |
| 44 | (R)-4-[(1-Cyclohexylethyl)amino]-N-[(3,4-difluorophenyl)methyl]-1-ethyl-1H-pyrazolo[3,4-b]pyridine-5-carboxamide | 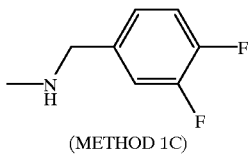<br>(METHOD 1C) | 93 | 4.50 | m/z (M + H) 442 |
| 45 | (R)-4-[(1-Cyclohexylethyl)amino]-1-ethyl-N-[2-(1-pyrrolidinyl)ethyl]-1H-pyrazolo[3,4-b]pyridine-5-carboxamide | 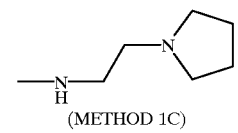<br>(METHOD 1C) | 91 | 3.15 | m/z (M + H) 413 |
| 46 | (R)-N-[[4-[(1-Cyclohexylethyl)amino]-1-ethyl-1H-pyrazolo[3,4-b]pyridin-5-yl]carbonyl]glycine ethyl ester | 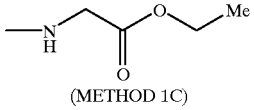<br>(METHOD 1C) | 90 | 4.01 | m/z (M + H) 401 |

-continued

| Ex | Name | X₁ | PURITY (%) | HPLC (retention time, minutes) | OTHER DATA |
|---|---|---|---|---|---|
| 47 | (R)-4-[(1-Cyclohexylethyl)amino]-1-ethyl-N-[1-(phenylmethyl)-3-pyrrolidinyl]-1H-pyrazolo[3,4-b]pyridine-5-carboxamide | (pyrrolidinyl-N-benzyl structure) (METHOD 1C) | 92 | 3.54 | m/z (M + H) 475 |
| 48 | (R)-N-[2-[4-(Aminosulfonyl)phenyl]ethyl]-4-[(1-cyclohexylethyl)amino]-1-ethyl-1H-pyrazolo[3,4-b]pyridine-5-carboxamide | (4-sulfamoylphenethylamine structure) (METHOD 1C) | 93 | 3.76 | m/z (M + H) 498 |
| 49 | (R)-4-[(1-Cyclohexylethyl)amino]-1-ethyl-N-[(3,4,5-trimethoxyphenyl)methyl]-1H-pyrazolo[3,4-b]pyridine-5-carboxamide | (3,4,5-trimethoxybenzylamine structure) (METHOD 1C) | 93 | 4.17 | m/z (M + H) 496 |
| 50 | (R)-4-[(1-Cyclohexylethyl)amino]-1-ethyl-N-(6-hydroxyhexyl)-1H-pyrazolo[3,4-b]pyridine-5-carboxamide | (6-hydroxyhexylamine structure) (METHOD 1C) | 94 | 3.96 | m/z (M + H) 416 |
| 51 | (1R)-4-[(1-Cyclohexylethyl)amino]-N-(2,3-dihydroxypropyl)-1-ethyl-1H-pyrazolo[3,4-b]pyridine-5-carboxamide | (2,3-dihydroxypropylamine structure) (METHOD 1C) | 95 | 3.39 | m/z (M + H) 390 |
| 52 | [S-(R*,S*)]-1-[[4-[(1-Cyclohexylethyl)amino]-1-ethyl-1H-pyrazolo[3,4-b]pyridin-5-yl]carbonyl]-2-pyrrolidinecarboxamide | (prolinamide structure) (METHOD 1C) | 94 | 3.18 | m/z (M + H) 413 |
| 53 | (R)-1-(1,3-Benzodioxol-5-ylmethyl)-4-[[4-[(1-cyclohexylethyl)amino]-1-ethyl-1H-pyrazolo[3,4-b]pyridin-5-yl]carbonyl]piperazine | (benzodioxolylmethyl-piperazine structure) (METHOD 1C) | 93 | 3.27 | m/z (M + H) 519 |
| 54 | (R)-4-[(1-Cyclohexylethyl)amino]-1-ethyl-N-(2-hydroxyethyl)-N-propyl-1H-pyrazolo[3,4-b]pyridine-5-carboxamide | (N-(2-hydroxyethyl)-N-propylamine structure) (METHOD 1C) | 96 | 3.53 | m/z (M + H) 402 |

-continued

| Ex | Name | X₁ | PURITY (%) | HPLC (retention time, minutes) | OTHER DATA |
|---|---|---|---|---|---|
| 55 | (R)-4-[[4-[(1-Cyclohexylethyl)amino]-1-ethyl-1H-pyrazolo[3,4-b]pyridin-5-yl]carbonyl]-1-piperazinecarboxylic acid ethyl ester | 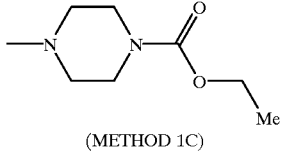<br>(METHOD 1C) | 95 | 3.90 | m/z (M + H) 457 |
| 56 | (R)-4-[[4-[(1-Cyclohexylethyl)amino]-1-ethyl-1H-pyrazolo[3,4-b]pyridin-5-yl]carbonyl]-morpholine | 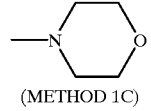<br>(METHOD 1C) | 100 | 3.51 | m/z (M + H) 386 |
| 57 | (R)-8-[[4-[(1-Cyclohexylethyl)amino]-1-ethyl-1H-pyrazolo[3,4-b]pyridin-5-yl]carbonyl]-4-oxo-1-phenyl-1,3,8-triazaspiro[4.5]decane | 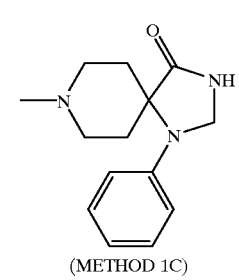<br>(METHOD 1C) | 95 | 4.18 | m/z (M + H) 530 |
| 58 | (R)-4-[(1-Cyclohexylethyl)amino]-1-ethyl-N-methyl-N-(1-methyl-4-piperidinyl)-1H-pyrazolo[3,4-b]pyridine-5-carboxamide | 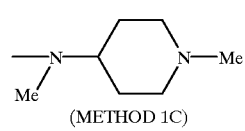<br>(METHOD 1C) | 92 | 2.79 | m/z (M + H) 427 |
| 59 | [S-(R*,S*)]-1-[[4-[(1-Cyclohexylethyl)amino]-1-ethyl-1H-pyrazolo[3,4-b]pyridin-5-yl]carbonyl]-2-(hydroxymethyl)pyrrolidine | 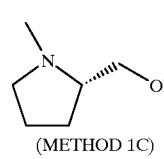<br>(METHOD 1C) | 85 | 3.48 | m/z (M + H) 400 |
| 60 | (R)-1-[[4-((1-Cyclohexylethyl)amino]-1-ethyl-1H-pyrazolo[3,4-b]pyridin-5-yl]carbonyl]-4-(phenylmethyl)piperidine | 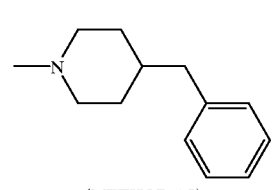<br>(METHOD 1C) | 92 | 4.62 | m/z (M + H) 474 |
| 61 | [S-(R*,S*)]-1-[[4-[(1-Cyclohexylethyl)amino]-1-ethyl-1H-pyrazolo[3,4-b]pyridin-5-yl]carbonyl]-2-[[(2,6-dimethylphenyl)amino]methyl]pyrrolidine | 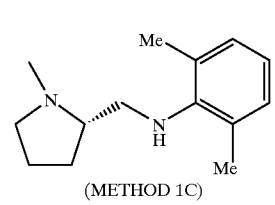<br>(METHOD 1C) | 93 | 4.05 | m/z (M + H) 503 |
| 62 | (R)4-[(1-Cyclohexylethyl)amino]-N-[2-(diethylamino)ethyl]-1-ethyl-N-methyl-1H-pyrazolo[3,4-b]pyridine-5-carboxamide | 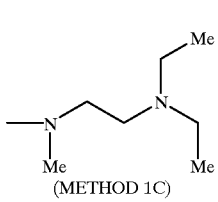<br>(METHOD 1C) | 97 | 2.90 | m/z (M + H) 429 |

-continued

| Ex | Name | X₁ | PURITY (%) | HPLC (retention time, minutes) | OTHER DATA |
|---|---|---|---|---|---|
| 63 | (R)-4-[[4-[(1-Cyclohexylethyl)amino]-1-ethyl-1H-pyrazolo[3,4-b]pyridin-5-yl]carbonyl]thiomorpholine | 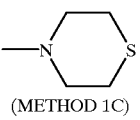 (METHOD 1C) | 90 | 3.87 | m/z (M + H) 402 |
| 64 | (R)-1-[[4-[(1-Cyclohexylethyl)amino]-1-ethyl-1H-pyrazolo[3,4-b]pyridin-5-yl]carbonyl]piperidine | 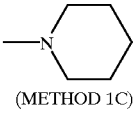 (METHOD 1C) | 95 | 3.92 | m/z (M + H) 384 |
| 65 | (1R)-1-[[4-[(1-Cyclohexylethyl)amino]-1-ethyl-1H-pyrazolo[3,4-b]pyridin-5-yl]carbonyl]-3-piperidinecarboxylic acid ethyl ester | 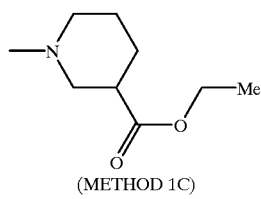 (METHOD 1C) | 94 | 3.99 | m/z (M + H) 456 |
| 66 | (R)-4-[(1-Cyclohexylethyl)amino]-1-ethyl-N-propyl-N-[2-(2-pyridinyl)ethyl]-1H-pyrazolo[3,4-b]pyridine-5-carboxamide | 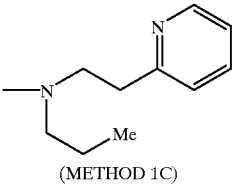 (METHOD 1C) | 100 | 3.48 | m/z (M + H) 463 |
| 67 | (1R)-1-[[4-[(1-Cyclohexylethyl)amino]-1-ethyl-1H-pyrazolo[3,4-b]pyridin-5-yl]carbonyl]-3-(hydroxymethyl)piperidine | 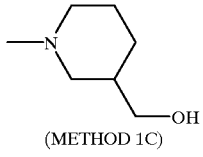 (METHOD 1C) | 100 | 3.50 | m/z (M + H) 414 |
| 68 | (R)-2-[[4-[(1-Cyclohexylethyl)amino]-1-ethyl-1H-pyrazolo[3,4-b]pyridin-5-yl]carbonyl]-1,2,3,4-tetrahydro-6,7-dimethoxyisoquinoline | 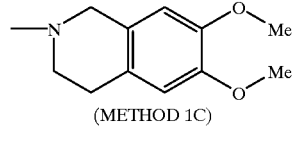 (METHOD 1C) | 96 | 3.96 | m/z (M + H) 492 |
| 69 | (R)-4-(4-Chlorophenyl)-1-[[4-[(1-cyclohexylethyl)amino]-1-ethyl-1H-pyrazolo[3,4-b]pyridin-5-yl]carbonyl]-1,2,3,6-tetrahydropyridine | 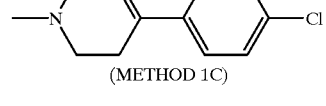 (METHOD 1C) | 95 | 4.69 | m/z (M + H) 492 |
| 70 | (1R)-4-[[4-[(1-Cyclohexylethyl)amino]-1-ethyl-1H-pyrazolo[3,4-b]pyridin-5-yl]carbonyl]-1-(4-methoxyphenyl)-2-methylpiperazine | 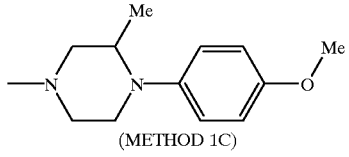 (METHOD 1C) | 96 | 3.91 | m/z (M + H) 505 |

-continued

| Ex | Name | X₁ | PURITY (%) | HPLC (retention time, minutes) | OTHER DATA |
|----|------|----|-----------|--------------------------------|------------|
| 71 | (R)-1-[Bis(4-fluorophenyl)methyl]-4-[[4-[(1-cyclohexylethyl)amino]-1-ethyl-1H-pyrazolo[3,4-b]pyridin-5-yl]carbonyl-piperazine | 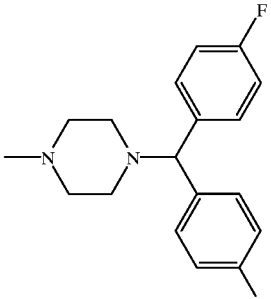<br>(METHOD 1C) | 93 | 4.53 | m/z (M + H) 587 |
| 72 | (R)4-[(1-Cyclohexylethyl)amino]-(dimethylamino)ethyl]-1-ethyl-N-(phenylmethyl)-1H-pyrazolo[3,4-b]pyridine-5-carboxamide | 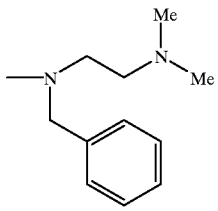<br>(METHOD 1C) | 76 | 3.61 | m/z (M + H) 477 |
| 73 | (R)-1-[[4-[(1-Cyclohexylethyl)amino]-1-ethyl-1H-pyrazolo[3,4-b]pyridin-5-yl]carbonyl]-4-phenylpiperazine | 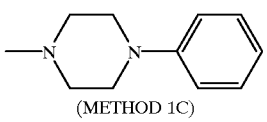<br>(METHOD 1C) | 93 | 4.31 | m/z (M + H) 461 |
| 74 | (R)-1-[[4-[(1-Cyclohexylethyl)amino]-1-ethyl-1H-pyrazolo[3,4-b]pyridin-5-yl]carbonyl]-4-(2-hydroxyethyl)piperazine | 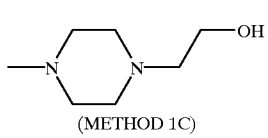<br>(METHOD 1C) | 92 | 2.89 | m/z (M + H) 429 |
| 75 | (R)-1-(2-Chlorophenyl)-4-[[4-[(1-cyclohexylethyl)amino]-1-ethyl-1H-pyrazolo[3,4-b]pyridin-5-yl]-carbonyl]piperazine | 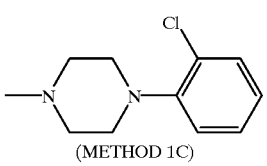<br>(METHOD 1C) | 94 | 4.63 | m/z (M + H) 495 |
| 76 | (1R)-1-[[4-[(1-Cyclohexylethyl)amino]-1-ethyl-1H-pyrazolo[3,4-b]pyridin-5-yl]carbonyl]-3-piperidinecarboxamide | 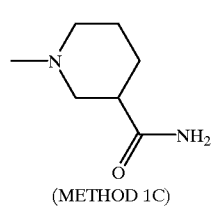<br>(METHOD 1C) | 94 | 3.31 | m/z (M + H) 427 |
| 77 | (R)-1-[[4-[(1-Cyclohexylethyl)amino]-1-ethyl-1H-pyrazolo[3,4-b]pyridin-5-yl]carbonyl]-4-hydroxypiperidine | 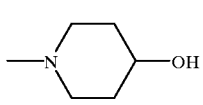<br>(METHOD 1C) | 98 | 3.34 | m/z (M + H) 400 |

-continued

| Ex | Name | X₁ | PURITY (%) | HPLC (retention time, minutes) | OTHER DATA |
|----|------|----|-----------|-------------------------------|------------|
| 78 | (R)-1-[[4-[(1-Cyclohexylethyl)amino]-1-ethyl-1H-pyrazolo[3,4-b]pyridin-5-yl]carbonyl]-4-methylpiperidine | (METHOD 1C) | 94 | 4.17 | m/z (M + H) 398 |
| 79 | (R)-1-[[4-[(1-Cyclohexylethyl)amino]-1-ethyl-1H-pyrazolo[3,4-b]pyridin-5-yl]carbonyl]-4-(3,4-dichlorophenyl)piperazine | (METHOD 1C) | 92 | 4.75 | m/z (M + H) 529 |
| 80 | [S-(R*,S*)]-1-[[4-[(1-Cyclohexylethyl)amino]-1-ethyl-1H-pyrazolo[3,4-b]pyridin-5-yl]carbonyl]-2-(methoxymethyl)pyrrolidine | (METHOD 1C) | 80 | 3.85 | m/z (M + H) 414 |
| 81 | (R)-1-[[4-[(1-Cyclohexylethyl)amino]-1-ethyl-1H-pyrazolo[3,4-b]pyridin-5-yl]carbonyl]-4-(3-methoxyphenyl)piperazine | (METHOD 1C) | 98 | 4.32 | m/z (M + H) 491 |
| 82 | (R)-1-[[4-[(1-Cyclohexylethyl)amino]-1-ethyl-1H-pyrazolo[3,4-b]pyridin-5-yl]carbonyl]-4-(4-methoxyphenyl)piperazine | (METHOD 1C) | 95 | 4.14 | m/z (M + H) 491 |
| 83 | (1R)-N-[1-[[4-[(1-Cyclohexylethyl)amino]-1-ethyl-1H-pyrazolo[3,4-b]pyridin-5-yl]carbonyl]-3-pyrrolidinyl]acetamide | (METHOD 1C) | 95 | 3.31 | m/z (M + H) 427 |
| 84 | (R)-1-[[4-[(1-Cyclohexylethyl)amino]-1-ethyl-1H-pyrazolo[3,4-b]pyridin-5-yl]carbonyl]hexahydro-4-methyl-1H-1,4-diazepine | (METHOD 1C) | 94 | 2.76 | m/z (M + H) 413 |
| 85 | (1R)-4-[(1-Cyclohexylethyl)amino]-N,1-diethyl-N-(1-ethyl-3-pyrrolidinyl)-1H-pyrazolo[3,4-b]pyridine-5-carboxamide | (METHOD 1C) | 90 | 2.93 | m/z (M + H) 441 |

-continued

| Ex | Name | X$_1$ | PURITY (%) | HPLC (retention time, minutes) | OTHER DATA |
|---|---|---|---|---|---|
| 86 | (R,Z)-1-[[4-[(1-Cyclohexylethyl)amino]-1-ethyl-H-pyrazolo[3,4-b]pyridin-5-yl]carbonyl]-4-(3-phenyl-2-propenyl)piperazine | (METHOD 1C) | 96 | 3.52 | m/z (M + H) 501 |
| 87 | (1R)-1-[[4-[(1-Cyclohexylethyl)amino]-1-ethyl-1H-pyrazolo(3,4-b)pyridin-5-yl]carbonyl]-4-hydroxy-4-(phenylmethyl)piperidine | (METHOD 1C) | 93 | 4.18 | m/z (M + H) 490 |
| 88 | (R)-1-[[4-[(1-Cyclohexylethyl)amino]-1-ethyl-1H-pyrazolo[3,4-b]pyridin-5-yl]carbonyl]-4-piperidinecarboxamide | (METHOD 1C) | 93 | 3.22 | m/z (M + H) 427 |
| 89 | (R)-1-[[4-[(1-Cyclohexylethyl)amino]-1-ethyl-1H-pyrazolo[3,4-b]pyridin-5-yl]carbonyl]-4-(2-pyridinyl)piperazine | (METHOD 1C) | 94 | 3.01 | m/z (M + H) 462 |
| 90 | (R)-4-[(1-Cyclohexylethyl)amino]-1-ethyl-N-methyl-N-[2-(2-pyridinyl)ethyl]-1H-pyrazolo[3,4-b]pyridine-5-carboxamide | (METHOD 1C) | 94 | 2.92 | m/z (M + H) 435 |
| 91 | (R)4-[(1-Cyclohexylethyl)amino]-1-ethyl-N,N-bis(2-pyridinylmethyl)-1H-pyrazolo[3,4-b]pyridine-5-carboxamide | (METHOD 1C) | 92 | 3.43 | m/z (M + H) 498 |
| 92 | (R)-1-Acetyl-4-[[4-[(1-cyclohexylethyl)amino]-1-ethyl-1H-pyrazolo[3,4-b]pyridin-5-yl]carbonyl]piperazine | (METHOD 1C) | 97 | 3.36 | m/z (M + H) 427 |
| 93 | (R)-1-[[4-[(1-Cyclohexylethyl)amino]-1-ethyl-1H-pyrazolo[3,4-pyridin-5-yl]carbonyl]-4-(2-fluorophenyl)piperazine | (METHOD 1C) | 92 | 4.41 | m/z (M + H) 479 |
| 94 | (R)-4-[(1-Cyclohexylethyl)amino]-1-ethyl-N-methyl-N-[2-(4-pyridinyl)ethyl]-1H-pyrazolo[3,4-b]pyridine-5-carboxamide | (METHOD 1C) | 92 | 2.91 | m/z (M + H) 435 |

-continued

| Ex | Name | X$_1$ | PURITY (%) | HPLC (retention time, minutes) | OTHER DATA |
|---|---|---|---|---|---|
| 95 | (1R)-4-[(1-Cyclohexylethyl)amino]-1-ethyl-N-methyl-N-[1-(phenylmethyl)-3-pyrrolidinyl]-1H-pyrazolo[3,4-b]pyridine-5-carboxamide | (METHOD 1C) | 93 | 3.36 | m/z (M + H) 489 |
| 96 | (R)-4-[(1-Cyclohexylethyl)amino]-1-ethyl-N-3-pyridinyl-1H-pyrazolo[3,4-b]pyridine-5-carboxamide | (METHOD 1A) | 96 | 3.57 | m/z (M + H) 393 |
| 97 | (R)-4-[(1-Cyclohexylethyl)amino]-1-ethyl-N-[2-(4-morpholinyl)ethyl]-1H-pyrazolo[3,4-b]pyridine-5-carboxamide | (METHOD 1A) | 98 | 3.23 | m/z (M + H) 429 |
| 98 | 4-[[(R)-1-Cyclohexylethyl]amino]-1-ethyl-N-[1-(4-hydroxyphenyl)ethyl]-1H-pyrazolo[3,4-b]pyridine-5-carboxamide | (METHOD 1A) | 99 | 3.78 & 3.87 | m/z (M + H) 436 |

The following compounds of formula I were prepared wherein R$_3$ is ethyl, R$_4$ is hydrogen, Y is nitrogen, Z is CH, and E$_1$ is

| Ex. | Name | X$_2$ | PURITY (%) | HPLC (retention time, minutes) | OTHER DATA |
|---|---|---|---|---|---|
| 99 | (S)-4-[(1-Cyclohexylethyl)amino]-1-ethyl-N-(4-pyridinylmethyl)-1H-pyrazolo[3,4-b]pyridine-5-carboxamide | (METHOD 1A) | 100 | 3.27 | m/z (M + H) 407 |
| 100 | (S)-4-[[[4-[(1-Cyclohexylethyl)amino]-1-ethyl-1H-pyrazolo[3,4-b]pyridin-5-yl]carbonyl]amino]-1-piperidinecarboxylic acid ethyl ester | (METHOD 1A) | 89 | 4.07 | m/z (M + H) 471 |

-continued

| Ex. | Name | X₂ | PURITY (%) | HPLC (retention time, minutes) | OTHER DATA |
|---|---|---|---|---|---|
| 101 | (S)-4-[(1-Cyclohexylethyl)amino]-1-ethyl-N-(3-pyridinylmethyl)-1H-pyrazolo[3,4-b]pyridine-5-carboxamide | (METHOD 1A) | 100 | 3.28 | m/z (M + H) 407 |
| 102 | (1S)-4-[(1-Cyclohexylethyl)amino]-1-ethyl-N-(hexahydro-2-oxo-1H-azepin-3-yl)-1H-pyrazolo[3,4-b]pyridine-5-carboxamide | (METHOD 1A) | 97 | 3.71 | m/z (M + H) 427 |
| 103 | (S)-4-[(1-Cyclohexylethyl)amino]-1-ethyl-N-[3-(2-oxo-pyrrolidinyl)propyl]-1H-pyrazolo[3,4-b]pyridine-5-carboxamide | (METHOD 1A) | 90 | 3.65 | m/z (M + H) 441 |
| 104 | (S)-4-[(1-Cyclohexylethyl)amino]-1-ethyl-N-[(4-hydroxy-3-methoxyphenyl)methyl]-1H-pyrazolo[3,4-b]pyridine-5-carboxamide | (METHOD 1A) | 97 | 3.81 | m/z (M + H) 452 |

The following compounds of formula I were prepared wherein $R_3$ is ethyl, $R_4$ is hydrogen, Y is nitrogen, and Z is CH:

| Ex. | Name | $E_1$ | $X_1$ | PURITY (%) | HPLC (retention time, minutes) | OTHER DATA |
|---|---|---|---|---|---|---|
| 105 | 4-[[(4-Morpholinyl)-ethyl]amino]-1-ethyl-N-(4-pyridinylmethyl)-1H-pyrazolo[3,4-b]pyridine-5-carboxamide | | Method 2 | 99 | 0.80 | m/z (M + H) 410 |
| 106 | 4-[(N-(3-1H-Imidazol-1-yl)propyl)amino]-1-ethyl-N-(4-pyridinylmethyl)-1H-pyrazolo[3,4-b]pyridine-5-carboxamide | —N—(CH₂)₃— | Method 2 | 98 | 1.20 | m/z (M + H) 405 |

-continued

| Ex. | Name | E₁ | X₁ | PURITY (%) | HPLC (retention time, minutes) | OTHER DATA |
|---|---|---|---|---|---|---|
| 107 | 4-[[(3-Chloro-4-methoxyphenyl)methyl]hydroxyl]-1-ethyl-N-(4-pyridinylmethyl)-1H-pyrazolo[3,4-b]pyridine-5-carboxamide | O—CH₂—(3-Cl,4-OCH₃-phenyl) | | 99 | 2.81 | m/z (M + H) 452 Method 2 |

The following compounds of formula II were prepared wherein $R_3$ is ethyl, $R_4$ is hydrogen, Y is nitrogen, Z is CH, and $E_2$ is —NH—CH₂—(3-Cl, 4-OCH₃-phenyl)

| Ex. | Name | X₂ | PURITY (%) | HPLC (retention time, minutes) | OTHER DATA |
|---|---|---|---|---|---|
| 108 | 4-[[[4-[[(3-Chloro-4-methoxyphenyl)methyl]amino]-1-ethyl-1H-pyrazolo[3,4-b]pyridin-5-yl]carbonyl]amino]-1-piperidine-carboxylic acid ethyl ester | —NH—(piperidin-4-yl)—N—C(O)OEt (METHOD 1B) | 96 | 3.62 | mp 184–185° C.; Anal. Calcd for $C_{25}H_{31}ClN_6O_4$: C, 58.30; H, 6.07; N, 16.32; Cl, 6.88. Found: C, 58.14; H, 6.18; N, 16.22; Cl, 6.58. |
| 109 | 4-[[(3-Chloro-4-methoxyphenyl)methyl]amino]-1-ethyl-N-[3-(2-oxo-1-pyrrolidinyl)propyl]-1H-pyrazolo[3,4-b]pyridine-5-carboxamide | —NH—(CH₂)₃—N(2-oxopyrrolidinyl) (METHOD 1A) | 98 | 3.2 | mp 149–150° C.; Anal. Calcd for $C_{24}H_{29}ClN_6O_3$: C, 59.44; H, 6.03; N, 17.33; Cl, 7.31. Found: C, 59.54; H, 5.89; N, 17.38; Cl, 7.37. |
| 110 | 4-[[(3-Chloro-4-methoxyphenyl)methyl]amino]-1-ethyl-N-(2-pyridinylmethyl)-1H-pyrazolo[3,4-b]pyridine-5-carboxamide | —NH—CH₂—(2-pyridyl) (METHOD 1A) | 98 | 2.95 | mp 176–177° C.; Anal. Calcd for $C_{23}H_{23}ClN_6O_2$: C, 61.26; H, 5.14; N, 18.64; Cl, 7.86. Found: C, 60.99; H, 5.00; N, 18.71; Cl 7.92. |

-continued

[Structure: —NH—CH₂—(phenyl with OCH₃ and Cl substituents)]

| Ex. | Name | X₂ | PURITY (%) | HPLC (retention time, minutes) | OTHER DATA |
|---|---|---|---|---|---|
| 111 | 4-[[(3-Chloro-4-methoxyphenyl)methyl]amino]-1-ethyl-N-(3-pyridinylmethyl)-1H-pyrazolo[3,4-b]pyridine-5-carboxamide | [—NH—CH₂—(3-pyridinyl)] (METHOD 1A) | 98 | 2.90 | mp 198° C. NMR C$^{13}$H$^{1}$ m/z (M + H) 451 |
| 112 | 4-[[[4-[[(3-Chloro-4-methoxyphenyl)methyl]amino]-1-ethyl-1H-pyrazolo[3,4-b]pyridin-5-yl]carbonyl]amino]-1-piperidinecarboxylic acid ethyl ester | [—NH—(piperidinyl)—C(O)—O—Me] (METHOD 1A) | 98 | 3.70 | mp 182–184° C. NMR C$^{13}$H$^{1}$ m/z (M + H) 515 |
| 113 | 4-[[(3-Chloro-4-methoxyphenyyl)methyl]amino-1-ethyl-N-(hexahydro-2-oxo-1H-azepin-3-yl)-1H-pyrazolo[3,4-b]pyridine-5-carboxamide | [hexahydro-2-oxo-azepinyl-NH—] (METHOD 1A) | 93 | 3.30 | mp 214–216° C. NMR C$^{13}$H$^{1}$ m/z (M + H) 471 |
| 114 | 4-[[(3-Chloro-4-methoxyphenyl)methyl]amino]-1-ethyl-N-[(4-hydroxy-3-methoxyphenyl)methyl]-1H-pyrazolo[3,4-b]pyridine-5-carboxamide | [—NH—CH₂—(phenyl with OMe and OH)] (METHOD 1A) | 99 | 3.45 | mp 119–121° C. NMR C$^{13}$H$^{1}$ m/z (M + H) 496 |
| 115 | 4-[[(3-Chloro-4-methoxyphenyl)methyl]amino]-1-ethyl-N-[[4-(1,2,3-thiadiazol-4-yl)phenyl]methyl]-1H-pyrazolo[3,4-b]pyridine-5-carboxamide | [—NH—CH₂—(phenyl)—(1,2,3-thiadiazol-4-yl)] (METHOD 1A) | 97 | 3.30 | mp 194–196° C. NMR C$^{13}$H$^{1}$ m/z (M + H) 534 |
| 116 | N-[[4-[[(3-Chloro-4-methoxyphenyl)methyl]amino]-1-ethyl-1H-pyrazolo[3,4-b]pyridin-5-yl]carbonyl]glycine ethyl ester | [—NH—CH₂—C(O)—O—Me] (METHOD 1A) | 95 | 3.40 | mp 149–152° C. NMR C$^{13}$H$^{1}$ m/z (M + H) 446 |
| 117 | 4-[[3-Chloro-4-methoxyphenyl)methyl]amino]-1-ethyl-N-(3-1H-imidazol-1-ylpropyl)1H-pyrazolo[3,4-b]pyridine-5-carboxamide | [—NH—(CH₂)₃—(1H-imidazol-1-yl)] (METHOD 1A) | 99 | 2.90 | mp 108–110° C. NMR C$^{13}$H$^{1}$ m/z (M + H) 468 |

-continued

[Structure: -NH-CH2-C6H3(OCH3)(Cl) - 3-chloro-4-methoxybenzyl amine group]

| Ex. | Name | X₂ | PURITY (%) | HPLC (retention time, minutes) | OTHER DATA |
|---|---|---|---|---|---|
| 118 | N-[(3-Chloro-4-methoxyphenyl)methyl]-4-[[(3-chloro-4-methoxyphenyl)methyl]amino]-1-ethyl-1H-pyrazolo[3,4-b]pyridine-5-carboxamide | (METHOD 1A) | 93 | 3.80 | NMR C$^{13}$H$^{1}$ m/z (M + H) 514 |
| 119 | 4-[[(3-Chloro-4-methoxyphenyl)methyl]amino]-1-ethyl-N,N-bis(2-pyridinylmethyl)-1H-pyrazolo[3,4-b]pyridine-5-carboxamide | (METHOD 1A) | 92 | 3.00 | NMR C$^{13}$H$^{1}$ m/z (M + H) 542 |
| 120 | (R)-α-[[4-[[(3-Chloro-4-methoxyphenyl)methyl]amino]-1-ethyl-1H-pyrazolo[3,4-b]pyridin-5-yl]carbonyl]amino]benzeneacetic acid ethyl ester | (METHOD 1A) | 94 | 3.80 | NMR C$^{13}$H$^{1}$ m/z (M + H) 522 |
| 121 | 4-[[(3-Chloro-4-methoxyphenyl)methyl]amino]1-ethyl-N-[1-(phenylmethyl)-4-piperidinyl]-1H-pyrazolo[3,4-b]pridine-5-carboxamide | (METHOD 1A) | 96 | 3.10 | NMR C$^{13}$H$^{1}$ m/z (M + H) 533 |
| 122 | 4-[[(3-Chloro-4-methoxyphenyl)methyl]amino]-1-ethyl-N-[3-(4-morpholinyl)propyl]-1H-pyrazolo[3,4-b]pyridine-5-carboxamide | (METHOD 1A) | 98 | 2.80 | NMR C$^{13}$H$^{1}$ m/z (M + H) 487 |
| 123 | 4-[[(3-Chloro-4-methoxyphenyl)methyl]amino]-N-[2-(dimethylamino)ethyl]-1-ethyl-N-(phenylmethyl-1H-pyrazolo[3,4-b]pyridine-5-carboxamide | (METHOD 1A) | 88 | 3.10 | NMR C$^{13}$H$^{1}$ m/z (M + H) 521 |

-continued

[Structure: —NH—CH₂—(phenyl with —OCH₃ and —Cl substituents)]

| Ex. | Name | X₂ | PURITY (%) | HPLC (retention time, minutes) | OTHER DATA |
|---|---|---|---|---|---|
| 124 | 4-[[(3-Chloro-4-methoxyphenyl)methyl)mino]-1-ethyl-N-[(4-pyridinyl-1-oxide)methyl]-1H-pyrazolo[3,4-b]pyridine-5-carboxamide | [structure: —NH—CH₂-(pyridinyl N-oxide)] (METHOD 1A) | 97 | 3.20 | NMR $C^{13}H^{1}$ m/z (M + H) 467 |
| 125 | 4-[[(3-Chloro-4-methoxypehynl)methyl]amino]-1-ethyl-N-(2-furanylmethyl)-1H-pyrazolo[3,4-b]pyridine-5-carboxamide | [structure: —NH—CH₂-furan] (METHOD 1B) | 100 | 3.73 | m/z (M + H) 440 |
| 126 | N-[[4-[[(3-Chloro-4-methoxyphenyl)methyl]amino]-1-ethyl-1H-pyrazolo[3,4-b]pyrazolo[3,4-b]pyridin-5-yl]carbonyl]-L-valine ethyl ester | [structure: valine ethyl ester] (METHOD 1B) | 92 | 4.06 | m/z (M + H 488 |
| 127 | 4-[[(3-Chloro-4-methoxyphenyl)methyl]amino]-N-(cyanomethyl)-1-ethyl-1H-pyrazolo[3,4-b]pyridine-5-carboxamide | [structure: —NH—CH₂—C≡N] (METHOD 1B) | 92 | 3.40 | m/z (M + H) 399 |
| 128 | N2-[[4-[[(3-Chloro-4-methoxyphenyl)methyl]amino]-1-ethyl-1H-pyrazolo[3,4-b]pyridin-5-yl]carbonyl]-N6-[(phenylmethoxy)carbonyl]L-lysine methyl ester | [structure: L-lysine derivative] (METHOD 1B) | 82 | 4.07 | m/z (M + H) 637 |
| 129 | N-[2-(Acetylamino)ethyl]-4-[[(3-chloro-4-methoxyphenyl)methyl]amino]-1-ethyl-1H-pyrazolo[3,4-b]pyridine-5-carboxamide | [structure: —NH—CH₂CH₂—NH—C(O)Me] (METHOD 1B) | 100 | 3.12 | m/z (M + H) 445 |
| 130 | N-[N-[[4-[[(3-Chloro-4-methoxyphenyl)methyl]amino]-1-ethyl-1H-pyrazolo[3,4-b]pyridin-5-yl]carbonyl]L-alanyl]glycine methyl ester | [structure: L-alanyl-glycine methyl ester] (METHOD 1B) | 100 | 3.17 | m/z (M + H) 503 |

-continued

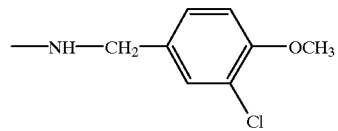

| Ex. | Name | X₂ | PURITY (%) | HPLC (retention time, minutes) | OTHER DATA |
|---|---|---|---|---|---|
| 131 | [4-[[[4-[[(3-Chloro-4-methoxyphenyl)methyl]amino]-1-ethyl-1H-pyrazolo[3,4-b]pyridin-5-yl]carbonyl]amino]butyl]carbamic acid 1,1-dimethylethyl ester | (METHOD 1B) | 96 | 2.79 | m/z (M + H) 531 |
| 132 | 4-[[(3-Chloro-4-methoxyphenyl)methyl]amino]-1-ethyl-N-(1,2,3,4-tetrahydro-1-naphthalenyl)-1H-pyrazolo[3,4-b]pyridine-5-carboxamide | (METHOD 1B) | 98 | 4..33 | m/z (M + H) 490 |
| 133 | 4-[[(3-Chloro-4-methoxyphenyl)methyl]amino]-1-ethyl-N-(tetrahydro-2-duranylmethyl)1H-pyrazolo[3,4-b]pyridine-5-carboxamide | (METHOD 1B) | 92 | 3.53 | m/z (M + H) 444 |
| 134 | 4-[[(3-Chloro-4-methoxyphenyl)methyl]amino]-N-[[4-(dimethylamino)phenyl]methyl]-1-ethyl-1H-pyrazolo[3,4-b]pyridine-5-carboxamide | (METHOD 1B) | 100 | 3.09 | m/z (M + H) 493 |
| 135 | N-[[4-[[(3-Chloro-4-methoxyphenyl)methyl]amino]-1-ethyl-1H-pyrazolo[3,4-b]pyridin-5-yl]carbonyl]L-alanine methyl ester | (METHOD 1B) | 97 | 3.53 | m/z (M + H) 446 |
| 136 | (S)-2-(Acetylamino)-6-[[[4-[[(3-chloro-4-methoxyphenyl)methyl]amino]-1-ethyl-1H-pyrazolo[3,4-b]pyridin-5-yl]carbonyl]amino]hexanamide | (METHOD 1B) | 100 | 3.25 | m/z (M + H) 544 |

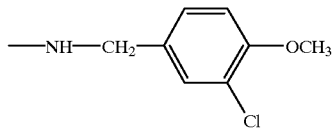

| Ex. | Name | X₂ | PURITY (%) | HPLC (retention time, minutes) | OTHER DATA |
|---|---|---|---|---|---|
| 137 | 4-[[(3-Chloro-4-methoxyphenyl)methyl]amino]-1-ethyl-N-[[4-fluoro-2-(trifluoromethyl)phenyl]methyl]-1H-pyrazolo[3,4-b]pyridine-5-carboxamide | (METHOD 1B) | 96 | 4.39 | m/z (M + H) 536 |
| 138 | (4S-cis)-4-[[(3-Chloro-4-methoxyphenyl)methyl]amino]-1-ethyl-N-(2,2-dimethyl-4-phenyl-1,3-dioxan-5-yl)-1H-pyrazolo[3,4-b]pyridine-5-carboxamide | (METHOD 1B) | 88 | 4.07 | m/z (M + H) 550 |
| 139 | N-[[4-[[(3-Chloro-4-methoxypehynl)methyl]amino]-1-ethyl-1H-pyrazolo[3,4-b]pyridin-5-yl]carbonyl]-L-methionine methyl ester | (METHOD 1B) | 85 | 3.89 | m/z (M + H) 506 |
| 140 | 2-[[[4-[[(3-Chloro-4-methoxyphenyl)methyl]amino]-1-ethyl-1H-pyrazolo[3,4-b]pyridin-5-yl]carbonyl]amino]propanedioic acid diethyl ester | (METHOD 1B) | 74 | 3.95 | m/z (M + H) 518 |
| 141 | 4-[[[4-[[(3-Chloro-4-methoxyphenyl(methyl]amino]-1-ethyl-1H-pyrazolo[3,4-b]pyridin-5-yl]carbonyl]amino]butanoic acid methyl ester | (METHOD 1B) | 81 | 3.56 | m/z (M + M) 460 |
| 142 | N-[[4-[[(3-Chloro-4-methoxyphenyl)methyl]amino]-1-ethyl-1H-pyrazolo[3,4-b]pyridin-5-yl]carbonyl]-L-alanine ethyl ester | (METHOD 1B) | 83 | 3.73 | m/z (M + H) 460 |

-continued

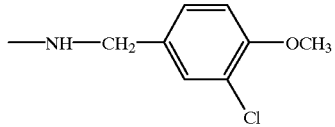

| Ex. | Name | X₂ | PURITY (%) | HPLC (retention time, minutes) | OTHER DATA |
|---|---|---|---|---|---|
| 143 | 4-[[(3-Chloro-4-methoxyphenyl)methyl]amino]-1-ethyl-N-(2-oxo-2-phenylethyl)-1H-pyrazolo[3,4-b]pyridine-5-carboxamide | 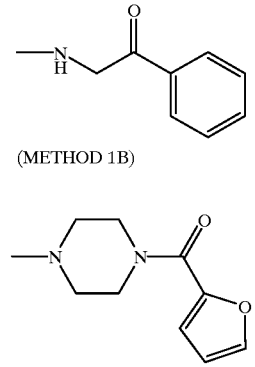<br>(METHOD 1B) | 100 | 3.83 | m/z (M + H) 478 |
| 144 | 1-[[4-[[(3-Chloro-4-methoxyphenyl)methyl]amino]-1-ethyl-1H-pyrazolo[3,4-b]pyridin-5-yl]carbonyl]-4-(2-furanylcarbonyl)piperazine | 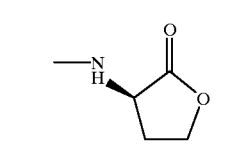<br>(METHOD 1B) | 87 | 3.17 | m/z (M + H) 523 |
| 145 | (S)-4-[[(3-Chloro-4-methoxyphentl)methyl]amino]-1-ethyl-N-(tetrahydro-2-oxo-3-furanyl)-1H-pyrazolo[3,4-b]pyridine-5-carboxamid | 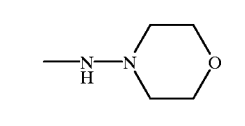<br>(METHOD 1B) | 96 | 3.24 | m/z (M + H) 444 |
| 146 | 4-[[(3-Chloro-4-methoxyphenyl)methyl]amino]-1-ethyl-N-4-morpholinyl-1H-pyrazolo[3,4-b]pyridine-5-carboxamide | 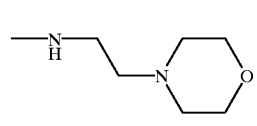<br>(METHOD 1B) | 100 | 3.27 | m/z (M + H) 445 |
| 147 | 4-[[(3-Chloro-4-methoxyphenyl)methyl]amino]-1-ethyl-N-[2-(4-morpholinyl)ethyl-1H-pyrazolo[3,4-b]pyridine-5-carboxamide | 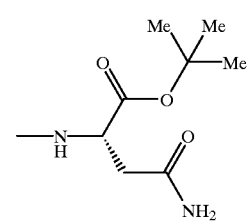<br>(METHOD 1B) | 100 | 2.77 | m/z (M + H) 473 |
| 148 | N-[[4-[[(3-Chloro-4-methoxyphenyl)methyl]amino]-1-ethyl-1H-pyrazolo[3,4-b]pyridin-5-yl]carbonyl]L-asparagine 1,1-dimethylester | <br>(METHOD 1B) | 77 | 3.69 | m/z (M + H) 531 |

-continued

Common structure: —NH—CH$_2$—(phenyl with OCH$_3$ and Cl substituents)

| Ex. | Name | X$_2$ | PURITY (%) | HPLC (retention time, minutes) | OTHER DATA |
|---|---|---|---|---|---|
| 149 | (S)-4-[[(3-Chloro-4-methoxyphenyl)methyl]amino]-1-ethyl-N-[2-oxo-3-[2-oxo-2-(1-pyrrolidinyl)ethyl]cycloheptyl]-1H-pyrazolo[3,4-b]pyrazolo[3,4-b]pyridine-5-carboxamide | (azepanone with pyrrolidinyl ethyl substituent) (METHOD 1B) | 98 | 3.52 | m/z (M + H) 582 |
| 150 | (S)-α-[[[4-[[(3-Chloro-4-methoxyphenyl)methyl]amino]-1-ethyl-1H-pyrazolo[3,4-b]pyridin-5-yl]carbonyl]aino]-4-hydroxybenzeneacetic acid | (CO$_2$H, OH substituted benzyl) (METHOD 1A) | 72 | 3.15 | m/z (M + H) 510 |
| 151 | 4-[[(3-Chloro-4-methoxyphenyl)methyl]amino]-1-ethyl-N-(4-piperidinyl)-1H-pyrazolo[3,4-b]pyridine-5-carboxamide | (4-piperidinyl) (METHOD 1B) | 92 | 2.82 | m/z (M + H) 443 |
| 152 | 4-[[(3-Chloro-4-methoxyphenyl)methyl]amino]-1-ethyl-N-(4-pyridinylmethyl)-1H-pyrazolo[3,4-b]pyridine-5-carboxylate | (4-pyridinylmethyl-O-) METHOD 2 (also made using the procedure of Method 1A) | 95 | 3.15 | m/z (M + H) 452 |
| 153 | 4-[[(3-Chloro-4-methoxyphenyl)methyl]amino]-1-ethyl-N-[3-(4-morpholinyl)ethyl]-1H-pyrazolo[3,4-b]pyridine-5-carboxlyate | (morpholinylethoxy) METHOD 2 | 95 | 2.97 | m/z (M + H 474 |
| 154 | 4-[[(3-Chloro-4-methoxyphenyl)methyl]amino]-1-ethyl-N-(4-pyridinylethyl)-1H-pyrazolo[3,4-b]pyridine-5-carboxamide | (4-pyridinylethylamino) (Method 1A) | 97 | 2.89 | m/z (M + H) 465 |

-continued

[Structure: —NH—CH₂—(phenyl with OCH₃ and Cl)—]

| Ex. | Name | X₂ | PURITY (%) | HPLC (retention time, minutes) | OTHER DATA |
|---|---|---|---|---|---|
| 155 | 4-[[(3-CHloro-4-methoxyphenyl)methyl]amino]-1-ethyl-N-(2-pyridinylethyl)-1H-pyrazolo[3,4-b]pyridine-5-carboxamide | —NH—CH₂CH₂—(2-pyridinyl) (Method 1A) | 90 | 2.90 | m/z (M + H) 465 |
| 156 | 4-[[(3-Chloro-4-methoxyphenyl)methyl]amino]-1-ethyl-N-[3-(1-N-methylpiperizinyl)propyl]-1H-pyrazolo[3,4-b]pyridine-5-carboxamide | —NH—(CH₂)₃—N-methylpiperazinyl (Method 1A) | 98 | 2.60 | m/z (M + H) 500 |
| 157 | (S)-4-[[(3-Chloro-4-methoxyphenyl)methyl]amino]-1-ethyl-N-(2-tetrahydrofurylmethyl)-1H-pyrazolo[3,4-b]pyridine-5-carboxamide | —NH—CH₂—(S-tetrahydrofuran-2-yl) (Method 1A) | 99 | 3.70 | m/z (M + H) 444 |
| 158 | (R)-4-[[(3-Chloro-4-methoxyphenyl)methyl]amino]-1-ethyl-N-(2-tetrahydrofurfylmethyl)-1H-pyrazolo[3,4-b]pyridine-5-carboxamide | —NH—CH₂—(R-tetrahydrofuran-2-yl) (Method 1A) | 94 | 3.6 | m/z (M + H) 444 |
| 159 | 4-[[(3-Chloro-4-methoxyphenyl)methyl)]amino]-1-ethyl-N-[4-(2-chloropyridinylmethyl)]-1H-pyrazolo[3,4-b]pyridine-5-carboxamide | —NH—CH₂—(2-chloropyridin-4-yl) (Method 1A) | 90 | 3.96 | m/z (M + H) 485 |
| 160 | 4-[[(3-Chloro-4-methoxyphenyl)methyl]amino]-1-ethyl-N-[4-(2,6-dichloropyridinylmethyl)]-1H-pyrazolo[3,4-b]pyridine-5-carboxamide | —NH—CH₂—(2,6-dichloropyridin-4-yl) (Method 1A) | 97 | 3.90 | m/z (M + H) 519, 521 |
| 161 | 4-[[(3-Chloro-4-methoxyphenyl)methyl]amino]-1-ethyl-N-(5-tetrazoyl)-1H-pyrazolo[3,4-b]pyridine-5-carboxamide | —NH—(tetrazol-5-yl) (Method 1A) | 83 | 3.10 | m/z (M + H) |

-continued (structure: —NH—CH₂— attached to phenyl ring with —OCH₃ and Cl substituents)

| Ex. | Name | X₂ | PURITY (%) | HPLC (retention time, minutes) | OTHER DATA |
|---|---|---|---|---|---|
| 162 | 4-[[(3-Chloro-4-methoxyphenyl)methyl]amino]-1-ethyl-N-[4-(morpholinylethyl)]-1H-pyrazolo[3,4-b]pyridine-5-carboxylate | (morpholinylethoxy group) (Method 1A) | 85 | 3.00 | m/z (M + H) 474 |
| 163 | 4-[N-(methylpropylate)amino]-1-ethyl-N-(4-pyridinylmethyl)-1H-pyrazolo[3,4-b]pyridine-5-carboxamide | —NH—CH₂—(3-pyridyl) (Method 3) | 88 | 1.90 | m/z (M + H) 397 |
| 164 | 4-[[(3-Chloro-4-methoxyphenyl)methyl]amino]-1-ethyl-N-(2-pyridinylmethyl)-1H-pyrazolo[3,4-b]pyridine-5-craboxylate | —O—CH₂—(2-pyridyl) (Method 2) | 95 | 3.40 | m/z (M + H) 452 |

The following compounds of formula II were prepared wherein R₃ is ethyl, R₄ is hydrogen, Y is nitrogen, and Z is CH₂:

| Ex. | Name | E₂ | X₂ | PURITY (%) | HPLC (retention time, minutes) | OTHER DATA |
|---|---|---|---|---|---|---|
| 165 | 4-[[(3-Fluoro-4-methoxyphenyl)methyl]amino]-1-ethyl-N-(4-pyridinylmethyl)-1H-pyrazolo[3,4-b]pyridine-5-carboxamide | (3-fluoro-4-methoxybenzyl)NH— | —NH—CH₂—(4-pyridyl) Method 2 | 97 | 2.65 | m/z (M + H) 435 |
| 166 | 4-[[(3,5-Dichloro-4-methoxyphenyl)methyl]amino]-1-ethyl-N-(4-pyridinylmethyl)-1H-pyrazolo[3,4-b]pyridine-5-carboxamide | (3,5-dichloro-4-methoxybenzyl)NH— | —NH—CH₂—(4-pyridyl) Method 2 | 98 | 3.18 | m/z (M + H) 486 |

| Ex. | Name | E₂ | X₂ | PURITY (%) | HPLC (retention time, minutes) | OTHER DATA |
|---|---|---|---|---|---|---|
| 167 | 4-[[(4-Fluorophenyl)methyl]amino]-1-ethyl-N-(4-pyridinylmethyl)-1H-pyrazolo[3,4-b]pyridine-5-carboxamide | —NH—CH₂—C₆H₄—F | —NH—CH₂-(4-pyridyl) Method 2 | 99 | 2.67 | m/z (M + H) 405 |
| 168 | 4-[[(4-Methoxy)butyl]amino]1-ethyl-N-(4-pyridinylmethyl)-1H-pyrazolo[3,4-b]pyridine-5-carboxamide | —NH—(CH₂)₄—O—Me | —NH—CH₂-(4-pyridyl) Method 2 | 98 | 2.20 | m/z (M + H) 383 |
| 169 | 4-[[(N,N'-3-Dimethylamino)propyl]amino]-1-ethyl-N-(4-pyridinylmethyl)-1H-pyrazolo[3,4-b]pyridine-5-carboxamide | —NH—(CH₂)₃—N(Me)₂ | —NH—CH₂-(4-pyridyl) Method 2 | 95 | 0.93 | m/z (M + H) 382 |
| 170 | 4-[(1,3-Benzodioxol-5-ylmethyl)amino]-1-ethyl-N-[3-(2-oxo-1-pyrrolidinyl)propyl]-1H-pyrazolo[3,4-b]pyridine-5-0 carboxamide | —NH—CH₂-(1,3-benzodioxol-5-yl) | —NH—(CH₂)₃-(2-oxo-1-pyrrolidinyl) | 91 | 3.07 | m/z (M + H) 465 |

The following compounds of formula III were prepared wherein R³ is ethyl, R₄ is hydrogen, Y is nitrogen, Z is CH₂, and E₁ is

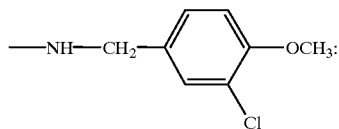
—NH—CH₂—C₆H₃(Cl)(OCH₃):

| Ex. | Name | X₃ | PURITY (%) | HPLC (retention time, minutes) | OTHER DATA |
|---|---|---|---|---|---|
| 171 | 4-[[(3-Chloro-4-methoxyphenyl)-methyl]amino]-1-ethyl-N-(6-hydroxyhexyl)-1H-pyrazolo[3,4-b]pyridine-5- | —NH—(CH₂)₆—OH (METHOD 1A) | 97 | 3.40 | mp 117–118° C.; NMR C¹³H¹ m/z (M + H) 460. |

| Ex. | Name | X₃ | PURITY (%) | HPLC (retention time, minutes) | OTHER DATA |
|---|---|---|---|---|---|
| 172 | 4-[[(3-Chloro-4-methoxyphenyl)-methyl]amino]-N-[4-(diethyl-amino)-1-methylbutyl]-1-ethyl-1H-pyrazolo[3,4-b]pyridine-5-carboxamide | (METHOD 1B) | 95 | 3.03 | m/z (M + H) 501 |
| 173 | N-[2-[Bis(1-methylethyl)amino]-ethyl]-4-[[(3-chloro-4-methoxyphenyl)methyl]amino]-1-ethyl-1H-pyrazolo[3,4-b]pyridine-5-carboxamide | (METHOD 1B) | 85 | 3.06 | m/z (M + H) 487 |
| 174 | 4-[[(3-Chloro-4-methoxyphenyl)-methyl]amino]-N-[2,2-dimethyl-3-(dimethylamino)propyl]-1-ethyl-1H-pyrazolo[3,4-b]pyridine-5-carboxamide | (METHOD 1B) | 95 | 2.85 | m/z (M + H) 473 |
| 175 | 4-[[(3-Chloro-4-methoxyphenyl)-methyl]amino]-1-ethyl-N-[1-(methoxymethyl)propyl]-1H-pyrazolo[3,4-b]pyridine-5-carboxamide | (METHOD 1B) | 100 | 3.67 | m/z (M + H) 446 |
| 176 | 4-[[(3-Chloro-4-methoxyphenyl)-methyl]amino]-1-ethyl-N-[3-(1-methylethoxy)propyl]-1H-pyrazolo[3,4-b]pyridine-5-carboxamide | (METHOD 1B) | 83 | 3.9 | m/z (M + H) 460 |
| 177 | 4-[[(3-Chloro-4-methoxyphenyl)-methyl]amino]-1-ethyl-N-(4-methoxybutyl)-1H-pyrazolo[3,4-b]-pyridine-5-carboxamide | (METHOD 1B) | 100 | 3.64 | m/z (M + H) 446 |
| 178 | (R)-1-[[4-[[(3-Chloro-4-methoxy-phenyl)methyl]amino]-1-ethyl-1H-pyrazolo[3,4-b]pyridin-5-yl]-carbonyl]-3-(dimethylamino)-pyrrolidine | (METHOD 1B) | 99 | 2.41 | m/z (M + H) 457 |

-continued

| Ex. | Name | X₃ | PURITY (%) | HPLC (retention time, minutes) | OTHER DATA |
|---|---|---|---|---|---|
| 179 | (S)-1-[[4-[[(3-Chloro-4-methoxy-phenyl)methyl]amino]-1-ethyl-1H-pyrazolo[3,4-b]pyridin-5-yl]-carbonyl]-3-(dimethylamino)-pyrrolidine | 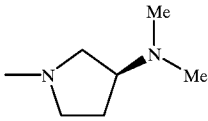 (METHOD 1B) | 88 | 2.40 | m/z (M + H) 457 |
| 180 | 4-[[(3-Chloro-4-methoxyphenyl)-methyl]amino]-1-ethyl-N-methoxy-1H-pyrazolo[3,4-b]pyridine-5-carboxamide | 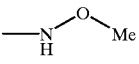 (METHOD 1B) | 89 | 3.38 | m/z (M + H) 390 |
| 181 | 4-[[(3-Chloro-4-methoxyphenyl)-methyl]amino]-N-[2-(dimethyl-amino)ethyl]-1-ethyl-1H-pyrazolo-[3,4-b]pyridine-5-carboxamide | 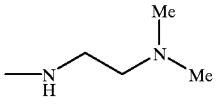 (METHOD 1B) | 96 | 2.78 | m/z (M + H) 431 |
| 182 | 1-[[4-[[(3-Chloro-4-methoxy-phenyl)methyl]amino]-1-ethyl-1H-pyrazolo[3,4-b]pyridin-5-yl]-carbonyl]-4-methylpiperazine | 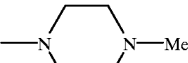 (METHOD 1B) | 97 | 2.53 | m/z (M + H) 443 |
| 183 | 4-[[(3-Chloro-4-methoxyphenyl)-methyl]amino]-1-ethyl-N-(3-hydroxypropyl)-1H-pyrazolo[3,4-b]pyridine-5-carboxamide | 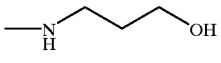 (METHOD 1B) | 94 | 3.01 | m/z (M + H) 418 |
| 184 | 4-[[(3-Chloro-4-methoxyphenyl)-methyl]amino]-1-ethyl-N-(4-hydroxybutyl)-1H-pyrazolo[3,4-b]pyridine-5-carboxamide | 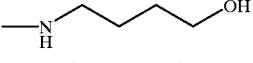 (METHOD 1B) | 94 | 3.11 | m/z (M + H) 432 |
| 185 | 4-[[(3-Chloro-4-methoxyphenyl)-methyl]amino]-1-ethyl-N-(5-hydroxypentyl)-1H-pyrazolo[3,4-b]pyridine-5-carboxamide | 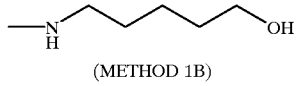 (METHOD 1B) | 88 | 3.22 | m/z (M + H) 446 |
| 186 | 4-[[(3-Chloro-4-methoxyphenyl)-methyl]amino]-1-ethyl-N-(2-hydroxyethyl)-1H-pyrazolo[3,4-b]pyridine-5-carboxamide | 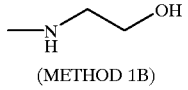 (METHOD 1B) | 97 | 2.9 | m/z (M + H) 404 |
| 187 | 4-[[(3-Chloro-4-methoxyphenyl)-methyl]amino]-1-ethyl-N-(4-hydroxypiperidinyl)-1H-pyrazolo[3,4-b]pyridine-5-carboxamide | 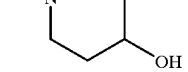 (METHOD 1A) | 97 | 2.80 | m/z (M + H) 444 |
| 188 | 4-[[(3-Chloro-4-methoxyphenyl)-methyl]amino]-1-ethyl-N-[3-(1,2-dihydroxypropyl)]-1H-pyrazolo[3,4-b]pyridine-5-carboxamide | 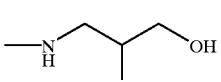 (METHOD 1A) | 95 | 2.97 | m/z (M + H) 434 |

What is claimed is:
1. A compound having the formula (I), formula (II), or formula (III):

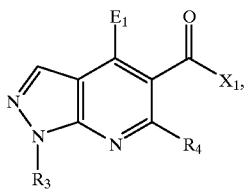
(I)

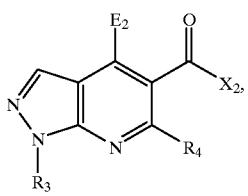
(II)

or

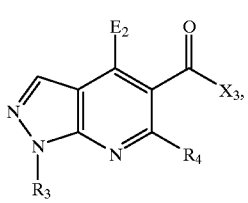
(III)

or a pharmaceutically acceptable salt thereof, wherein:
$E_1$ is

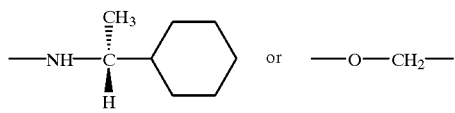

disubstituted phenyl;
$E_2$ is —NH—CH$_2$-disubstituted phenyl;
the term "disubstituted phenyl" refers to a phenyl ring having two substituents independently selected from halogen and alkoxy or wherein said disubstituted phenyl is

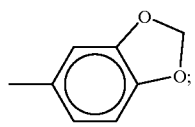

$X_1$ is —O—A$_1$-heterocyclo, —O—A$_1$-heteroaryl, —NH—A$_2$—R$_2$, or

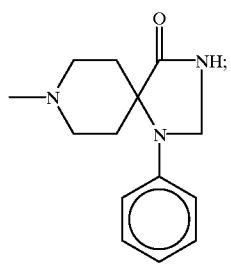

$X_2$ is —O—A$_1$-heterocyclo, —O—A$_1$-heteroaryl, NH—A$_2$—R$_{25}$, or

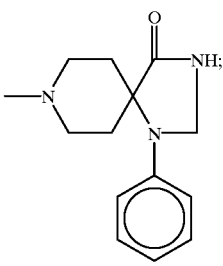

$X_3$ is —O—R$_9$, —O—A$_1$—O—R$_9$, —N(R$_9$)(R$_{10}$),

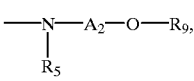

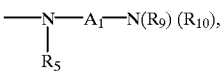

or a monocyclic ring

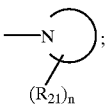

$R_3$ is hydrogen, alkyl, cycloalkyl, substituted cycloalkyl, substituted alkyl, —A$_1$-aryl, —A$_1$-substituted aryl, —A$_1$-cycloalkyl, or —A$_1$-substituted cycloalkyl;
$R_4$ is hydrogen, —N(R$_{12}$)(R$_{13}$), —OR$_{12}$ or 1- or 3-imidazolyl;
$A_1$ is an alkylene or substituted alkylene bridge of 1 to 10 carbons;
$A_2$ is a direct bond, an alkylene or substituted alkylene bridge of 1 to 10 carbons, an alkenyl or substituted alkenyl bridge of 2 to 10 carbons having one or more double bonds, or an alkynyl or substituted alkynyl bridge of 2 to 10 carbons having one or more triple bonds;
$R_2$ is cycloalkyl, substituted cycloalkyl, aryl, substituted aryl, heterocyclo, heteroaryl, cycloalkyl-A$_3$-cycloalkyl, cycloalkyl-A$_3$-substituted cycloalkyl, cycloalkyl-A$_3$-aryl, cycloalkyl-A$_3$-substituted aryl, cycloalkyl-A$_3$-heterocyclo, cycloalkyl-A$_3$-heteroaryl, substituted cycloalkyl-A$_3$-cycloalkyl, substituted cycloalkyl-A$_3$-substituted cycloalkyl, substituted cycloalkyl-A$_3$-aryl, substituted cycloalkyl-A$_3$-substituted aryl, substituted cycloalkyl-A$_3$-heterocyclo, substituted cycloalkyl-A$_3$-heteroaryl, aryl-A$_3$-cycloalkyl, aryl-A$_3$-substituted cycloalkyl, aryl-A$_3$-aryl, aryl-A$_3$-substituted aryl, aryl-A$_3$-heterocyclo, aryl-A$_3$-heteroaryl, substituted aryl-A$_3$-cycloalkyl, substituted aryl-A$_3$-substituted cycloalkyl, substituted aryl-A$_3$-aryl, substituted aryl-A$_3$-substituted aryl, substituted aryl-A$_3$-heterocyclo, substituted aryl-A$_3$-heteroaryl, heterocyclo-A$_3$-cycloalkyl, heterocyclo-A$_3$-substituted cycloalkyl, heterocyclo-A$_3$-aryl, heterocyclo-A$_3$-substituted aryl, heterocyclo-A$_3$-heterocyclo, heterocyclo-A$_3$-heteroaryl, heteroaryl-A$_3$-cycloalkyl, heteroaryl-A$_3$-substituted cycloalkyl, heteroaryl-A$_3$-aryl, heteroaryl- $A_3$-heterocyclo, heteroaryl-$A_3$-heteroaryl, cyano, —$OR_9$, —$SR_9$, —(C=O)$R_9$, —N($R_9$)($R_{10}$), —$CO_2R_9$, —(C=O)N($R_{12}$)($R_{13}$), —$SO_2$N($R_{12}$)($R_{13}$), —$NR_{11}$(C=O)$R_{19}$, —$NR_{11}$(C=O)N($R_{12}$)($R_{13}$), —O—(C=O)N($R_{12}$)($R_{13}$) provided that $A_2$ is not a direct bond, —$NR_{11}CO_2R_{19}$, —(C=O)N($R_{11}$)$CH_2CO_2R_{19}$, nitrogen when $A_2$ is alkynyl ending in a triple bond, or NH when $A_2$ is alkenyl ending in a double bond;

$R_{25}$ is cycloalkyl, substituted cycloalkyl, aryl, substituted aryl, heterocyclo, heteroaryl, cycloalkyl-$A_3$-cycloalkyl, cycloalkyl-$A_3$-substituted cycloalkyl, cycloalkyl-$A_3$-aryl, cycloalkyl-$A_3$-substituted aryl, cycloalkyl-$A_3$-heterocyclo, cycloalkyl-$A_3$-heteroaryl, subsituted cycloalkyl-$A_3$-cycloalkyl, substituted cycloalkyl-$A_3$-substituted cycloalkyl, substituted cycloalkyl-$A_3$-aryl, substituted cycloalkyl-$A_3$-substituted aryl, substituted cycloalkyl-$A_3$-heterocyclo, substituted cycloalkyl-$A_3$-heteroaryl, aryl-$A_3$-cycloalkyl, aryl-$A_3$-substituted cycloalkyl, aryl-$A_3$-aryl, aryl-$A_3$-substituted aryl, aryl-$A_3$-heterocyclo, aryl-$A_3$-heteroaryl, substituted aryl-$A_3$-cycloalkyl, substituted aryl-$A_3$-substituted cycloalkyl, substituted aryl-$A_3$-aryl, substituted aryl-$A_3$-substituted aryl, substituted aryl-$A_3$-heterorycio, substituted aryl-$A_3$-heteroaryl, heterocyclo-$A_3$-cycloalkyl, heterocyclo-$A_3$-substituted cycloalkyl, heterocyclo-$A_3$-aryl, heterocyolo-$A_3$-substituted aryl, heterocyclo-$A_3$-heterocyclo, heterocyclo-$A_3$-heteroaryl, heteroaryl-$A_3$-cycloalkyl, heteroaryl-$A_3$-substituted cycloalkyl; heteroaryl-$A_3$-aryl, heteroaryl-$A_3$-substituted aryl, heteroaryl-$A_3$-heterocyclo, heteroaryl-$A_3$-heteroaryl, cyano, —S—$R_9$, —(C=O)$R_{11}$, —$CO_2R_{19}$, —(C=O)N($R_{12}$)($R_{13}$), —$SO_2$N($R_{12}$)($R_{13}$), —$NR_9$(C=O)$R_{10}$, —$NR_{11}$(C=O)N($R_{12}$)($R_{13}$), —O—(C=O)N($R_{12}$)($R_{13}$) provided that $A_2$ is not a direct bond, —$NR_{11}CO_2R_{19}$, —(C=O)N($R_{11}$)$CH_2CO_2R_{19}$, nitrogen when $A_2$ is alkynyl ending in a triple bond, or NH when $A_2$ is alkenyl ending in a double bond;

$A_3$ is a direct bond, an alkylene or substituted alkylene bridge of 1 to 10 carbons, an alkenyl or substituted alkenyl bridge of 2 to 10 carbons having one or more double bonds, an alkynyl or substituted alkynyl bridge of 2 to 10 carbons having one or more triple bonds, —$(CH_2)_d$—O—$(CH_2)_e$—, —$(CH_2)_d$—S—$(CH_2)_e$—, or —$(CH_2)_d$—(C=O)—$(CH_2)_e$—;

d is zero or an integer from 1 to 6;

e is zero or an integer from 1 to 6;

$R_5$ is hydrogen, alkyl, substituted alkyl, cycloalkyl, substituted cycloalkyl, aryl, —$A_1$-aryl, substituted aryl, —$A_1$-substituted aryl, heterocyclo, —$A_1$-heterocyclo, heteroaryl or —$A_1$-heteroaryl;

$R_9$, $R_{10}$, $R_{11}$, $R_{12}$, $R_{13}$, and $R_{19}$ are independently selected from the group consisting of hydrogen, alkyl, substituted alkyl, cycloalkyl, substituted cycloalkyl, aryl, substituted aryl, heterocyclo, heteroaryl, —$A_1$-cycloalkyl, —$A_1$-substituted cycloalkyl, —$A_1$-aryl, —$A_1$-subsituted aryl, —$A_1$-heterocyclo and —$A_1$-heteroaryl, or $R_{12}$ and $R_{13}$ taken together with the N atom to which they are attached represent a heterocyclo ring;

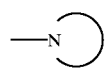

represents a monocyclic heterocyclo or heteroaryl ring of 4 to 8 atoms containing up to 3 additional heteroatoms (up to 2 additional heteroatoms when the ring is 4 atoms) which are selected from one or two oxygen atoms and/or one or two sulfur atoms and/or one, two or three nitrogen atoms;

$R_{21}$ is attached to an available carbon or nitrogen atom and is hydrogen, alkyl, halogen, hydroxy, trifluoromethyl, amino, alkoxy or carboxy; and n is one or two.

2. A compound of claim 1 or a pharmaceutically acceptable salt thereof wherein:

$R_3$ is straight or branched chain alkyl of 1 to 4 carbons;

$R_4$ is hydrogen;

$R_5$ is hydrogen, alkyl, —$A_1$-phenyl, or —$A_1$-heteroaryl wherein alkyl is straight or branched chain of 1 to 4 carbons;

$R_2$ is —(C=O)$R_9$, —S—$R_9$, —O—$R_9$, —N($R_9$)($R_{10}$), —$NR_{11}CO_2R_{19}$, —(C=O)N($R_{11}$)$CH_2CO_2R_{19}$, —$NR_{11}$(C=O)$R_{19}$, —$CO_2R_9$, nitrogen when $A_2$ is alkynyl ending in a triple bond, —(C=O)N($R_{12}$)($R_{13}$), phenyl, substituted phenyl, cycloalkyl, heterocyclo, heteroaryl, cycloalkyl-$A_3$-phenyl, phenyl-$A_3$-heteroaryl, heterocyclo-$A_3$-phenyl, or heterocyclo-$A_3$-heterocyclo;

$R_{25}$ is —S—$R_9$, —$NR_{11}CO_2R_{19}$, nitrogen when $A_2$ is alkynyl ending in a triple bond, —(C=O)N($R_{11}$)$CH_2CO_2R_{19}$, —$NR_9$(C=O)$R_{10}$, —$CO_2R_{19}$, —(C=O)N($R_{12}$)($R_{13}$), phenyl, substituted phenyl, cycloalkyl, heterocyclo, heteroaryl, cycloalkyl-$A_3$-phenyl, heterocyclo-$A_3$-phenyl, phenyl-$A_3$-heteroaryl or heterocyclo-$A_3$-heterocyclo;

$A_1$ is an alkylene or substituted alkylene bridge of 1 to 6 carbons wherein said substituent is a straight or branched chain alkyl of 1 to 4 carbons;

$A_2$ is a direct bond, an alkylene or substituted alkylene bridge of 1 to 6 carbons wherein said substituent is one or two members selected from alkyl, phenyl, substituted phenyl, —$CO_2$-alkyl, carboxy, hydroxy, —NH—(C=O)-alkyl, and —$CH_2$—(C=O)—$NH_2$, an alkenyl bridge of 2 to 4 carbons having one double bond, or an alkynyl bridge of 2 to 3 carbons having one triple bond wherein alkyl is straight or branched chain of 1 to 4 carbons;

the term "heterocyclo" refers to a substituted or unsubstituted fully saturated or partially saturated 5 to 7 membered monocyclic ring containing one or two heteroatoms selected from oxygen, sulfur and nitrogen and bicyclic rings wherein the monocyclic ring as defined above is fused to a phenyl or substituted phenyl or wherein a bridge of 2 or 3 carbons is present between available carbon and nitrogen atoms, said nitrogen and sulfur atoms may optionally be oxidized and said nitrogen atom may optionally be quaternized; said heterocyclo group may be attached at any available nitrogen or carbon atom, and said heterocyclo ring may contain one or two substituents attached to an available carbon or nitrogen atom selected from alkyl, keto and —$CO_2$-alkyl, wherein alkyl is straight or branched chain of 1 to 4 carbons;

the term "heteroaryl" refers to a substituted or unsubstituted aromatic 5 or 6 membered monocyclic ring containing one or two oxygen or sulfur atoms and/or from one to four nitrogen atoms provided that the total number of heteroatoms in the ring is four or less, and bicyclic rings wherein the monocyclic ring as defined above is fused to a phenyl or substituted phenyl, said nitrogen and sulfur atoms may optionally be oxidized and said nitrogen atom may optionally be quaternized, said heteroaryl group may be attached at any available nitrogen or carbon atom, and said heteroaryl ring may contain one or two substituents attached to an available carbon or nitrogen atom selected from straight or branched chain alkyl of 1 to 4 carbons and halo;

the term "cycloalkyl" refers to a fully saturated cyclic hydrocarbon group of 3 to 7 carbons and such cycloalkyl rings fused to a phenyl ring or such cycloalkyl rings of 5 to 7 carbons having a carbon-carbon bridge of 3 or 4 carbons;

the term "substituted phenyl" refers to a phenyl ring having one, two, or three substituents selected from alkyl, halo, hydroxy, trifluoromethyl, alkoxy of 1 to 4 carbons, —N(alkyl)$_2$, and SO$_2$NH$_2$ wherein the alkyl is straight or branched chain of 1 to 4 carbons; and a phenyl ring substituted with a fused five membered ketal;

$R_9$, $R_{10}$, $R_{11}$, $R_{12}$, $R_{13}$, and $R_{19}$ are independently selected from the group consisting of hydrogen, straight or branched chain alkyl of 1 to 4 carbons, phenyl, substituted phenyl and —$A_1$-phenyl;

$A_3$ is a direct bond, an alkylene bridge of 1 to 6 carbons, or

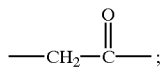

is a 5 to 7 membered heterocyclo ring which can contain an additional nitrogen atom or can contain an oxygen or sulfur atom; and $R_{21}$ is attached to an available carbon or nitrogen atom and is hydrogen, straight or branched chain alkyl of 1 to 4 carbons, hydroxy or amino.

3. A compound of claim 2 or a pharmaceutically acceptable salt thereof wherein;

$E_1$ is

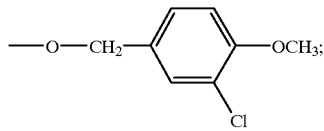

and $E_2$ is

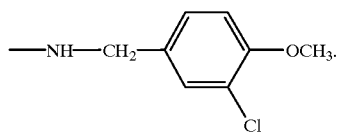

4. A compound of claim 2 or a pharmaceutically acceptable salt thereof wherein:

$X_1$ and $X_2$ are independently selected from the group consisting of

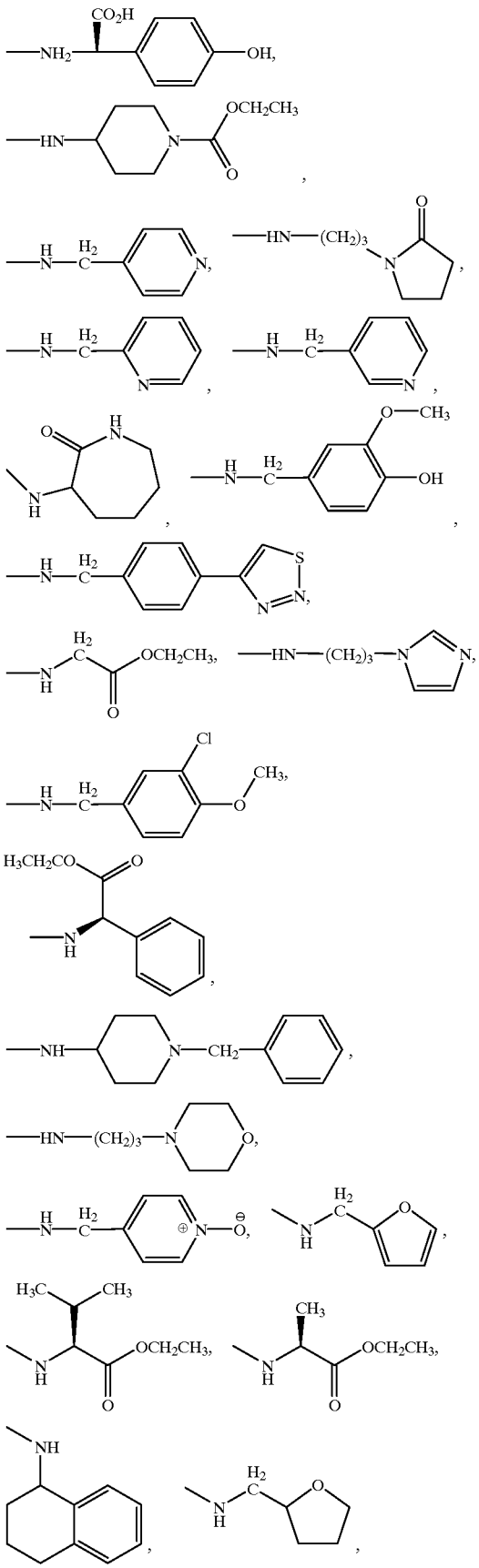

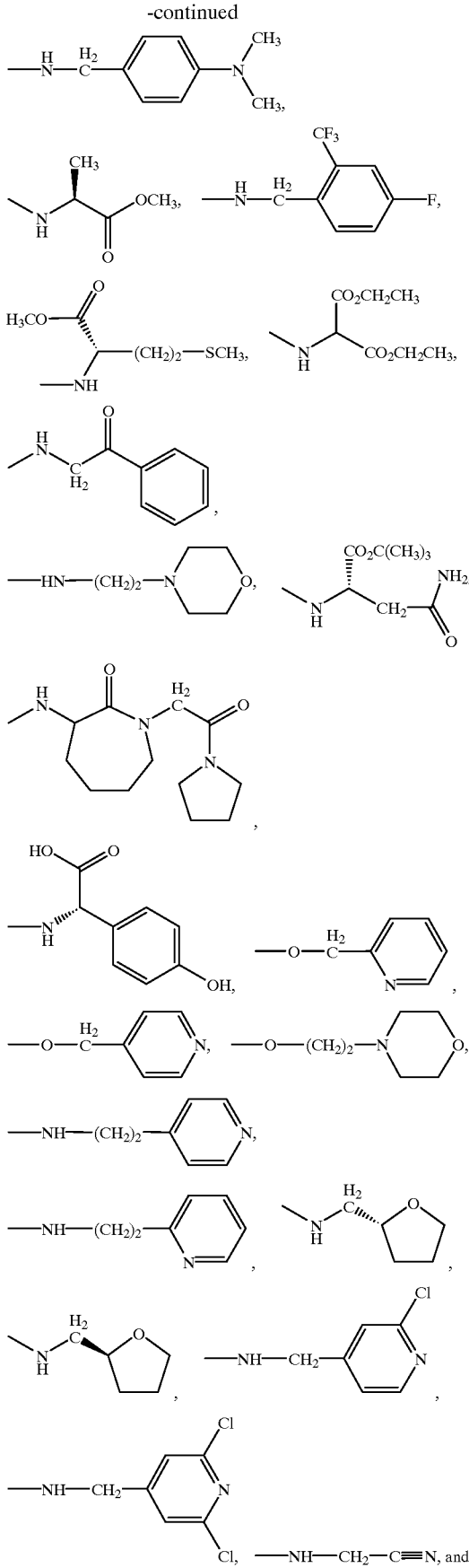
—NH—(CH₂)₃—CO₂CH₃.
5. The compound of claim 1 or a pharmaceutically acceptable salt thereof having the formula (I) wherein:
$E_1$ is —O—CH₂—(3-Cl,4-OCH₃-phenyl); and
$X_1$ is —NH—CH₂—(4-pyridyl).
6. The compound of claim 1 or a pharmaceutically acceptable salt thereof having the formula (II) wherein:
$E_2$ is —NH—CH₂—(3-Cl,4-OCH₃-phenyl); and
$X_2$ is —NH—CH(CO₂H)—(4-OH-phenyl),
and other substituents as depicted.

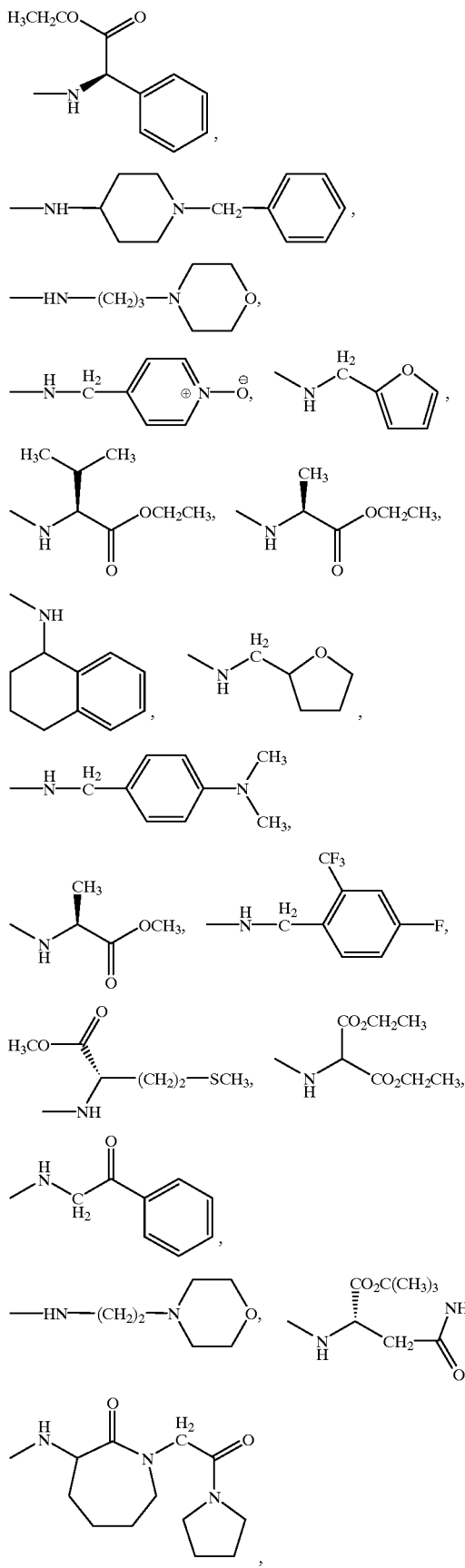

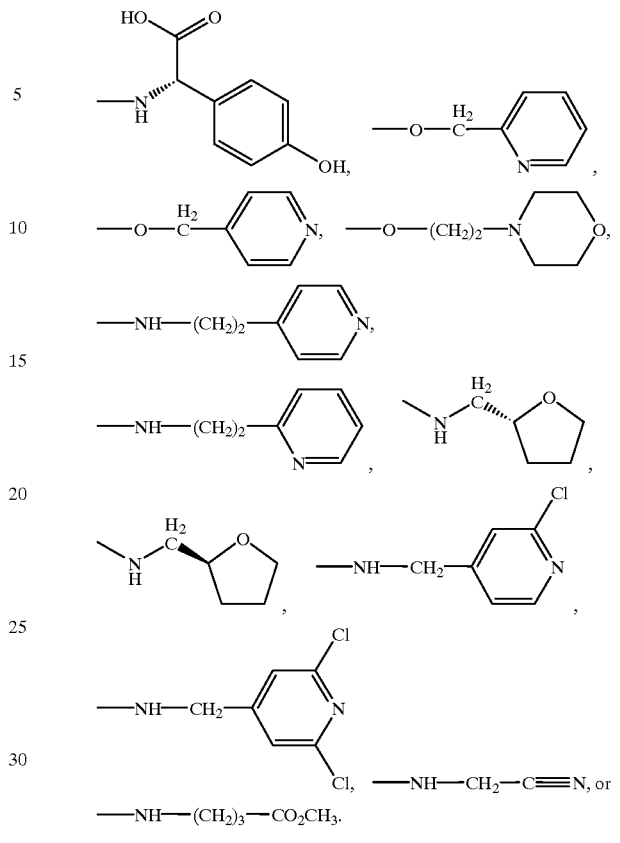

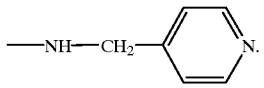

—NH—(CH₂)₃—CO₂CH₃.

7. The compound of claim 6 or a pharmaceutically acceptable salt thereof wherein:

$X_2$ is

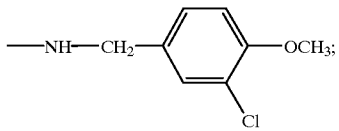

8. The compound of claim 1 or a pharmaceutically acceptable salt thereof having the formula (III) wherein:

$E_2$ is

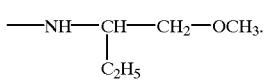

and $X_3$ is

—NH—CH(C₂H₅)—CH₂—OCH₃.

9. The compound of claim 1 or a pharmaceutically acceptable salt thereof wherein $R_3$ is ethyl and $R_4$ is hydrogen.

10. A compound having the formula (I), formula (II), or formula (III):

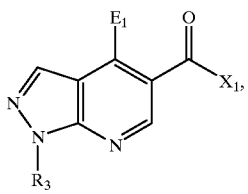
(I)

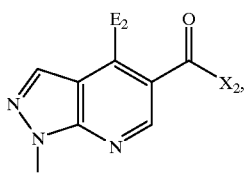
(II)

or

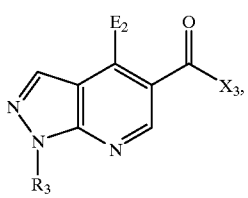
(III)

or a pharmaceutically acceptable salt thereof, wherein:
$E_1$ is

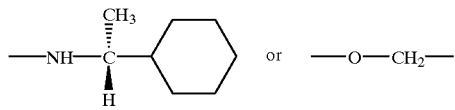

disubstituted phenyl;
$E_2$ is —NH—CH$_2$-disubstituted phenyl;
the term "disubstituted phenyl" refers to a phenyl ring having two substituents independently selected from halogen and alkoxy or wherein said disubstituted phenyl is

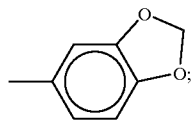

$X_1$ is —O—A$_1$-heterocyclo, —O—A$_1$-heteroaryl, —NH—A$_2$—R$_2$, or

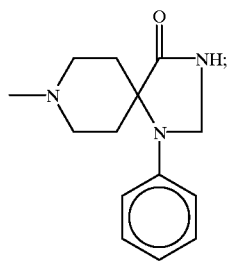

$X_2$ is —O—A$_1$-heterocyclo, —O—A$_1$-heteroaryl, NH—A$_2$—R$_{25}$, or

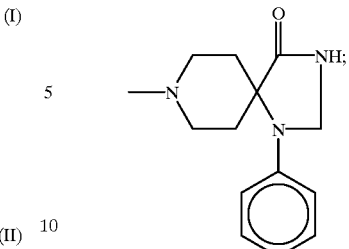

$X_3$ is —O—R$_9$, —O—A$_1$—O—R$_9$, —N(R$_9$)(R$_{10}$),

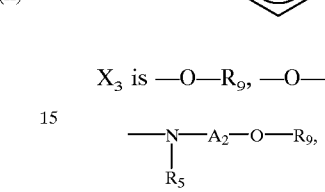

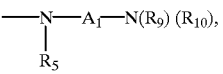

or a monocyclic ring

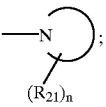

R$_3$ is alkyl of 1 to four carbons;
A$_1$ is an alkylene or substituted alkylene bridge of 1 to 6 carbons;
A$_2$ is a direct bond, an alkylene or substituted alkylene bridge of 1 to 6 carbons, or an alkenylene or substituted alkenylene bridge of 2 to 10 carbons having one or more double bonds;
R$_2$ is —(C=O)R$_9$, —S—R$_9$, —O—R$_9$, —N(R$_9$)(R$_{10}$), —NR$_{11}$CO$_2$R$_{19}$, —(C=O)N(R$_{11}$)CH$_2$CO$_2$R$_{19}$, —NR$_{11}$(C=O)R$_{19}$, —CO$_2$R$_9$, nitrogen when A$_2$ is alkynyl ending in a triple bond, —(C=O)N(R$_{12}$)(R$_{13}$), phenyl, substituted phenyl, cycloalkyl, heterocyclo, heteroaryl, cycloalkyl-A$_3$-phenyl, phenyl-A$_3$-heteroaryl, heterocyclo-A$_3$-phenyl, or heterocyclo-A$_3$-heterocyclo;
R$_{25}$ is —S—R$_9$, —NR$_{11}$CO$_2$R$_{19}$, nitrogen when A$_2$ is alkynyl ending in a triple bond, —(C=O)N(R$_{11}$)CH$_2$CO$_2$R$_{19}$, —NR$_{11}$(C=O)R$_{10}$, —CO$_2$R$_{19}$, —(C=O)N(R$_{12}$)(R$_{13}$), phenyl, substituted phenyl, cycloalkyl, heterocyclo, heteroaryl, cycloalkyl-A$_3$-phenyl, heterocyclo-A$_3$-phenyl, phenyl-A$_3$-heteroaryl or heterocyclo-A$_3$-heterocyclo;
R$_5$ is hydrogen, alkyl, substituted alkyl, cycloalkyl, substituted cycloalkyl, aryl, —A$_1$-aryl, substituted aryl, —A$_1$-substituted aryl, heterocyclo, —A$_1$-heterocyclo, heteroaryl or —A$_1$-heteroaryl;
R$_9$, R$_{10}$, R$_{11}$, R$_{12}$, R$_{13}$, and R$_{19}$ are independently selected from the group consisting of hydrogen, alkyl, substituted alkyl, cycloalkyl, substituted cycloalkyl, aryl, substituted aryl, heterocyclo, heteroaryl, —A$_1$-cycloalkyl, —A$_1$-substituted cycloalkyl, —A$_1$-aryl, —A$_1$-subsituted aryl, —A$_1$-heterocyclo and —A$_1$-heteroaryl, or R$_{12}$ and R$_{13}$ taken together with the N atom to which they are attached represent a heterocyclo ring;

$A_3$ is a direct bond, an alkylene bridge of 1 to 6 carbons, or

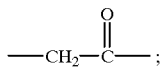

represents a monocyclic heterocyclo or heteroaryl ring of 4 to 8 atoms containing up to 3 additional heteroatoms (up to 2 additional heteroatoms when the ring is 4 atoms) which are selected from one or two oxygen atoms and/or one or two sulfur atoms and/or one, two or three nitrogen atoms;

$R_{21}$ is attached to an available carbon or nitrogen atom and is hydrogen, alkyl, halogen, hydroxy, trifluoromethyl, amino, alkoxy or carboxy; and n is one or two.

11. The compound of claim 10 or a pharmaceutically acceptable salt thereof wherein $E_1$ is

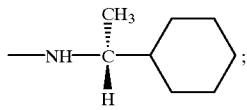

and $E_2$ is —NH—$CH_2$-disubstituted phenyl.

12. The compound of claim 10 or a pharmaceutically acceptable salt thereof wherein $R_3$ is ethyl.

13. A compound selected from the group consisting of;

4-[[[4-[[(3-chloro-4-methoxyphenyl)methyl]amino]-1-ethyl-1H-pyrazolo[3,4-b]pyridin-5-yl]carbonyl]amino]-1-piperidinecarboxylic acid, ethyl ester;

4-[[(3-chloro-4-methoxyphenyl)methyl]amino]-1-ethyl-N-[3-(2-oxo-1-pyrrolidinyl)propyl]-1H-pyrazolo[3,4-b]pyridine-5-carboxamide;

4-[[(3-chloro-4-methoxyphenyl)methyl]amino]-1-ethyl-N-(2-pyridinylmethyl)-1H-pyrazolo[3,4-b]pyridine-5-carboxamide;

4-[[(3-chloro-4-methoxyphenyl)methyl]amino]-1-ethyl-N-(3-pyridinylmethyl)-1H-pyrazolo[3,4-b]pyridine-5-carboxamide;

4-[[(3-chloro-4-methoxyphenyl)methyl]amino]-1-ethyl-N-(4-pyridinylmethyl)-1H-pyrazolo[3,4-b]pyridine-5-carboxamide;

4-[[(3-chloro-4-methoxyphenyl)methyl]amino]-1-ethyl-N-[(4-hydroxy-3-methoxyphenyl)methyl-]1H-pyrazolo[3,4-b]pyridine-5-carboxamide;

4-[[(3-chloro-4-methoxyphenyl)methyl]amino]-1-ethyl-N-[[4-(1,2,3-thiadiazol-4-yl)phenyl]methyl]-1H-pyrazolo[3,4-b]pyridine-5-carboxamide;

N-[[4-[[(3-chloro-4-methoxyphenyl)methyl]amino]-1-ethyl-1H-pyrazolo[3,4-b]pyridine-5-yl]carbonyl]glycine, ethyl ester;

4-[[(3-chloro-4-methoxyphenyl)methyl]amino]-1-ethyl-N-(3-1H-imidazol-1-ylpropyl)-1H-pyrazolo[3,4-b]pyridine-5-carboxamide;

N-[(3-chloro-4-methoxyphenyl)methyl]-4-[[(3-chloro-4-methoxyphenyl)methyl]amino]-1-ethyl-1H-pyrazolo[3,4-b]pyridine-5-carboxamide;

(R)-α-[[4-[[(3-chloro-4-methoxyphenyl)methyl]amino]-1-ethyl-1H-pyrazolo[3,4-b]pyridin-5-yl]carbonyl]amino]benzeneacetic acid, ethyl ester;

4-[[(3-chloro-4-methoxyphenyl)methyl]amino]-1-ethyl-N-[1-(phenylmethyl)-4-piperidinyl]-1H-pyrazolo[3,4-b]pyridine-5-carboxamide;

4-[[(3-chloro-4-methoxyphenyl)methyl]amino]-1-ethyl-N-[3-(4-morpholinyl)propyl]-1H-pyrazolo[3,4-b]pyridine-5-carboxamide;

4-[[(3-chloro-4-methoxyphenyl)methyl]amino]-1-ethyl-N-[(4-pyridinyl-1-oxide) methyl]-1H-pyrazolo[3,4-b]pyridine-5-carboxamide;

4-[[(3-chloro-4-methoxyphenyl)methyl]amino]-1-ethyl-N-(2-furanylmethyl)-1H-pyrazolo[3,4-b]pyridine-5-carboxamide;

N-[[4-[[(3-chloro-4-methoxyphenyl)methyl]amino]-1-ethyl-1H-pyrazolo[3,4-b]pyridin-5-yl]carbonyl]-L-valine, ethyl ester;

4-[[(3-chloro-4-methoxyphenyl)methyl]amino]-1-ethyl-N-(1,2,3,4-tetrahydro-1-naphthylenyl)-1H-pyrazolo[3,4-b]pyridine-5-carboxamide;

4-[[(3-chloro-4-methoxyphenyl)methyl]amino]-1-ethyl-N-(tetrahydro-2-furanylmethyl)-1H-pyrazolo[3,4-b]pyridine-5-carboxamide;

4-[[(3-chloro-4-methoxyphenyl)methyl]amino]-N-[[4-(dimethylamino)phenyl]methyl]-1-ethyl-1H-pyrazolo[3,4-b]pyridine-5-carboxamide;

N-[[4-[[(3-chloro-4-methoxyphenyl)methyl]amino]-1-ethyl-1H-pyrazolo[3,4-b]pyridin-5-yl]carbonyl]-L-alanine, methyl ester;

4-[[(3-chloro-4-methoxyphenyl)methyl]amino]-1-ethyl-N-[[4-fluoro-2-(trifluoromethyl)phenyl]methyl]-1H-pyrazolo[3,4-b]pyridine-5-carboxamide;

N-[[(4-[[(3-chloro-4-methoxyphenyl)methyl]amino]-1-ethyl-1H-pyrazolo[3,4-b]pyridin-5-yl]carbonyl]-L-methionine, methyl ester;

2-[[[4-[[(3-chloro-4-methoxyphenyl)methyl]amino]-1-ethyl-1H-pyrazolo[3,4-b]pyridin-5-yl]carbonyl]amino]propanedioic acid, diethyl ester;

4-[[(3-chloro-4-methoxyphenyl)methyl]amino]-1-ethyl-N-(2-oxo-2-phenylethyl)-1H-pyrazolo[3,4-b]pyridine-5-carboxamide;

4-[[(3-chloro-4-methoxyphenyl)methyl]amino]-1-ethyl-N-[2-(4-morpholinyl)ethyl]-1H-pyrazolo[3,4-b]pyridine-5-carboxamide;

N-[[4-[[(3-chloro-4-methoxyphenyl)methyl]amino]-1-ethyl-1H-pyrazolo[3,4-b]pyridin-5-yl]carbonyl]-L-asparagine,1,1-dimethylethyl ester;

(S)-4-[[(3-chloro-4-methoxyphenyl)methyl]amino]-1-ethyl-N-[2-oxo-3-[2-oxo-2-(1-pyrrolidinyl)-ethyl]cycloheptyl]-1H-pyrazolo[3,4-b]pyridine-5-carboxamide;

(S)-α-[[[4-[[(3-chloro-4-methoxyphenyl)methyl]amino]-1-ethyl-1H-pyrazolo[3,4-b]pyridin-5-yl]carbonyl]amino]-4-hydroxybenzeneacetic acid;

4-[[(3-chloro-4-methoxyphenyl)methyl]amino]-1-ethyl-N-(2-pyridinylmethyl)-1H-pyrazolo[3,4-b]pyridin-5-carboxylate;

4-[[(3-chloro-4-methoxyphenyl)methyl]amino]-1-ethyl-N-(4-pyridinylmethyl)-1H-pyrazolo[3,4-b]pyridin-5-carboxylate;

4-[[(3-chloro-4-methoxyphenyl)methyl]amino]-1-ethyl-N-[3-(4-morpholinyl)ethyl]-1H-pyrazolo[3,4-b]pyridin-5-carboxylate;

4-[[(3-chloro-4-methoxyphenyl)methyl]amino]-1-ethyl-N-(4-pyridinylmethyl]-1H-pyrazolo[3,4-b]pyridin-5-carboxamide;

4-[[(3-chloro-4-methoxyphenyl)methyl]amino]-1-ethyl-N-(2-pyridinylmethyl)-1H-pyrazolo[3,4-b]pyridin-5-carboxamide;

(R)-4-[[(3-chloro-4-methoxyphenyl)methyl]amino]-1-ethyl-N-(2-tetrahydrofurylmethyl)-1H-pyrazolo[3,4-b]pyridine-5-carboxamide;

(S)-4-[[(3-chloro-4-methoxyphenyl)methyl]amino]-1-ethyl-N-(2-tetrahydrofurylmethyl)-1H-pyrazolo[3,4-b]pyridine-5-carboxamide;

4-[[(3-chloro-4-methoxyphenyl)methyl]amino]-1-ethyl-N-(hexahydro-2-oxo-1H-azepin-3-yl)-1H-pyrazolo[3,4-b]pyridin-5-carboxamide;

4-[[(3-chloro-4-methoxyphenyl)methyl]amino]-N-(cyanomethyl)-1-ethyl-1H-pyrazolo[3,4-b]pyridin-5-carboxamide;

(S)-α-[[[4-[[(3-chloro-4-methoxyphenyl)-methyl]amino-1-ethyl-1H-pyrazolo[3,4-b]pyridine-5-yl]carbonyl]amino]-4-hydroxybenzeneacetic acid;

4-[[[4-[[(3-chloro-4-methoxyphenyl)methyl]amino-1-ethyl-1H-pyrazolo[3,4-b]pyridine-5-yl]carbonyl]amino]butanoic acid, methyl ester; and 4-[[(3-chloro-4-methoxyphenyl)methyl]hydroxyl]-1-ethyl-N-(4-pyridinylmethyl)-1H-pyrazolo[3,4-b]pyridin-5-carboxamide; or a pharmaceutically acceptable salt thereof.

14. The compound of claim 13 which is 4-[[(3-Chloro-4-methoxyphenyl)methyl]amino]-1-ethyl-N-(4-pyridinylmethyl)-1H-pyrazolo[3,4-b]pyridine-5-carboxamide.

15. A pharmaceutical composition useful for treating one or more cGMP associated conditions comprising a compound of claim 1 or a pharmaceutically-acceptable salt thereof and a pharmaceutically acceptable carrier.

16. A pharmaceutical composition useful for treating one or more cGMP associated conditions comprising a compound of claim 3 or a pharmaceutically acceptable salt thereof and a pharmaceutically acceptable carrier.

17. The pharmaceutical composition of claim 16 wherein the compound is 4-[[(3-chloro-4-methoxyphenyl)methyl]amino]-1-ethyl-N-(4-pyridinylmethyl)-1H-pyrazolo[3,4-b]pyridine-5-carboxamide or a pharmaceutically acceptable salt thereof.

18. A method of treating a mammalian host to relieve one or more cGMP associated conditions comprising administering to said host in need of such treatment an effective amount of a composition of claim 15.

19. The method of claim 18 wherein the one or more cGMP-associated condition being treated is erectile dysfunction.

20. The method of claim 18 in which the one or more cGMP-associated conditions are selected from disorders of gut motility and diabetes mellitus.

21. A method of treating a mammalian host to relieve one or more cGMP associated conditions comprising administering to said host in need of such treatment an effective amount of a composition of claim 16.

22. The method of claim 21 wherein the one or more cGMP associated condition being treated is erectile dysfunction.

23. A method of treating a mammalian host to relieve one or more cGMP associated conditions comprising administering to said host in need of such treatment an effective amount of a composition of claim 17.

* * * * *